US009139538B2

(12) United States Patent
Didiuk et al.

(10) Patent No.: US 9,139,538 B2
(45) Date of Patent: Sep. 22, 2015

(54) QUINOLINYL GLUCAGON RECEPTOR MODULATORS

(71) Applicant: Pfizer Inc., New York, NY (US)

(72) Inventors: Mary Didiuk, Madison, CT (US); Kevin J. Filipski, Reading, MA (US); Angel Guzman-Perez, Belmont, MA (US); Esther C. Lee, Brookline, MA (US); Jeffrey A. Pfefferkorn, Acton, MA (US); Benjamin Stevens, Cambridge, MA (US); Meihua Tu, Acton, MA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 14/564,263

(22) Filed: Dec. 9, 2014

(65) Prior Publication Data

US 2015/0099882 A1 Apr. 9, 2015

Related U.S. Application Data

(63) Continuation of application No. 14/232,379, filed as application No. PCT/IB2012/053575 on Jul. 12, 2012, now Pat. No. 8,927,577.

(60) Provisional application No. 61/642,077, filed on May 3, 2012, provisional application No. 61/510,582, filed on Jul. 22, 2011.

(51) Int. Cl.
C07D 215/58 (2006.01)
C07D 241/44 (2006.01)
C07D 215/38 (2006.01)
C07D 239/94 (2006.01)
C07D 217/22 (2006.01)
C07D 239/84 (2006.01)

(52) U.S. Cl.
CPC ............ C07D 241/44 (2013.01); C07D 215/38 (2013.01); C07D 217/22 (2013.01); C07D 239/84 (2013.01); C07D 239/94 (2013.01)

(58) Field of Classification Search
CPC ................................................... C07D 215/58
See application file for complete search history.

(56) References Cited

U.S. PATENT DOCUMENTS

| | | | |
|---|---|---|---|
| 5,776,954 A | 7/1998 | de Laszlo et al. |
| 5,837,719 A | 11/1998 | de Laszlo et al. |
| 5,880,139 A | 3/1999 | Chang |
| 5,939,359 A | 8/1999 | Engel et al. |
| 6,103,720 A | 8/2000 | Lubisch et al. |
| 6,211,242 B1 | 4/2001 | Setoi et al. |
| 6,218,431 B1 | 4/2001 | Schoen et al. |
| 7,151,114 B2 | 12/2006 | Streicher et al. |
| 7,687,534 B2 | 3/2010 | Stelmach et al. |
| 2003/0203946 A1 | 10/2003 | Behrens et al. |
| 2004/0097552 A1 | 5/2004 | Duffy et al. |
| 2004/0097557 A1 | 5/2004 | Duffy et al. |
| 2004/0209928 A1 | 10/2004 | Kurukulasuriya et al. |
| 2004/0209943 A1 | 10/2004 | Erickson et al. |
| 2004/0266856 A1 | 12/2004 | Chu et al. |
| 2005/0272794 A1 | 12/2005 | Parmee et al. |
| 2006/0094764 A1 | 5/2006 | Anderskewitz et al. |
| 2006/0122256 A1 | 6/2006 | Gillespie et al. |
| 2007/0088070 A1 | 4/2007 | Parmee et al. |
| 2007/0088071 A1 | 4/2007 | Kim et al. |

(Continued)

FOREIGN PATENT DOCUMENTS

| | | |
|---|---|---|
| CN | 102206172 | 10/2011 |
| DE | 10300398 | 1/2003 |

(Continued)

OTHER PUBLICATIONS

Sinz, et al., "Discovery of 2-acylindoles as potent, orally active human glucagon receptor antagonists." Abstracts of Papers, 235th ACS National Meeting, New Orleans, LA, United States, Apr. 6-10, 2008, MEDI-016.

Collins, et al., CP-99,711: A nonpeptide glucagon receptor antagonist. Bioorganic & Medicinal Chemistry Letters, vol. 2(9), pp. 915-918 (1992).

Kumar, et al., "Quantitative Structure-Activity Relationships of Selective Antagonists of Glucagon Receptor Using QuaSAR Descriptors", Chem. Pharm. Bull., vol. 54(11), pp. 1586-1591 (2006).

Madsen, et al., "Advances in Non-Peptide Glucagon Receptor Antagonists", Current Pharm. Design, vol. 5(9), pp. 683-691 (1999).

(Continued)

Primary Examiner — Bruck Kifle
(74) Attorney, Agent, or Firm — James T. Wasicak

(57) ABSTRACT

The present invention provides a compound of Formula I

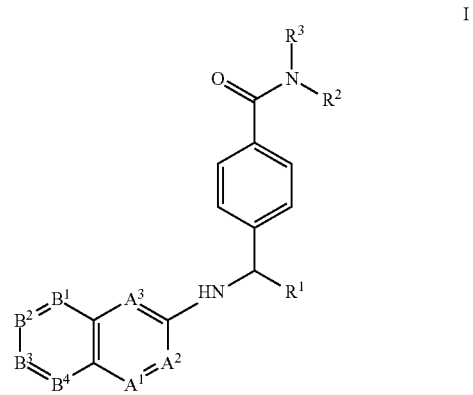

or a pharmaceutically acceptable salt thereof, wherein $R^1$, $R^2$, $R^3$, $A^1$, $A^2$, $A^3$, $B^1$, $B^2$, $B^3$ and $B^4$ are as defined herein. The compounds of Formula I have been found to act as glucagon antagonists or inverse agonists. Consequently, the compounds of Formula I and the pharmaceutical compositions thereof are useful for the treatment of diseases, disorders, or conditions mediated by glucagon.

8 Claims, No Drawings

(56) References Cited

U.S. PATENT DOCUMENTS

| | | |
|---|---|---|
| 2012/0053173 A1 | 3/2012 | Banno et al. |
| 2012/0059012 A1 | 3/2012 | Fujii et al. |

FOREIGN PATENT DOCUMENTS

| | | |
|---|---|---|
| GB | 2292149 | 2/1996 |
| JP | 10259176 | 9/1998 |
| JP | 200560835 | 3/2005 |
| JP | 2009040702 | 2/2009 |
| WO | 9219210 | 11/1992 |
| WO | 9414427 | 7/1994 |
| WO | 9421590 | 9/1994 |
| WO | 9609818 | 4/1996 |
| WO | 9716442 | 5/1997 |
| WO | 9804528 | 2/1998 |
| WO | 9822109 | 5/1998 |
| WO | 9824780 | 6/1998 |
| WO | 9824782 | 6/1998 |
| WO | 9901423 | 1/1999 |
| WO | 9924404 | 5/1999 |
| WO | 9932448 | 7/1999 |
| WO | 0064876 | 11/2000 |
| WO | 0064888 | 11/2000 |
| WO | 0069810 | 11/2000 |
| WO | 0200612 | 1/2002 |
| WO | 0240446 | 5/2002 |
| WO | 02704624 | 9/2002 |
| WO | 03047626 | 6/2003 |
| WO | 03048109 | 6/2003 |
| WO | 03051357 | 6/2003 |
| WO | 03053938 | 7/2003 |
| WO | 03055482 | 7/2003 |
| WO | 03064404 | 8/2003 |
| WO | 03080545 | 10/2003 |
| WO | 03087044 | 10/2003 |
| WO | 03097619 | 11/2003 |
| WO | 2004002480 | 1/2004 |
| WO | 2004002481 | 1/2004 |
| WO | 2004024066 | 3/2004 |
| WO | 2004050039 | 6/2004 |
| WO | 2004056763 | 7/2004 |
| WO | 2004063147 | 7/2004 |
| WO | 2004069158 | 8/2004 |
| WO | 2004092146 | 10/2004 |
| WO | 2004099170 | 11/2004 |
| WO | 2004100875 | 11/2004 |
| WO | 2005014534 | 2/2005 |
| WO | 2005058845 | 6/2005 |
| WO | 2005065680 | 7/2005 |
| WO | 2005118542 | 12/2005 |
| WO | 2005123668 | 12/2005 |
| WO | 2006014618 | 2/2006 |
| WO | 2006017055 | 2/2006 |
| WO | 2006042850 | 4/2006 |
| WO | 2006086488 | 8/2006 |
| WO | 2006102067 | 9/2006 |
| WO | 2006104826 | 10/2006 |
| WO | 2007015999 | 2/2007 |
| WO | 2007022380 | 2/2007 |
| WO | 2007040445 | 4/2007 |
| WO | 2007059195 | 5/2007 |
| WO | 2007072179 | 6/2007 |
| WO | 2007091396 | 8/2007 |
| WO | 2007106181 | 9/2007 |
| WO | 2007111864 | 10/2007 |
| WO | 2007114855 | 10/2007 |
| WO | 2007120270 | 10/2007 |
| WO | 2007120284 | 10/2007 |
| WO | 2007123581 | 11/2007 |
| WO | 2007136577 | 11/2007 |
| WO | 2008042223 | 4/2008 |
| WO | 2008098244 | 8/2008 |
| WO | 2009035558 | 3/2009 |
| WO | 2009057784 | 5/2009 |
| WO | 2009110520 | 9/2009 |
| WO | 2009111700 | 9/2009 |
| WO | 2009125424 | 10/2009 |
| WO | 2009140342 | 11/2009 |
| WO | 2010019828 | 2/2010 |
| WO | 2010019830 | 2/2010 |
| WO | 2010030722 | 3/2010 |
| WO | 2010039789 | 4/2010 |
| WO | 2010071750 | 6/2010 |
| WO | 2010080971 | 7/2010 |
| WO | 2010088061 | 8/2010 |
| WO | 2010098948 | 9/2010 |
| WO | 2010098994 | 9/2010 |
| WO | 2010131669 | 11/2010 |
| WO | 2010144664 | 12/2010 |
| WO | 2011007722 | 1/2011 |
| WO | 2011037815 | 3/2011 |
| WO | 2011119541 | 9/2011 |
| WO | 2011119559 | 9/2011 |
| WO | 2011027849 | 10/2011 |

OTHER PUBLICATIONS

Parker, et al., "Effects of skyrin, a receptor-selective glucagon antagonist, in rat and human hepatocytes", Diabetes vol. 49(12), pp. 2079-2086 (2000).

Qureshi, et al., "A novel glucagon receptor antagonist inhibits glucagon-mediated biological effects", Diabetes, vol. 53(12), pp. 3267-3273 (2004).

Petersen, et al., "Effects of a novel glucagon receptor antagonist (Bay 27-9955) on glucagon-stimulated glucose production in humans", Diabetologia, vol. 44(11), pp. 2018-2024 (2001).

Winzell, et al., "Glucagon receptor antagonism improves islet function in mice with insulin resistance induced by a high-fat diet", Diabetologia, vol. 50(7), pp. 1453-1462 (2007).

Mu, et al., "Chronic treatment with a glucagon receptor antagonist lowers glucose and moderately raises circulating glucagon and glucagon-like peptide 1 without severe alpha cell hypertrophy in diet-induced obese mice", Diabetologia, vol. 54(9), pp. 2381-2391 (2011).

Ling, et al., "Small-molecule glucagon receptor antagonists", Drugs of the Future, vol. 27(10), pp. 987-993 (2002).

Guillon, et al., "Synthesis of new pyrrolo[1,2-a]quinoxalines: potential non-peptide glucagon receptor antagonists", European Journal of Medicinal Chemistry, vol. 33(4), pp. 293-308 (1998).

Dallas-Yang, et al., Hepatic glucagon receptor binding and glucose-lowering in vivo by peptidyl and non-peptidyl glucagon receptor antagonists. European Journal of Pharmacology, vol. 501(1-3), pp. 225-234 (2004).

Yang, et al., "Cloning and expression of canine glucagon receptor and its use to evaluate glucagon receptor antagonists in vitro and in vivo", European Journal of Pharmacology, vol. 555(1), pp. 8-16 (2007).

Sloop, et al., "Glucagon as a target for the treatment of Type 2 diabetes", Expert Opinion on Therapeutic Targets, vol. 9(3), pp. 593-600 (2005).

Ling, et al., "Approaches to glucagon receptor antagonists", Expert Opinion on Therapeutic Patents, vol. 13(1), pp. 15-22 (2003).

Kurukulasuriya, et al., "Progress towards glucagon receptor antagonist therapy for Type 2 diabetes", Expert Opinion on Therapeutic Patents, vol. 15(12), pp. 1739-1749 (2005).

Shen, et al., "A survey of small molecule glucagon receptor antagonists from recent patents (2006-2010)", Expert Opinion on Therapeutic Patents, vol. 21(8), pp. 1211-1240 (2011).

Cascieri, et al., "Characterization of a novel, non-peptidyl antagonist of the human glucagon receptor", Journal of Biological Chemistry, vol. 274(13), pp. 8694-8697 (1999).

Johansen, et al., "Labelling of a potent glucagon receptor antagonist with tritium, carbon-14 and stable isotopes", Journal of Labelled Compounds and Radiopharmaceuticals, vol. 50(5-6), pp. 466-467 (2007).

Madsen, et al., "Discovery and Structure-Activity Relationship of the First Non-Peptide Competitive Human Glucagon Receptor Antagonists", Journal of Medicinal Chemistry, vol. 41(26), pp. 5150-5157 (1998).

(56) References Cited

OTHER PUBLICATIONS

Ling, et al., Identification of Alkylidene Hydrazides as Glucagon Receptor Antagonists, Journal of Medicinal Chemistry, vol. 44(19), pp. 3141-3149 (2001).
Madsen, et al., "Optimization of Alkylidene Hydrazide Based Human Glucagon Receptor Antagonists. Discovery of the Highly Potent and Orally Available 3-Cyano-4-hydroxybenzoic Acid [1-(2,3,5,6-Tetramethylbenzyl)-1H-indol-4-ylmethylene]hydrazide. Journal of Medicinal Chemistry", vol. 45(26), pp. 5755-5775 (2002).
Lau, et al., "New b-alanine derivatives are orally available glucagon receptor antagonists", Journal of Medicinal Chemistry, vol. 50(1), pp. 113-128 (2007).
Kodra, et al., "Novel Glucagon Receptor Antagonists with Improved Selectivity over the Glucose-Dependent Insulinotropic Polypeptide Receptor", Journal of Medicinal Chemistry, vol. 51(17), pp. 5387-5396 (2008).
Madsen, et al., "Human Glucagon Receptor Antagonists with Thiazole Cores. A Novel Series with Superior Pharmacokinetic Properties", Journal of Medicinal Chemistry, vol. 52(9), pp. 2989-3000 (2009).
Rivera, et al., "A novel glucagon receptor antagonist, NNC 25-0926, blunts hepatic glucose production in the conscious dog", Journal of Pharmacology and Experimental Therapeutics, vol. 321(2), pp. 743-752 (2007).
Chen, et al., "Insight into the bioactivity and metabolism of human glucagon receptor antagonists from 3D-QSAR analyses", QSAR & Combinatorial Science, vol. 23(8), pp. 603-620 (2004).
Ladouceur, et al., "4-Phenylpyridine glucagon receptor antagonists: synthetic approaches to the sterically hindered chiral hydroxy group", Tetrahedron Letters, vol. 43(25), pp. 4455-4458 (2002).
Filipski, et al., "A novel series of glucagon receptor antagonists with reduced molecular weight and lipophilicity", Bioorganic & Medicinal Chemistry Letters, vol. 22(1), pp. 415-420 (2012).
Sinz, et al., "Discovery of cyclic guanidines as potent, orally active, human glucagon receptor antagonists", Bioorganic & Medicinal Chemistry Letters, vol. 21(23), pp. 7131-7136 (2011).
Sinz, et al., "Discovery of N-Aryl-2-acylindole human glucagon receptor antagonists", Bioorganic & Medicinal Chemistry Letters, vol. 21(23), pp. 7124-7130 (2011).
Shen, et al., "Discovery of novel, potent, selective, and orally active human glucagon receptor antagonists containing a pyrazole core", Bioorganic & Medicinal Chemistry Letters, vol. 21(1), pp. 76-81 (2011).
Kim, et al., "Discovery of potent, orally active benzimidazole glucagon receptor antagonists", Bioorganic & Medicinal Chemistry Letters, vol. 18(13), pp. 3701-3705 (2008).
DeMong, et al., "Glucagon receptor antagonists for type II diabetes", Annual Reports in Medicinal Chemistry, vol. 43, pp. 119-137 (2008).
Liang, et al., "Design and synthesis of conformationally constrained tri-substituted ureas as potent antagonists of the human glucagon receptor", Bioorganic & Medicinal Chemistry Letters, vol. 17(3), pp. 587-592 (2007).
Karthikeyan, et al., "Quantitative structure activity relationships of some selective inhibitors of glucagon receptor: a Hansch approach", Asian Journal of Biochemistry, vol. 1(4), pp. 307-315 (2006).
Cohen, et al., "Direct observation (NMR) of the efficacy of glucagon receptor antagonists in murine liver expressing the human glucagon receptor", Bioorganic & Medicinal Chemistry Letters, vol. 14(5), pp. 1506-1517 (2006).
Shen, et al., "Discovery of novel, potent, and orally active spiro-urea human glucagon receptor antagonists", Bioorganic & Medicinal Chemistry Letters, vol. 15(20), pp. 4564-4569 (2005).
Duffy, et al., "Discovery and investigation of a novel class of thiophene-derived antagonists of the human glucagon receptor", Bioorganic & Medicinal Chemistry Letters, vol. 15(5), pp. 1401-1405 (2005).
Kurukulasuriya, et al., "Biaryl amide glucagon receptor antagonists", Bioorganic & Medicinal Chemistry Letters, vol. 14(9), pp. 2047-2050 (2004).
Smith, et al., "Optimization of the 4-aryl group of 4-aryl-pyridine glucagon antagonists: development of an efficient, alternative synthesis", Bioorganic & Medicinal Chemistry Letters, vol. 12(9), pp. 1303-1306 (2002).
Ling, et al., "Human glucagon receptor antagonists based on alkylidene hydrazides", Bioorganic & Medicinal Chemistry Letters, vol. 12(4), pp. 663-666 (2002).
Ladouceur, et al., "Integration of optimized substituent patterns to produce highly potent 4-aryl-pyridine glucagon receptor antagonists", Bioorganic & Medicinal Chemistry Letters, vol. 12(23), pp. 3421-3424 (2002).
Ladouceur, et al., "Discovery of 5-Hydroxyalkyl-4-phenylpyridines as a New Class of Glucagon Receptor Antagonists", Bioorganic & Medicinal Chemistry Letters, vol. 12(3), pp. 461-464 (2002).
Chang, et al., "Substituted Imidazoles as Glucagon Receptor Antagonists", Bioorganic & Medicinal Chemistry Letters, vol. 11(18), pp. 2549-2553 (2001).
deLaszlo, et al., "Potent, orally absorbed glucagon receptor antagonists", Bioorganic & Medicinal Chemistry Letters, vol. 9(5), pp. 641-646 (1999).
Kodra, et al., "Nonpeptide orally bioavailable glucagon receptor antagonists", Abstracts of Papers, 237th ACS National Meeting, Salt Lake City, UT, United States, Mar. 22-26, 2009, MEDI-166.
Dai, et al., "Discovery of a highly potent and selective imidazolone-based glucagon receptor antagonist", Abstracts of Papers, 241st ACS National Meeting & Exposition, Anaheim, CA, United States, Mar. 27-31, 2011, MEDI-22.
Parmee, "Discovery of MK-0893: A glucagon receptor antagonist for the treatment of type II diabetes", Abstracts of Papers, 241st ACS National Meeting & Exposition, Anaheim, CA, United States, Mar. 27-31, 2011, MEDI-31.
Handlon, et al., Glucagon receptor antagonists for the treatment of type 2 diabetes. Abstracts of Papers, 226th ACS National Meeting, New York, NY, United States, Sep. 7-11, 2003, MEDI-164.
Djuric, et al., "Glucagon receptor antagonists for the treatment of type II diabetes: current prospects", Current Opinion in Investigational Drugs vol. 3(11), pp. 1617-1623 (2002).
Kurukulasuriya, et al., "Towards a potent small molecule Glucagon receptor antagonist", Abstracts of Papers, 228th ACS National Meeting, Philadelphia, PA, United States, Aug. 22-26, 2004, MEDI-035.
JPET Fast Forward, Published on Feb. 16, 2007 as DOI:10.1124/JPET.106.115717, "A novel glucagon receptor antagonist, NNC25,0926, blunts hepatic glucose production in the conscious dog".
Business Wire, Sep. 17, 2007, "Metabasis Therapeutics Presents Promising Preclinical Results with Its Novel Glucagon Antagonist for the Treatment of Type 2 Diabetes", http://findarticles.com/p/articles/mi_m0EIN/is_2007_Sept_17/ai_n19522058/, downloaded Oct. 19, 2010.
Marsham, et al., "Qunazoline antifolate thymidylate synthase inhibitors: bridge modifications and conformationally restricted analogs in the C2-methyl series", Journal of Medicinal Chemistry, vol. 34(7), pp. 2209-2218 (1991).

QUINOLINYL GLUCAGON RECEPTOR MODULATORS

FIELD OF THE INVENTION

The present invention relates to compounds that are antagonists, mixed agonists/antagonists, partial agonists, negative allosteric modulators or inverse agonists of the glucagon receptor, pharmaceutical compositions comprising the compounds, and the uses of the compounds or compositions.

BACKGROUND

Diabetes is a major public health concern because of its increasing prevalence and associated health risks. The disease is characterized by metabolic defects in the production and utilization of carbohydrates which result in the failure to maintain appropriate blood glucose levels. Two major forms of diabetes are recognized. Type I diabetes, or insulin-dependent diabetes mellitus (IDDMT1DM), is the result of an absolute deficiency of insulin. Type II diabetes, or non-insulin dependent diabetes mellitus (NIDDMT2DM), often occurs with normal, or even elevated levels of insulin and appears to be the result of the inability of tissues and cells to respond appropriately to insulin. Aggressive control of NIDDM T2DM with medication is essential; otherwise it can progress into β-cell failure and insulin dependence.

Glucagon is a twenty nine amino acid peptide which is secreted from the a cells of the pancreas into the hepatic portal vein thereby exposing the liver to higher levels of this hormone than non-hepatic tissues. Plasma glucagon levels decrease in response to hyperglycemia, hyperinsulinemia, elevated plasma non-esterified fatty acid levels and somatostatin whereas glucagon secretion is increased in response to hypoglycemia and elevated plasma amino acid levels. Glucagon, through activation of its receptor, is a potent activator of hepatic glucose production by activating glycogenolysis and gluconeogenesis.

The glucagon receptor is a 62 kDa protein that is activated by glucagon and is a member of the class B G-protein coupled family of receptors. Other closely related G-protein coupled receptors include glucagon-like peptide-1 receptor (GLP-1), glucagon-like peptide-2 receptor (GLP-2) and gastric inhibitory polypeptide receptor. The glucagon receptor is encoded by the GCGR gene in humans and these receptors are mainly expressed in the liver with lesser amounts found in the kidney, heart, adipose tissue, spleen, thymus, adrenal glands, pancreas, cerebral cortex and gastrointestinal tract. Stimulation of the glucagon receptor results in activation of adenylate cyclase and increased levels of intracellular cAMP.

Reports have indicated that an uncommon missense mutation in the GCGR gene is correlated with diabetes mellitus type 2 and one reported inactivating mutation of the glucagon receptor in humans causes resistance to glucagon and is associated with pancreatic α-cell hyperplasia, nesidioblastosis, hyperglucagonemia and pancreatic neuroendocrine tumors. In rodent studies with GCGR knockout mice and mice treated with GCGR antisense oligonucleotides the mice exhibited improved fasting glucose, glucose tolerance and pancreatic β-cell function. In both healthy control animals and animal models of type 1 and type 2 diabetes, removal of circulating glucagon with selective and specific antibodies has resulted in a reduction of the glycemic level. More specifically, treatment of both mice and cynomolgus monkeys with GCGR-antagonizing antibodies (mAb B and mAb Ac) has been shown to improve glycemic control without causing hypoglycemia. Recent mice studies have further shown that antagonism of the glucagon receptor results in improved glucose homeostasis through a mechanism which requires a functional GLP-1 receptor. Antagonism of the glucagon receptor resulted in compensatory overproduction of GLP-1, likely from the pancreatic α-cells, and this may play an important role in intraislet regulation and maintenance of β-cell function.

A promising area of diabetes research involves the use of small molecule antagonists, mixed agonists/antagonists, partial agonists, negative allosteric modulators or inverse agonists of the glucagon receptor to lower the level of circulating glucagon and thereby lower the glycemic level. Therapeutically, it is anticipated that inactivation of the glucagon receptor would be an effective strategy for lowering blood glucose by reducing hepatic glucose output and normalizing glucose stimulated insulin secretion.

Consequently, a glucagon antagonist, mixed agonist/antagonist, partial agonist, negative allosteric modulator or or inverse agonist may provide therapeutic treatment for NIDDM T2DM, IDDM T1DM and associated complications, inter alia, hyperglycemia, dyslipidemia, insulin resistance syndrome, hyperinsulinemia, hypertension, and obesity.

Several drugs in five major categories, each acting by different mechanisms, are available for treating hyperglycemia and subsequently, NIDDM T2DM (Moller, D. E., "New drug targets for Type 2 diabetes and the metabolic syndrome" *Nature* 414; 821-827, (2001)): (A) Insulin secretogogues, including sulphonyl-ureas (e.g., glipizide, glimepiride, glyburide) and meglitinides (e.g., nateglidine and repaglinide) enhance secretion of insulin by acting on the pancreatic beta-cells. While this therapy can decrease blood glucose level, it has limited efficacy and tolerability, causes weight gain and often induces hypoglycemia. (B) Biguanides (e.g., metformin) are thought to act primarily by decreasing hepatic glucose production. Biguanides often cause gastrointestinal disturbances and lactic acidosis, further limiting their use. (C) Inhibitors of alpha-glucosidase (e.g., acarbose) decrease intestinal glucose absorption. These agents often cause gastrointestinal disturbances. (D) Thiazolidinediones (e.g., pioglitazone, rosiglitazone) act on a specific receptor (peroxisome proliferator-activated receptor-gamma) in the liver, muscle and fat tissues. They regulate lipid metabolism subsequently enhancing the response of these tissues to the actions of insulin. Frequent use of these drugs may lead to weight gain and may induce edema and anemia. (E) Insulin is used in more severe cases, either alone or in combination with the above agents.

Ideally, an effective new treatment for NIDDM T2DM would meet the following criteria: (a) it would not have significant side effects including induction of hypoglycemia; (b) it would not cause weight gain; (c) it would at least partially replace insulin by acting via mechanism(s) that are independent from the actions of insulin; (d) it would desirably be metabolically stable to allow less frequent usage; and (e) it would be usable in combination with tolerable amounts of any of the categories of drugs listed herein.

A number of publications have appeared which disclose non-peptide compounds which act at the glucagon receptor. For example, WO 03/048109, WO 2004/002480, WO 2005/123668, WO 2005/118542, WO 2006/086488, WO 2006/102067, WO 2007/106181, WO 2007/114855, WO 2007/120270, WO 2007/123581, WO 2009/110520 and Kurukulasuriya et al. *Bioorganic & Medicinal Chemistry Letters,* 2004, 14(9), 2047-2050 each disclose non-peptide compounds that act as glucagon receptor antagonists. Although investigations are on-going, there still exists a need for a more effective and safe therapeutic treatment for diabetes, particularly NIDDM and IDDM.

SUMMARY OF THE INVENTION

The present invention provides compounds of Formula I that act as glucagon receptor modulators, in particular, glucagon antagonists; which therefore, may be used in the treatment of diseases mediated by such antagonism (e.g., diseases related to Type 2 diabetes, Type 1 diabetes and diabetes-related and obesity-related co-morbidities). A first embodiment of the present invention are compounds of Formula I

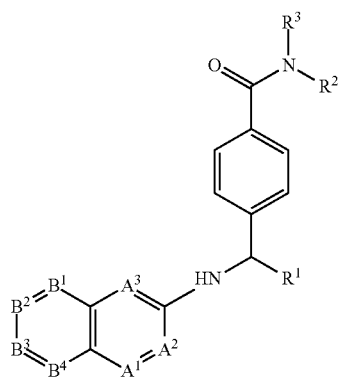

or a pharmaceutically acceptable salt thereof, wherein $R^1$ is $(C_1-C_6)$alkyl which is optionally substituted with one to three fluoro, hydroxy or methoxy; $(C_3-C_7)$cycloalkyl which is optionally substituted with one to two fluoro or one to two $(C_1-C_3)$alkyl which are each optionally substituted with one to three fluoro and wherein one carbon of the $(C_3-C_7)$cycloalkyl can be replaced with an O; or $(C_3-C_7)$cycloalkyl-$(C_1-C_6)$alkyl wherein the $(C_3-C_7)$cycloalkyl group of said $(C_3-C_7)$cycloalkyl-$(C_1-C_6)$alkyl is optionally substituted with one to two $(C_1-C_3)$alkyl which are each optionally substituted with one to three fluoro; $R^2$ is hydrogen or $(C_1-C_3)$alkyl; $R^3$ is tetrazolyl, —$CH_2$-tetrazolyl, —$(CH_2)_2SO_3H$, —$(CH_2)_2CO_2H$, —$CH_2CHFCO_2H$ or —$CH_2CH(OH)CO_2H$; $A^1$, $A^2$ and $A^3$ are each independently $CR^4$ or N, with the proviso that at least one but no more than two of $A^1$, $A^2$ and $A^3$ are N; $R^4$ at each occurrence is independently hydrogen, halo, cyano, $(C_1-C_3)$alkyl optionally substituted with one to three fluoro, $(C_1-C_3)$alkoxy optionally substituted with one to three fluoro, or $(C_3-C_5)$cycloalkyl; $B^1$, $B^2$, $B^3$ and $B^4$ are each independently $CR^5$ or N, with the proviso that no more than two of $B^1$, $B^2$, $B^3$ and $B^4$ are N; and $R^5$ at each occurrence is independently hydrogen, halo, cyano, $(C_1-C_3)$alkyl optionally substituted with one to three fluoro, or $(C_1-C_3)$alkoxy optionally substituted with one to three fluoro, or $(C_3-C_5)$cycloalkyl.

A second embodiment of the present invention is the compound of the first embodiment or a pharmaceutically acceptable salt thereof, wherein $R^2$ is hydrogen and $R^3$ is —$(CH_2)_2CO_2H$. A third embodiment of the present invention is the compound of the preceding embodiments or a pharmaceutically acceptable salt thereof wherein $R^1$ is ethyl, propyl, isopropyl, isobutyl, t-butyl, pentyl, neopentyl, cyclopropyl, cyclobutyl, cyclopentyl, cyclohexyl or cyclopropylmethyl each optionally substituted with 1 to 3 fluoro and wherein said cyclopropyl, cyclobutyl, cyclopentyl, cyclohexyl are each optionally substituted with 1 to 2 methyl.

A fourth embodiment of the present invention is the compound of the preceding embodiments or a pharmaceutically acceptable salt thereof wherein $B^1$, $B^2$, $B^3$ and $B^4$ are each $CR^5$. A fifth embodiment of the present invention is the compound of the preceding embodiments or a pharmaceutically acceptable salt thereof wherein
$A^1$ and $A^2$ are each $CR^4$ and $A^3$ is N; $R^4$ at each occurrence is independently hydrogen, fluoro, chloro, methyl or ethyl; and $R^5$ at each occurrence is independently hydrogen, fluoro, chloro, methyl, trifluoromethyl or methoxy. A sixth embodiment of the present invention is the compound of the first through fourth embodiments or a pharmaceutically acceptable salt thereof wherein $A^1$ is N and $A^2$ and $A^3$ are each $CR^4$; $R^4$ at each occurrence is independently hydrogen, fluoro, chloro, methyl or ethyl; and $R^5$ at each occurrence is independently hydrogen, fluoro, chloro, methyl, trifluoromethyl or methoxy. A seventh embodiment of the present invention is the compound of the first through fourth embodiments or a pharmaceutically acceptable salt thereof wherein $A^1$ and $A^3$ are each $CR^4$ and $A^2$ is N; $R^4$ at each occurrence is independently hydrogen, fluoro, chloro, methyl or ethyl;
and $R^5$ at each occurrence is independently hydrogen, fluoro, chloro, methyl, trifluoromethyl or methoxy.

An eighth embodiment of the present invention is the compound of the second embodiment or a pharmaceutically acceptable salt thereof wherein $A^1$ and $A^2$ are each $CR^4$ and $A^3$ is N; and $B^1$, $B^2$, $B^3$ and $B^4$ are each $CR^5$. A ninth embodiment of the present invention is the compound of the eighth embodiment or a pharmaceutically acceptable salt thereof wherein $R^1$ is ethyl, propyl, isopropyl, isobutyl, t-butyl, pentyl, neopentyl, cyclopropyl, cyclobutyl, cyclopentyl, cyclohexyl or cyclopropylmethyl each optionally substituted with 1 to 3 fluoro and wherein said cyclopropyl, cyclobutyl, cyclopentyl, cyclohexyl are each optionally substituted with 1 to 2 methyl. A tenth embodiment of the present invention is the compound of the ninth embodiment or a pharmaceutically acceptable salt thereof wherein $R^4$ at each occurrence is independently hydrogen, fluoro, chloro, methyl or ethyl; and $R^5$ at each occurrence is independently hydrogen, fluoro, chloro, methyl, trifluoromethyl or methoxy.

An eleventh embodiment of the present invention is the compound of the second embodiment or a pharmaceutically acceptable salt thereof wherein $A^2$ and $A^3$ are each $CR^4$ and $A^1$ is N; and $B^1$, $B^2$, $B^3$ and $B^4$ are each $CR^5$. A twelfth embodiment of the present invention is the compound of the eleventh embodiment or a pharmaceutically acceptable salt thereof wherein $R^1$ is ethyl, propyl, isopropyl, isobutyl, t-butyl, pentyl, neopentyl, cyclopropyl, cyclobutyl, cyclopentyl, cyclohexyl or cyclopropylmethyl each optionally substituted with 1 to 3 fluoro and wherein said cyclopropyl, cyclobutyl, cyclopentyl, cyclohexyl are each optionally substituted with 1 to 2 methyl. A thirteenth embodiment of the present invention is the compound of the twelfth embodiment or a pharmaceutically acceptable salt thereof wherein $R^4$ at each occurrence is independently hydrogen, fluoro, chloro, methyl or ethyl; and $R^5$ at each occurrence is independently hydrogen, fluoro, chloro, methyl, trifluoromethyl or methoxy.

Another embodiment of the present invention is a compound selected from the group consisting of (+/−)-3-(4-(1-(3-methylquinolin-2-ylamino)butyl)benzamido) propanoic acid; (+/−)-3-{4-[3-methyl-1-(quinolin-3-ylamino)-butyl]-benzoylamino}-propionic acid; (+/−)-3-{4-[1-(7-fluoro-quinazolin-2-ylamino)-3-methyl-butyl]-benzoylamino}-propionic acid; (+/−)-3-{4-[3-methyl-1-(quinolin-2-ylamino)-butyl]-benzoylamino}-propionic acid; (+/−)-3-{4-[1-(8-methoxy-quinolin-2-ylamino)-3-methyl-butyl]-benzoylamino}-propionic acid; (+/−)-3-{4-[3-methyl-1-(3- methyl-quinoxalin-2-ylamino)-butyl]-benzoylamino}-propionic acid; (+/−)-3-{4-[3-methyl-1-(quinoxalin-2-ylamino)-butyl]-benzoylamino}-propionic acid; (+/−)-3-{4-[3-methyl-1-(4-methyl-quinolin-2-ylamino)-butyl]-benzoylamino}-propionic acid; (+/−)-3-{4-[3-methyl-1-(3-methyl-quinolin-2-ylamino)-butyl]-benzoylamino}-propionic acid; (+/−)-3-{4-[1-(7-fluoro-4-methyl-quinolin-2-ylamino)-3-methyl-butyl]-benzoylamino}-propionic acid; (+/−)-3-{4-[1-(8-chloro-quinolin-2-ylamino)-3-methyl-butyl]-benzoylamino}-propionic acid; (+/−)-3-{4-[3-methyl-1-(quinazolin-2-ylamino)-butyl]-benzoylamino}-propionic acid; (+/−) 3-(4-(3-methyl-1-(7-(trifluoromethyl)quinolin-2-ylamino)butyl)benzamido)propanoic acid; (+/−)-3-(4-(3-methyl-1-(6-(trifluoromethyl)quinolin-2-ylamino)butyl)benzamido)propanoic acid; (+\−)-3-(4-(3-methyl-1-(2-methylquinolin-3-ylamino)butyl)benzamido)propanoic acid; (+\−)-3-(4-(3-methyl-1-(4-methylquinolin-3-ylamino)butyl)benzamido)propanoic acid; (+/−)-3-{4-[(3,3-dimethyl-cyclobutyl)-(3-methyl-quinolin-2-ylamino)-methyl]-benzoylamino}-propionic acid; (+/−)-3-{4-[(3,3-dimethyl-cyclobutyl)-(6-fluoro-3-methyl-quinolin-2-ylamino)-methyl]-benzoylamino}-propionic acid; (+/−)-3-{4-[(3,3-dimethyl-cyclobutyl)-(7-fluoro-3-methyl-quinolin-2-ylamino)-methyl]-benzoylamino}-propionic acid; (+/−) 3-(4-((3,3-dimethylcyclobutyl)(6-fluoroquinolin-3-ylamino)methyl)benzamido)propanoic acid; (+/−)-3-(4-((3,3-dimethylcyclobutyl)(7-fluoroquinolin-3-ylamino)methyl)benzamido) propanoic acid; (+/−)-3-(4-(4,4,4-trifluoro-1-(quinolin-3-ylamino)butyl)benzamido)propanoic acid; (+/−)-3-(4-((6,7-difluoroquinolin-3-ylamino)(3,3-dimethyl-cyclobutyl)methyl)benzamido)propanoic acid; (+/−)-3-(4-(3-methyl-1-(7-methylquinolin-3-ylamino)butyl)benzamido)propanoic acid; (+/−)-3-(4-(3-methyl-1-(8-methylquinolin-3-ylamino)butyl)benzamido)propanoic acid; (+/−)-3-(4-(3-methyl-1-(6-methylquinolin-3-ylamino)butyl)benzamido)propanoic acid; and (+/−)-3-(4-(3-methyl-1-(5-methylquinolin-3-ylamino)butyl)benzamido)propanoic acid; or a pharmaceutically acceptable salt thereof.

Yet another embodiment of the present invention is a compound selected from (+)-3-(4-(1-(3-methylquinolin-2-ylamino)butyl)benzamido)propanoic acid; (−)-3-(4-(1-(3-methylquinolin-2-ylamino)butyl)benzamido)propanoic acid; (+)-3-(4-(3-methyl-1-(3-methylquinolin-2-ylamino)butyl)benzamido)propanoic acid; (−)-3-(4-(3-methyl-1-(3-methylquinolin-2-ylamino)butyl)benzamido)propanoic acid; or a pharmaceutically acceptable salt thereof.

Another aspect of the present invention is a pharmaceutical composition that comprises (1) a compound of the present invention, and (2) a pharmaceutically acceptable excipient, diluent, or carrier. Preferably, the composition comprises a therapeutically effective amount of a compound of the present invention. The composition may also contain at least one additional pharmaceutical agent (described herein). Preferred agents include anti-obesity agents and/or anti-diabetic agents (described herein below).

In yet another aspect of the present invention is a method for treating a disease, condition, or disorder mediated by glucagon, in particular, deactivation (such as antagonism) of the glucagon receptor, in a mammal that includes the step of administering to a mammal, preferably a human, in need of such treatment a therapeutically effective amount of a compound of the present invention, or a pharmaceutical composition thereof.

Diseases, disorders, or conditions mediated by glucagon include Type II diabetes, Type I diabetes, hyperglycemia, metabolic syndrome, impaired glucose tolerance, glucosuria, cataracts, diabetic neuropathy, diabetic nephropathy, diabetic retinopathy, obesity, dyslididemia, hypertension, hyperinsulinemia, and insulin resistance syndrome. Preferred diseases, disorders, or conditions include Type II diabetes, hyperglycemia, impaired glucose tolerance, obesity, and insulin resistance syndrome. More preferred are Type II diabetes, Type I diabetes, hyperglycemia, and obesity. Most preferred is Type II and Type I diabetes.

In yet another aspect of the present invention is a method of reducing the level of blood glucose in a mammal, preferably a human, which includes the step of administering to a mammal in need of such treatment a therapeutically effective amount of a compound of the present invention, or a pharmaceutical composition thereof.

Compounds of the present invention may be administered in combination with other pharmaceutical agents (in particular, anti-obesity and anti-diabetic agents described herein below). The combination therapy may be administered as (a) a single pharmaceutical composition which comprises a compound of the present invention, at least one additional pharmaceutical agent described herein and a pharmaceutically acceptable excipient, diluent, or carrier; or (b) two separate pharmaceutical compositions comprising (i) a first composition comprising a compound of the present invention and a pharmaceutically acceptable excipient, diluent, or carrier, and (ii) a second composition comprising at least one additional pharmaceutical agent described herein and a pharmaceutically acceptable excipient, diluent, or carrier. The pharmaceutical compositions may be administered simultaneously or sequentially and in any order.

DEFINITIONS

As used herein, the term "alkyl" refers to a hydrocarbon radical of the general formula $C_nH_{2n+1}$. The alkane radical may be straight or branched. For example, the term "$(C_1-C_6)$ alkyl" refers to a monovalent, straight, or branched aliphatic group containing 1 to 6 carbon atoms (e.g., methyl, ethyl, n-propyl, i-propyl, n-butyl, i-butyl, s-butyl, t-butyl, n-pentyl, 1-methylbutyl, 2-methylbutyl, 3-methylbutyl, neopentyl, 3,3-dimethylpropyl, hexyl, 2-methylpentyl, and the like). Similarly, the alkyl portion (i.e., alkyl moiety) of an alkoxy, acyl (e.g., alkanoyl), alkylamino, dialkylamino, alkylsulfonyl, and alkylthio group have the same definition as above. When indicated as being "optionally substituted", the alkane radical or alkyl moiety may be unsubstituted or substituted with one or more substituents (generally, one to three substituents except in the case of halogen substituents such as perchloro or perfluoroalkyls).

The term "cycloalkyl" refers to nonaromatic rings that are fully hydrogenated and may exist as a single ring, bicyclic ring or a spiral ring. Unless specified otherwise, the carbocyclic ring is generally a 3- to 8-membered ring. For example, $(C_3-C_7)$cycloalkyl include groups such as cyclopropyl, cyclobutyl, cyclopentyl, cyclohexyl, cyclohexenyl, cycloheptyl, norbornyl (bicyclo[2.2.1]heptyl) and the like. In certain embodiments one or more of the carbon atoms in a cycloalkyl may be replaced with a heteroatom as specified, such as with an O, S, NH or N-alkyl.

The term "cycloalkyl-alkyl" means a radical of the cycloalkyl of specified size attached to a radical of the alkyl group of the specified size. For example, the term $(C_3-C_7)$ cycloalkyl-$(C_1-C_6)$alkyl means a three to seven membered cycloalkyl such as cyclopropyl, cyclobutyl, cyclopentyl, cyclohexyl or cycloheptyl which is attached to a one to six membered alkyl group.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "animal" refers to humans (male or female), companion animals (e.g., dogs, cats and horses), food-source animals, zoo animals, marine animals, birds and other similar animal species. "Edible animals" refers to food-source animals such as cows, pigs, sheep and poultry.

The phrase "pharmaceutically acceptable" indicates that the substance or composition must be compatible chemically and/or toxicologically, with the other ingredients comprising a formulation, and/or the mammal being treated therewith.

The terms "treating", "treat", or "treatment" embrace both preventative, i.e., prophylactic, and palliative treatment.

The terms "modulated" or "modulating", or "modulate(s)", as used herein, unless otherwise indicated, refers to the changes in activity of the glucagon receptor as a result of action of the compounds of the present invention.

The terms "mediated" or "mediating" or "mediate(s)", as used herein, unless otherwise indicated, refers to the treatment or prevention the particular disease, condition, or disorder, (ii) attenuation, amelioration, or elimination of one or more symptoms of the particular disease, condition, or disorder, or (iii) prevention or delay of the onset of one or more symptoms of the particular disease, condition, or disorder described herein, by modulation of glucagon.

The term "compounds of the present invention" (unless specifically identified otherwise) refer to compounds of Formula I and any pharmaceutically acceptable salts of the compounds, as well as, all stereoisomers (including diastereoisomers and enantiomers), tautomers, conformational isomers, and isotopically labeled compounds. Hydrates and solvates of the compounds of the present invention are considered compositions of the present invention, wherein the compound is in association with water or solvent, respectively.

The symbol "*" as used herein means a chiral center (carbon atom) that has either (R) or (S) absolute stereochemistry. The chiral center is at least 51% (R) or (S), preferably at least 80% (R) or (S) and most preferably greater than 95% (R) or (S).

DETAILED DESCRIPTION

Compounds of the present invention may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, New York (1967-1999 ed.), or *Beilsteins Handbuch der organischen Chemie*, 4, Aufl. ed. Springer-Verlag, Berlin, including supplements (also available via the Beilstein online database)).

For illustrative purposes, the reaction schemes depicted below provide potential routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). Similarly, a "hydroxy-protecting group" refers to a substituent of a hydroxy group that blocks or protects the hydroxy functionality. Suitable hydroxyl-protecting groups (O-Pg) include for example, allyl, acetyl, silyl, benzyl, para-methoxybenzyl, trityl, and the like. Suitable carboxylic acid-protecting groups (C(O)O-Pg) include for example, groups such as methyl, ethyl, t-butyl, benzyl, para-methoxybenzyl and diphenylmethylene. The need for such protection is readily determined by one skilled in the art. For a general description of protecting groups and their use, see T. W. Greene, *Protective Groups in Organic Synthesis*, John Wiley & Sons, New York, 1991.

Reaction Schemes I-IV provide general routes which can be employed to prepare compounds of Formula I. It is to be understood that the reaction schemes are illustrative and are not to be construed as a limitation in any manner.

Reaction Scheme I outlines the general procedures that can be used to provide compounds of the present invention within Formula I.

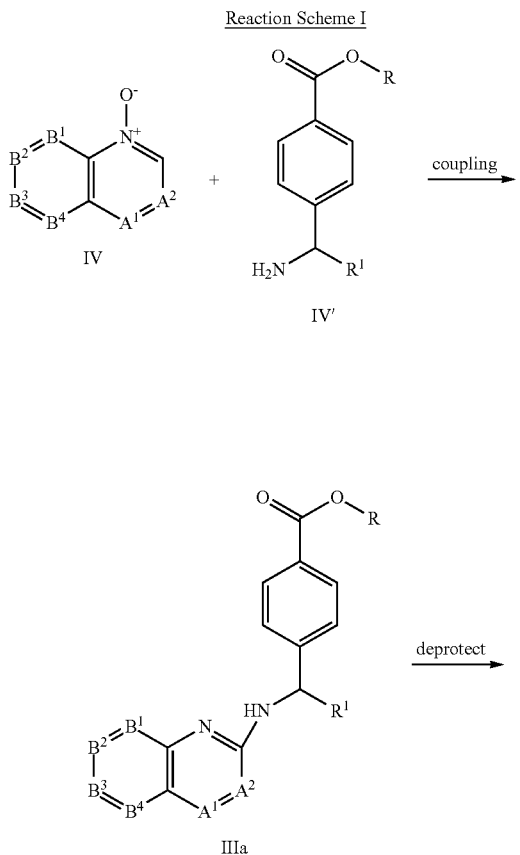

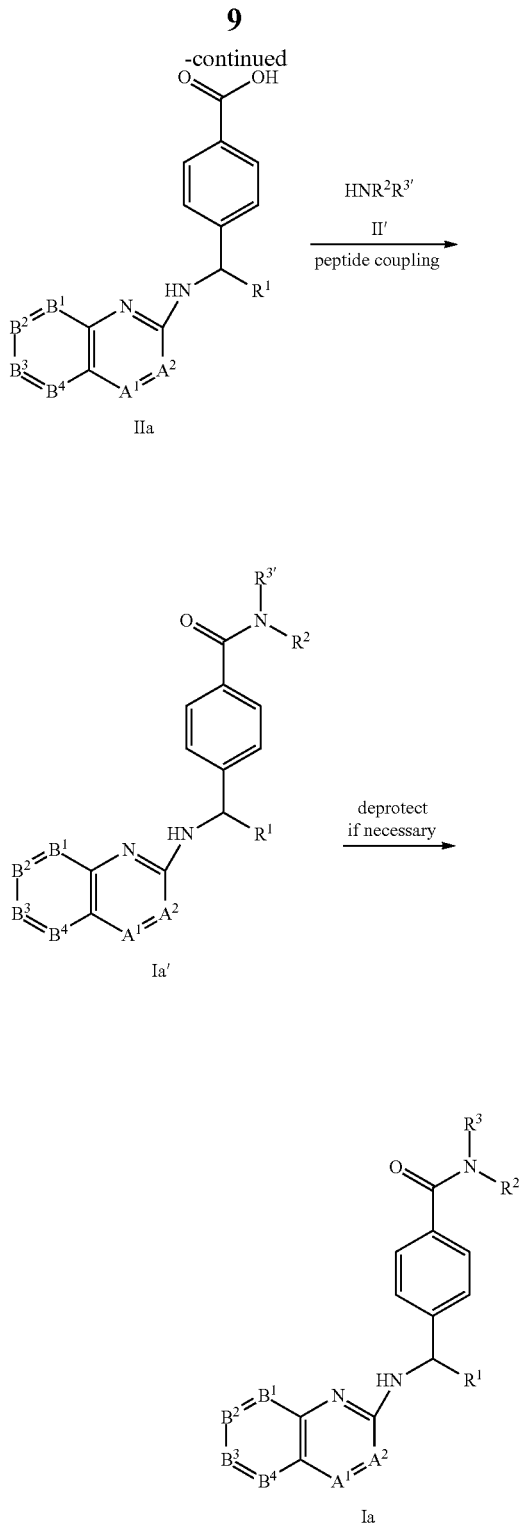

the corresponding compound with a non-oxidized nitrogen by treatment with an appropriate oxidizing agent such as hydrogen peroxide in acetic acid, typically at an elevated temperature, such as 80° C., for a period of 1 to 24 hours. Typically, the nucleophilic addition of the amine IV' to the quinoline N-oxide can be carried out under mild conditions using an appropriate phosphonium salt as an activator in the presence of an appropriate base and solvent. For example, the reaction between compounds of Formulae IV and IV' can be carried out using PyBroP (bromo-tris-pyrrolidino-phosphonium hexafluorophosphate) in the presence of an appropriate base such as diisopropylethylamine in an appropriate solvent such as dichloromethane or tetrahydrofuran at ambient temperature for a period of 1 to 24 hours (see Londregan, A. T. et al; in Org. Lett. 2010, 12, 5254-5257 and Org. Lett. 2011, 13(7), 1840-1843) to provide the compound of Formula IIIa. The ester moiety in the compound of Formula IIIa can then be deprotected under appropriate deprotection conditions to provide the free carboxylic acid compound of Formula IIa. When the group R in the compound of Formula IIIa represents a methyl or ethyl group the deprotection can be carried out using base catalyzed hydrolysis. For example, the compound of Formula IIIa can be treated with an appropriate base such as sodium hydroxide or lithium hydroxide in tetrahydrofuran and methanol at room temperature for a period of 1 to 24 hours. When the group R in the compound of Formula IIIa is t-butyl, para-methoxybenzyl or diphenylmethylene the deprotection can be carried out by treatment with an appropriate acid such as hydrochloric acid or trifluoroacetic acid in an appropriate solvent such as dichloromethane.

The free acid compound of Formula IIa can then undergoe a peptide coupling reaction with the amine $HNR^2R^{3'}$ (II') to provide the compound of Formula Ia'. Peptide coupling is carried out using standard literature conditions. The acid of Formula IIa can be converted to the corresponding acid chloride using a suitable chlorinating agent, such as oxalyl chloride or thionyl chloride, in a suitable solvent, such as dichloromethane or toluene, optionally in the presence of catalytic DMF, at a suitable temperature, typically of between 0° C. and room temperature. The acid chloride can then be reacted with the amine of generic formula $R^{3'}R^2NH$ in the presence of a base, such as triethylamine or diisopropylethylamine, in a suitable solvent, such as dichloromethane or toluene, at a temperature of between 0° C. and room temperature. $R^{3'}$ can represent either $R^3$ itself or a protected version of $R^3$ which can be subsequently deprotected to provide $R^3$. Alternatively, the acid of Formula IIa can be converted to a suitable activated species with a coupling agent, such as EDCI.HCl, HBTU, HATU, PyBop, DCC, or CDI, in a suitable solvent, such as dichloromethane, acetonitrile or DMF. In the presence of EDCI.HCl, HOBT is typically added. EDCI is 1-ethyl-3-(3-dimethylaminopropyl)carbodiimide; HBTU is O-Benzotriazole-N,N,N',N'-tetramethyluronium hexafluorophosphate; HATU is O-(7-Azabenzotriazol-1-yl)-N,N,N',N'-tetramethyluronium hexafluorophosphate; PyBop is Benzotriazol-1-yloxytripyrrolidinophosphonium hexafluorophosphate; DCC is dicyclohexylcarbodiimide; CDI is N,N'-carbonyldiimidazole and HOBT is 1-hydroxy benzotriazole. A suitable base, such as triethylamine or diisopropylethylamine, is also used and the reaction is typically carried out at room temperature. In the instance where $R^{3'}$ represents a protected version of $R^3$, subsequent deprotection can then be carried out by methods known in the art to provide $R^3$. For example, when $R^3$ is an ester, appropriate acid or base catalyzed hydrolysis can be carried out as described previously to provide the corresponding free acid in the compound of Formula Ia.

The first step of Reaction Scheme I depicts the nucleophic substitution reaction carried out with the nucleophilic amine of Formula IV' and the quinoline N-oxide of Formula IV to provide the compound of Formula IIIa. In the compound of Formula IV' the group R represents an appropriate carboxylic acid protecting group (i.e. the group Pg within the protected acid group C(O)O-Pg as described previously), typically a lower alkyl such as methyl, ethyl or t-butyl or a group such as benzyl, para-methoxybenzyl or diphenylmethylene. The N-oxide of Formula IV is typically prepared by oxidation of Reaction Scheme II

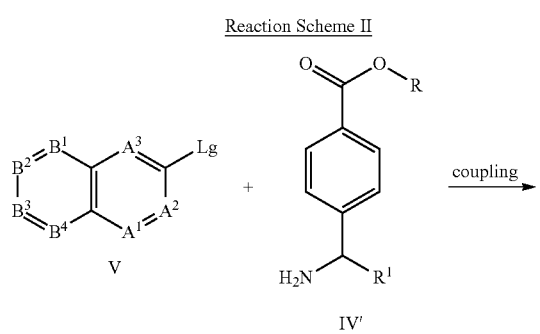

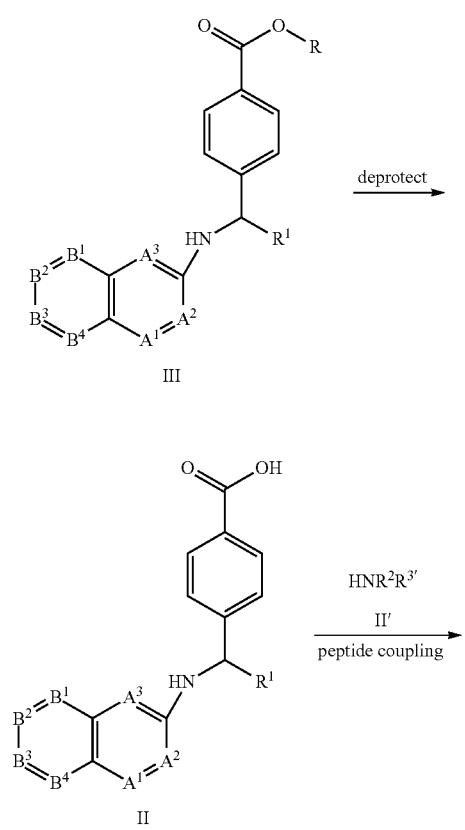

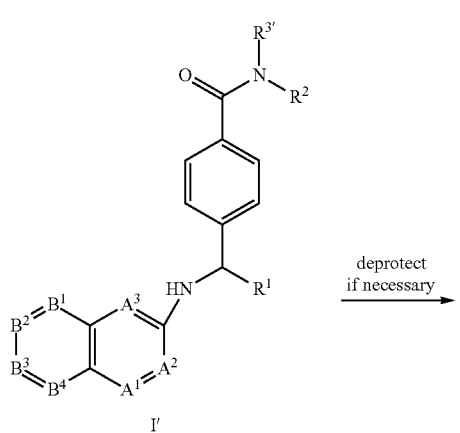

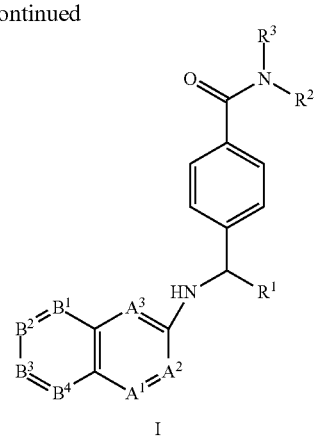

Reaction Scheme II provides another method for preparing compounds of Formula I. In step one of Reaction Scheme II the compound of Formula V and the compound of Formula IV' are coupled. In the compound of Formula V, the group Lg represents an appropriate leaving group such as a halide, mesylate or triflate. In the compound of Formula IV' the group R represents an appropriate carboxylic acid protecting group, typically a lower alkyl such as methyl, ethyl or t-butyl or a group such as benzyl, para-methoxybenzyl or diphenyl-methylene. The coupling reaction between compounds V and IV' can be carried out under a variety of conditions. For example, the compound of formula V can be coupled with compound IV' using palladium catalyzed aryl amination reaction conditions such as those described by Buchwald, S.; et al. in J. Am. Chem. Soc., 2008, 130(21), 6686-6687; J. Am. Chem. Soc., 2008, 130(41), 13552-13554 and J. Am. Chem. Soc., 2010, 132(45), 15914-15917. The palladium catalyzed coupling can be carried out using 2-(Dicyclohexylphosphino)-3,6-dimethoxy-2'-4'-6'-tri-i-propyl-1,1'-biphenyl (Brettphos) as ligand and Chloro[2-(dicyclohexylphosphino)-3,6-dimethoxy-2'-4'-6'-tri-i-propyl-1,1'-biphenyl][2-(2-aminoethyl)phenyl]palladium(II) (Brettphos palladacycle) as the precatalyst. The reaction can be carried out in an appropriate solvent such as dioxane at room temperature up to 100° C. for a period of 1 to 24 hours followed by workup to provide the compound of Formula III. The ester compound of Formula III can then be deprotected to provide the free acid compound of Formula II which can then be subjected to a peptide coupling reaction with the amine $R^{3'}R^2NH$, followed by deprotection if necessary to provide the compound of Formula I. The group $R^{3'}$ in the amine $R^{3'}R^2NH$ can represent either $R^3$ itself or a protected version of $R^3$ which can be subsequently deprotected as needed to provide $R^3$.

Reaction Scheme III

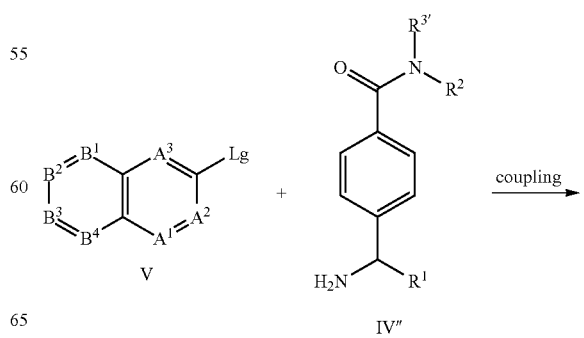

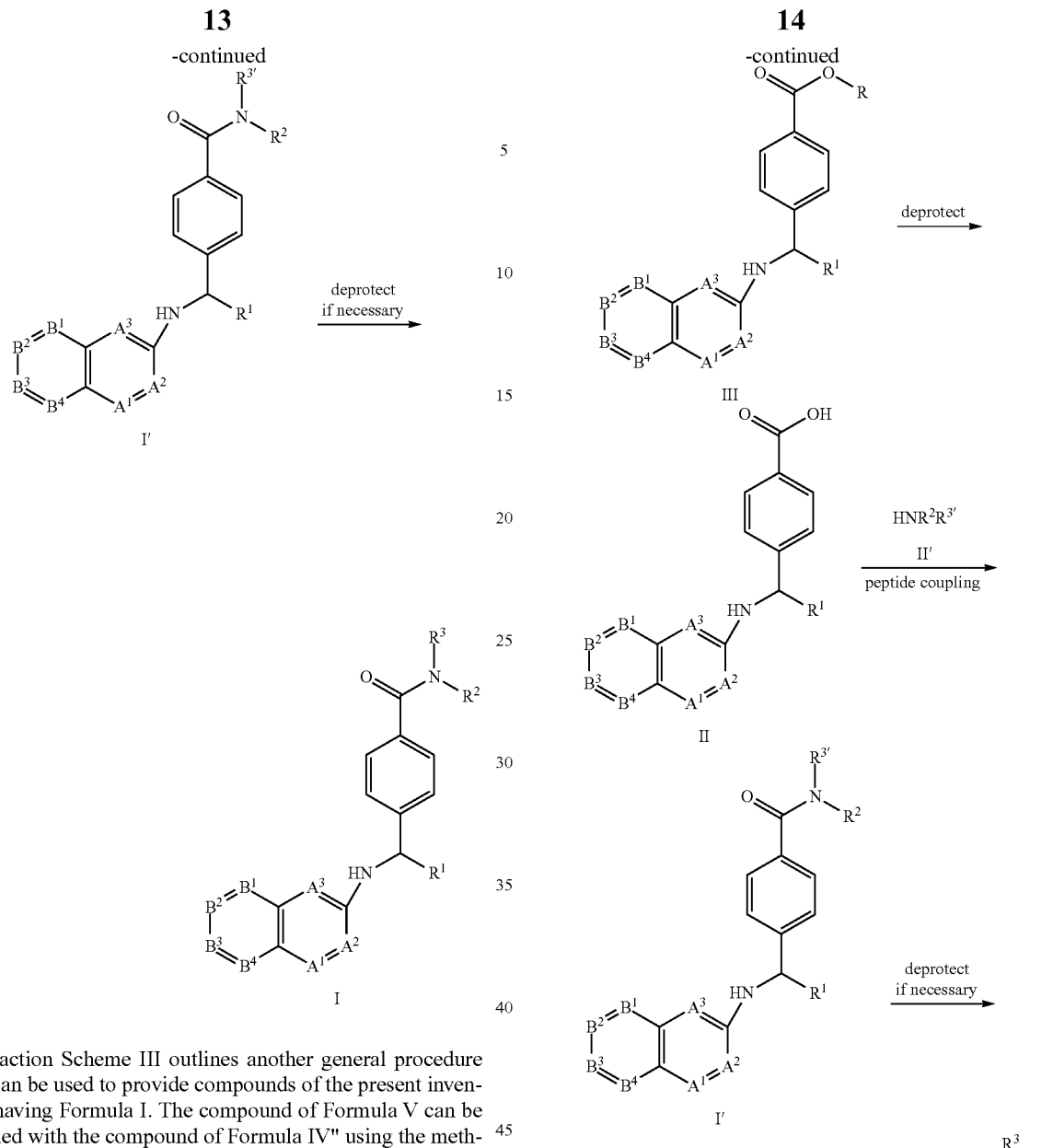

Reaction Scheme III outlines another general procedure that can be used to provide compounds of the present invention having Formula I. The compound of Formula V can be coupled with the compound of Formula IV" using the methods as previously described in the first step of Reaction Scheme II to provide the compound of Formula I'. The compound of Formula I' can then be deprotected as necessary as previously described to provide the compound of formula I.

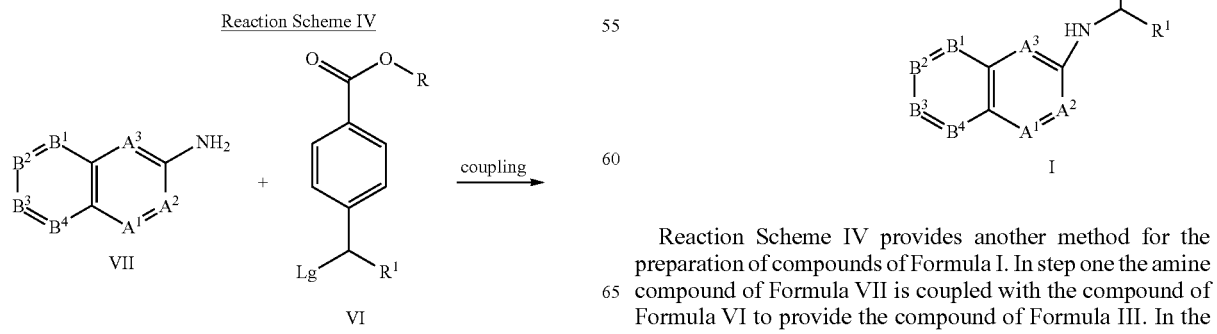

Reaction Scheme IV provides another method for the preparation of compounds of Formula I. In step one the amine compound of Formula VII is coupled with the compound of Formula VI to provide the compound of Formula III. In the compound of Formula VI the group Lg represents an appropriate leaving group such as a mesylate, triflate or halide. The nucleophilic substitution reaction between compounds VII and VI is typically carried out in an appropriate solvent such as acetonitrile in the presence of an appropriate base, such as potassium carbonate or potassium phosphate within a temperature range of ambient temperature to 80° C. for a period of one to twenty four hours. In certain cases the the group Lg in the compound of Formula VI can also represent a carbonyl oxygen atom and the amine of Formula VII can then be reacted with it under typical reductive amination conditions to provide the compound of of Formula III. The compound of Formula III can then be sequentially converted to compounds of Formulae II, I' and I as previously described for Reaction Scheme I.

The compounds of the present invention may be isolated and used per se, or when possible, in the form of its pharmaceutically acceptable salt. The term "salts" refers to inorganic and organic salts of a compound of the present invention. These salts can be prepared in situ during the final isolation and purification of a compound, or by separately reacting the compound with a suitable organic or inorganic acid or base and isolating the salt thus formed. Representative salts include the hydrobromide, hydrochloride, hydroiodide, sulfate, bisulfate, nitrate, acetate, trifluoroacetate, oxalate, besylate, palmitiate, pamoate, malonate, stearate, laurate, malate, borate, benzoate, lactate, phosphate, hexafluorophosphate, benzene sulfonate, tosylate, formate, citrate, maleate, fumarate, succinate, tartrate, naphthylate, mesylate, glucoheptonate, lactobionate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, e.g., Berge, et al., *J. Pharm. Sci.*, 66, 1-19 (1977).

The compounds of the present invention may contain asymmetric or chiral centers, and, therefore, exist in different stereoisomeric forms. Unless specified otherwise, it is intended that all stereoisomeric forms of the compounds of the present invention as well as mixtures thereof, including racemic mixtures, form part of the present invention. In addition, the present invention embraces all geometric isomers. For example, if a compound of the present invention incorporates a double bond or a fused ring, both the cis- and trans-forms, as well as mixtures, are embraced within the scope of the invention.

Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column. Alternatively, the specific stereoisomers may be synthesized by using an optically active starting material, by asymmetric synthesis using optically active reagents, substrates, catalysts or solvents, or by converting one stereoisomer into the other by asymmetric transformation.

It is also possible that the intermediates and compounds of the present invention may exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. A specific example of a proton tautomer is the imidazole moiety where the proton may migrate between the two ring nitrogens. Valence tautomers include interconversions by reorganization of some of the bonding electrons.

Certain compounds of the present invention may exist in different stable conformational forms which may be separable. Torsional asymmetry due to restricted rotation about an asymmetric single bond, for example, because of steric hindrance or ring strain, may permit separation of different conformers.

The present invention also embraces isotopically-labeled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, sulfur, fluorine, iodine, and chlorine, such as $^{2}$H, $^{3}$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{123}$I, $^{125}$I and $^{36}$Cl, respectively.

Certain isotopically-labeled compounds of the present invention (e.g., those labeled with $^{3}$H and $^{14}$C) are useful in compound and/or substrate tissue distribution assays. Tritiated (i.e., $^{3}$H) and carbon-14 (i.e., $^{14}$C) isotopes are particularly preferred for their ease of preparation and detectability. Further, substitution with heavier isotopes such as deuterium (i.e., $^{2}$H) may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C, and $^{18}$F are useful for positron emission tomography (PET) studies to examine substrate occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

Certain compounds of the present invention may exist in more than one crystal form (generally referred to as "polymorphs"). Polymorphs may be prepared by crystallization under various conditions, for example, using different solvents or different solvent mixtures for recrystallization; crystallization at different temperatures; and/or various modes of cooling, ranging from very fast to very slow cooling during crystallization. Polymorphs may also be obtained by heating or melting the compound of the present invention followed by gradual or fast cooling. The presence of polymorphs may be determined by solid probe NMR spectroscopy, IR spectroscopy, differential scanning calorimetry, powder X-ray diffraction or such other techniques.

Compounds of the present invention are useful for treating diseases, conditions and/or disorders modulated by glucagon; therefore, another embodiment of the present invention is a pharmaceutical composition comprising a therapeutically effective amount of a compound of the present invention and a pharmaceutically acceptable excipient, diluent or carrier. The compounds of the present invention (including the compositions and processes used therein) may also be used in the manufacture of a medicament for the therapeutic applications described herein.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients described above. The compound of the present invention is typically formulated into pharmaceutical dosage forms to provide an easily controllable dosage of the drug and to give the patient an elegant and easily handleable product.

The pharmaceutical compositions also include solvates and hydrates of the compounds of Formula I. The term "solvate" refers to a molecular complex of a compound represented by Formula I (including pharmaceutically acceptable salts thereof) with one or more solvent molecules. Such solvent molecules are those commonly used in the pharmaceutical art, which are known to be innocuous to the recipient, e.g., water, ethanol, ethylene glycol, and the like, The term "hydrate" refers to the complex where the solvent molecule is water. The solvates and/or hydrates preferably exist in crystalline form. Other solvents may be used as intermediate solvates in the preparation of more desirable solvates, such as methanol, methyl t-butyl ether, ethyl acetate, methyl acetate, (S)-propylene glycol, (R)-propylene glycol, 1,4-butyne-diol, and the like.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The present invention further provides a method of treating diseases, conditions and/or disorders modulated by glucagon in an animal that includes administering to an animal in need of such treatment a therapeutically effective amount of a compound of the present invention or a pharmaceutical composition comprising an effective amount of a compound of the present invention and a pharmaceutically acceptable excipient, diluent, or carrier. The method is particularly useful for treating diseases, conditions and/or disorders that benefit from the modulation of glucagon which include: diabetes, eating disorders (e.g., binge eating disorder, anorexia, bulimia, weight loss or control and obesity), prevention of obesity and insulin resistance.

One aspect of the present invention is the treatment of obesity, and obesity-related disorders (e.g., overweight, weight gain, or weight maintenance).

Obesity and overweight are generally defined by body mass index (BMI), which is correlated with total body fat and estimates the relative risk of disease. BMI is calculated by weight in kilograms divided by height in meters squared ($kg/m^2$). Overweight is typically defined as a BMI of 25-29.9 $kg/m^2$, and obesity is typically defined as a BMI of 30 $kg/m^2$. See, e.g., National Heart, Lung, and Blood Institute, Clinical Guidelines on the Identification, Evaluation, and Treatment of Overweight and Obesity in Adults, The Evidence Report, Washington, D.C.: U.S. Department of Health and Human Services, NIH publication no. 98-4083 (1998).

Another aspect of the present invention is for the treatment or delaying the progression or onset of diabetes or diabetes-related disorders including Type 1 (insulin-dependent diabetes mellitus, also referred to as "IDDM") and Type 2 (noninsulin-dependent diabetes mellitus, also referred to as "NIDDM") diabetes, impaired glucose tolerance, insulin resistance, hyperglycemia, and diabetic complications (such as atherosclerosis, coronary heart disease, stroke, peripheral vascular disease, nephropathy, hypertension, neuropathy, and retinopathy).

Yet another aspect of the present invention is the treatment of diabetes- or obesity-related co-morbidities, such as metabolic syndrome. Metabolic syndrome includes diseases, conditions or disorders such as dyslipidemia, hypertension, insulin resistance, diabetes (e.g., Type 2 diabetes), weight gain, coronary artery disease and heart failure. For more detailed information on Metabolic Syndrome, see, e.g., Zimmet, P. Z., et al., "The Metabolic Syndrome: Perhaps an Etiologic Mystery but Far From a Myth—Where Does the International Diabetes Federation Stand?," *Diabetes & Endocrinology,* 7(2), (2005); and Alberti, K. G., et al., "The Metabolic Syndrome—A New Worldwide Definition," *Lancet,* 366, 1059-62 (2005). Preferably, administration of the compounds of the present invention provides a statistically significant ($p<0.05$) reduction in at least one cardiovascular disease risk factor, such as lowering of plasma leptin, C-reactive protein (CRP) and/or cholesterol, as compared to a vehicle control containing no drug. The administration of compounds of the present invention may also provide a statistically significant ($p<0.05$) reduction in glucose serum levels.

In yet another aspect of the present invention, the condition treated is impaired glucose tolerance, hyperglycemia, diabetic complications such as sugar cataracts, diabetic neuropathy, diabetic nephropathy, diabetic retinopathy and diabetic cardiomyopathy, anorexia nervosa, bulimia, cachexia, hyperuricemia, hyperinsulinemia, hypercholesterolemia, hyperlipidemia, dyslipidemia, mixed dyslipidemia, hypertriglyceridemia, nonalcoholic fatty liver disease, atherosclerosis, arteriosclerosis, acute heart failure, congestive heart failure, coronary artery disease, cardiomyopathy, myocardial infarction, angina pectoris, hypertension, hypotension, stroke, ischemia, ischemic reperfusion injury, aneurysm, restenosis, vascular stenosis, solid tumors, skin cancer, melanoma, lymphoma, breast cancer, lung cancer, colorectal cancer, stomach cancer, esophageal cancer, pancreatic cancer, prostate cancer, kidney cancer, liver cancer, bladder cancer, cervical cancer, uterine cancer, testicular cancer and ovarian cancer.

The present invention also relates to therapeutic methods for treating the above described conditions in a mammal, including a human, wherein a compound of Formula I of this invention is administered as part of an appropriate dosage regimen designed to obtain the benefits of the therapy. The appropriate dosage regimen, the amount of each dose administered and the intervals between doses of the compound will depend upon the compound of formula (I) of this invention being used, the type of pharmaceutical compositions being used, the characteristics of the subject being treated and the severity of the conditions.

In general, an effective dosage for the compounds of the present invention is in the range of 0.01 mg/kg/day to 30 mg/kg/day, preferably 0.01 mg/kg/day to 5 mg/kg/day of active compound in single or divided doses. However, some variability in the general dosage range may be required depending upon the age and weight of the subject being treated, the intended route of administration, the particular compound being administered and the like. The determination of dosage ranges and optimal dosages for a particular patient is well within the ability of one of ordinary skill in the art having the benefit of the instant disclosure. Practitioners will appreciate that "kg" refers to the weight of the patient measured in kilograms.

The compounds or compositions of this invention may be administered in single (e.g., once daily) or multiple doses or via constant infusion. The compounds of this invention may also be administered alone or in combination with pharmaceutically acceptable carriers, vehicles or diluents, in either single or multiple doses. Suitable pharmaceutical carriers, vehicles and diluents include inert solid diluents or fillers, sterile aqueous solutions and various organic solvents.

The compounds or compositions of the present invention may be administered to a subject in need of treatment by a variety of conventional routes of administration, including orally and parenterally, (e.g., intravenously, subcutaneously or intramedullary). Further, the pharmaceutical compositions of this invention may be administered intranasally, as a suppository, or using a "flash" formulation, i.e., allowing the medication to dissolve in the mouth without the need to use water.

It is also noted that the compounds of the present invention can be used in sustained release, controlled release, and delayed release formulations, which forms are also well known to one of ordinary skill in the art.

The compounds of this invention may also be used in conjunction with other pharmaceutical agents for the treatment of the diseases, conditions and/or disorders described herein. Therefore, methods of treatment that include administering compounds of the present invention in combination with other pharmaceutical agents are also provided. Suitable pharmaceutical agents that may be used in combination with the compounds of the present invention include anti-obesity agents (including appetite suppressants), anti-diabetic agents, anti-hyperglycemic agents, lipid lowering agents, and anti-hypertensive agents.

Suitable anti-diabetic agents include an acetyl-CoA carboxylase-(ACC) inhibitor such as those described in WO2009144554, WO2003072197, WO2009144555 and WO2008065508, a diacylglycerol O-acyltransferase 1 (DGAT-1) inhibitor, such as those described in WO09016462 or WO2010086820, AZD7687 or LCQ908, diacylglycerol O-acyltransferase 2 (DGAT-2) inhibitor, monoacylglycerol O-acyltransferase inhibitors, a phosphodiesterase (PDE)-10 inhibitor, an AMPK activator, a sulfonylurea (e.g., acetohexamide, chlorpropamide, diabinese, glibenclamide, glipizide, glyburide, glimepiride, gliclazide, glipentide, gliquidone, glisolamide, tolazamide, and tolbutamide), a meglitinide, an α-amylase inhibitor (e.g., tendamistat, trestatin and AL-3688), an α-glucoside hydrolase inhibitor (e.g., acarbose), an α-glucosidase inhibitor (e.g., adiposine, camiglibose, emiglitate, miglitol, voglibose, pradimicin-Q, and salbostatin), a PPARγ agonist (e.g., balaglitazone, ciglitazone, darglitazone, englitazone, isaglitazone, pioglitazone, rosiglitazone and troglitazone), a PPAR α/γ agonist (e.g., CLX-0940, GW-1536, GW-1929, GW-2433, KRP-297, L-796449, LR-90, MK-0767 and SB-219994), a biguanide (e.g., metformin), a glucagon-like peptide 1 (GLP-1) modulator such as an agonist (e.g., exendin-3 and exendin-4), liraglutide, albiglutide, exenatide (Byetta®), albiglutide, taspoglutide, lixisenatide, dulaglutide, semaglutide, NN-9924, TTP-054, a protein tyrosine phosphatase-1B (PTP-1B) inhibitor (e.g., trodusquemine, hyrtiosal extract, and compounds disclosed by Zhang, S., et al., *Drug Discovery Today,* 12(9/10), 373-381 (2007)), SIRT-1 inhibitor (e.g., resveratrol, GSK2245840 or GSK184072), a dipeptidyl peptidease IV (DPP-IV) inhibitor (e.g., those in WO2005116014, sitagliptin, vildagliptin, alogliptin, dutogliptin, linagliptin and saxagliptin), an insulin secreatagogue, a fatty acid oxidation inhibitor, an A2 antagonist, a c-jun amino-terminal kinase (JNK) inhibitor, glucokinase activators (GKa) such as those described in WO2010103437, WO2010103438, WO2010013161, WO2007122482, TTP-399, TTP-355, TTP-547, AZD1656, ARRY403, MK-0599, TAK-329, AZD5658 or GKM-001, insulin, an insulin mimetic, a glycogen phosphorylase inhibitor (e.g. GSK1362885), a VPAC2 receptor agonist, SGLT2 inhibitors, such as those described in E. C. Chao et al. Nature Reviews Drug Discovery 9, 551-559 (July 2010) including dapagliflozin, canagliflozin, BI-10733, tofogliflozin (CSG452), ASP-1941, THR1474, TS-071, ISIS388626 and LX4211 as well as those in WO2010023594, a glucagon receptor modulator such as those described in Demong, D. E. et al. Annual Reports in Medicinal Chemistry 2008, 43, 119-137, GPR119 modulators, particularly agonists, such as those described in WO2010140092, WO2010128425, WO2010128414, WO2010106457, Jones, R. M. et al. in Medicinal Chemistry 2009, 44, 149-170 (e.g. MBX-2982, GSK1292263, APD597 and PSN821), FGF21 derivatives or analogs such as those described in Kharitonenkov, A. et al. et al., Current Opinion in Investigational Drugs 2009, 10(4)359-364, TGR5 (also termed GPBAR1) receptor modulators, particularly agonists, such as those described in Zhong, M., Current Topics in Medicinal Chemistry, 2010, 10(4), 386-396 and INT777, GPR40 agonists, such as those described in Medina, J. C., Annual Reports in Medicinal Chemistry, 2008, 43, 75-85, including but not limited to TAK-875, GPR120 modulators, particularly agonists, high affinity nicotinic acid receptor (HM74A) activators, and SGLT1 inhibitors, such as GSK1614235, and SGLT2 inhibitors such as (1S,2S,3S,4R, 5S)-5-[4-chloro-3-(4-ethoxy-benzyl)-phenyl]-1-hydroxymethyl-6,8-dioxa-bicyclo[3.2.1]octane-2,3,4-triol, sergliflozin, remogliflozin, dapagliflozin, canagliflozin, TA-7284, YM543, BI10773. A further representative listing of anti-diabetic agents that can be combined with the compounds of the present invention can be found, for example, at page 28, line 35 through page 30, line 19 of WO2011005611. Preferred anti-diabetic agents are metformin and DPP-IV inhibitors (e.g., sitagliptin, vildagliptin, alogliptin, dutogliptin, linagliptin and saxagliptin) and SGLT2 inhibitors. Other antidiabetic agents could include inhibitors or modulators of carnitine palmitoyl transferase enzymes, inhibitors of fructose 1,6-diphosphatase, inhibitors of aldose reductase, mineralocorticoid receptor inhibitors, inhibitors of TORC2, inhibitors of CCR2 and/or CCR5, inhibitors of PKC isoforms (e.g. PKCα, PKCβ, PKCγ), inhibitors of fatty acid synthetase, inhibitors of serine palmitoyl transferase, modulators of GPR81, GPR39, GPR43, GPR41, GPR105, Kv1.3, retinol binding protein 4, glucocorticoid receptor, somatostain receptors (e.g. SSTR1, SSTR2, SSTR3 and SSTR5), inhibitors or modulators of PDHK2 or PDHK4, inhibitors of MAP4K4, modulators of IL1 family including IL1 beta, modulators of RXRalpha. In addition suitable anti-diabetic agents include mechanisms listed by Carpino, P. A., Goodwin, B. Expert Opin. Ther. Pat, 2010, 20(12), 1627-51.

Suitable anti-obesity agents (some of which may also act as anti-diabetic agents as well) include 11β-hydroxy steroid dehydrogenase-1 (11β-HSD type 1) inhibitors, stearoyl-CoA desaturase-1 (SCD-1) inhibitor, MCR-4 agonists, cholecystokinin-A (CCK-A) agonists, monoamine reuptake inhibitors (such as sibutramine), sympathomimetic agents, $\beta_3$ adrenergic agonists, dopamine agonists (such as bromocriptine), melanocyte-stimulating hormone analogs, 5HT2c agonists, melanin concentrating hormone antagonists, leptin (the OB protein), leptin analogs, leptin agonists, galanin antagonists, lipase inhibitors (such as tetrahydrolipstatin, i.e. orlistat), anorectic agents (such as a bombesin agonist), neuropeptide-Y antagonists (e.g., NPY Y5 antagonists such as velneperit), $PYY_{3-36}$ (including analogs thereof), BRS3 modulator, mixed antagonists of opiod receptor subtypes, thyromimetic agents, dehydroepiandrosterone or an analog thereof, glucocorticoid agonists or antagonists, orexin antagonists, glucagon-like peptide-1 agonists, ciliary neurotrophic factors (such as Axokine™ available from Regeneron Pharmaceuticals, Inc., Tarrytown, N.Y. and Procter & Gamble Company, Cincinnati, Ohio), human agouti-related protein (AGRP) inhibitors, histamine 3 antagonists or inverse agonists, neuromedin U agonists, MTP/ApoB inhibitors (e.g., gut-selective MTP inhibitors, such as dirlotapide, JTT130, Usistapide, SLx4090), opioid antagonist, mu opioid receptor modulators, including but not limited to GSK1521498, MetAp2 inhibitors, including but not limited to ZGN-433, agents with mixed modulatory activity at 2 or more of glucagon, GIP and GLP1 receptors, such as MAR-701 or ZP2929, norepinephrine transporter inhibitors, cannabinoid-1-receptor antagonist/inverse agonists, ghrelin agonists/antagonists, oxyntomodulin and analogs, monoamine uptake inhibitors, such as but not limited to tesofensine, an orexin antagonist, combination agents (such as bupropion plus zonisamide, pramlintide plus metreleptin, bupropion plus naltrexone, phentermine plus topiramate), and the like.

Preferred anti-obesity agents for use in the combination aspects of the present invention include gut-selective MTP inhibitors (e.g., dirlotapide, mitratapide and implitapide, R56918 (CAS No. 403987) and CAS No. 913541-47-6), CCKa agonists (e.g., N-benzyl-2-[4-(1H-indol-3-ylmethyl)-5-oxo-1-phenyl-4,5-dihydro-2,3,6,10b-tetraaza-benzo[e]azulen-6-yl]-N-isopropyl-acetamide described in PCT Publication No. WO 2005/116034 or US Publication No. 2005-0267100 A1), 5HT2c agonists (e.g., lorcaserin), MCR4 agonist (e.g., compounds described in U.S. Pat. No. 6,818, 658), lipase inhibitor (e.g., Cetilistat), $PYY_{3-36}$ (as used herein "$PYY_{3-36}$" includes analogs, such as peglated $PYY_{3-36}$ e.g., those described in US Publication 2006/0178501), opioid antagonists (e.g., naltrexone), oleoyl-estrone (CAS No. 180003-17-2), obinepitide (TM30338), pramlintide (Symlin®), tesofensine (NS2330), leptin, bromocriptine, orlistat, AOD-9604 (CAS No. 221231-10-3) and sibutramine. Preferably, compounds of the present invention and combination therapies are administered in conjunction with exercise and a sensible diet.

All of the above recited U.S. patents and publications are incorporated herein by reference.

Embodiments of the present invention are illustrated by the following Examples. It is to be understood, however, that the embodiments of the invention are not limited to the specific details of these Examples, as other variations thereof will be known, or apparent in light of the instant disclosure, to one of ordinary skill in the art.

EXAMPLES

Unless specified otherwise, starting materials are generally available from commercial sources such as Aldrich Chemicals Co. (Milwaukee, Wis.), Lancaster Synthesis, Inc. (Windham, N.H.), Acros Organics (Fairlawn, N.J.), Maybridge Chemical Company, Ltd. (Cornwall, England), Tyger Scientific (Princeton, N.J.), and AstraZeneca Pharmaceuticals (London, England).

General Experimental Procedures

NMR spectra were recorded on a Varian Unity™ 400 (available from Varian Inc., Palo Alto, Calif.) at room temperature at 400 MHz for proton. Chemical shifts are expressed in parts per million (δ) relative to residual solvent as an internal reference. The peak shapes are denoted as follows: s, singlet; d, doublet; dd, doublet of doublet; t, triplet; q, quartet; m, multiplet; bs, broad singlet; 2s, two singlets. Atmospheric pressure chemical ionization mass spectra (APCI) were obtained on a Fisons™ Platform II Spectrometer (carrier gas: acetonitrile: available from Micromass Ltd, Manchester, UK). Chemical ionization mass spectra (CI) were obtained on a Hewlett-Packard™ 5989 instrument (ammonia ionization, PBMS: available from Hewlett-Packard Company, Palo Alto, Calif.). Electrospray ionization mass spectra (ES) were obtained on a Waters™ ZMD instrument (carrier gas: acetonitrile: available from Waters Corp., Milford, Mass.). High resolution mass spectra (HRMS) were obtained on an Agilent™ Model 6210 using time of flight method. Where the intensity of chlorine or bromine-containing ions are described, the expected intensity ratio was observed (approximately 3:1 for $^{35}Cl/^{37}Cl$-containing ions and 1:1 for $^{79}Br/^{81}Br$-containing ions) and the intensity of only the lower mass ion is given. In some cases only representative $^1H$ NMR peaks are given. Optical rotations were determined on a PerkinElmer™ 241 polarimeter (available from PerkinElmer Inc., Wellesley, Mass.) using the sodium D line (λ=589 nm) at the indicated temperature and are reported as follows $[\alpha]_D^{temp}$, concentration (c=g/100 ml), and solvent.

Column chromatography was performed with either Baker™ silica gel (40 μm; J. T. Baker, Phillipsburg, N.J.) or Silica Gel 50 (EM Sciences™, Gibbstown, N.J.) in glass columns or in Flash 40 Biotage™ columns (ISC, Inc., Shelton, Conn.) or Biotage™ SNAP cartridge KPsil or Redisep Rf silica (from Teledyne™ ISCO™) under low nitrogen pressure. Chiral SFC (supercritical fluid chromatography) was performed on the chiral columns as specified. The following abbreviations may appear herein: BSA, bovine serum albumin; cAMP, cyclic adenosine monophosphate; CsOAc, cesium acetate; DCM, dichloromethane; DIEA, diisopropylethylamine; DMEM-F12, Dulbecco's Modified Eagle Medium Nutrient Mixture F-12; DMF, N,N-dimethylformamide; DMSO, dimethylsulfoxide; EtOAc, ethyl acetate; EtOH, ethanol; g, gram; h, hour; IBMX, 3-isobutyl-1-methylxanthine; i-PrOH, isopropanol; L, liter; LCMS, liquid chromatography mass spectrometry; MeOH, methanol; mg, milligram; mL, milliliter; mmol, millimole; min, minute; N, normal; PVT, polyvinyl toluene; RT, room temperature; SPA, scintillation proximity assay; TEA, triethylamine; THF, tetrahydrofuran; and WGA, wheat germ agglutinin.

Preparation of Starting Materials and Intermediates

Intermediate 1

Ethyl 4-butyrylbenzoate

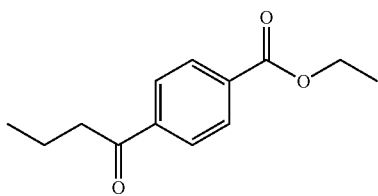 [SMILES: CCCC(=O)c1ccc(C(=O)OCC)cc1]

At −40° C., isopropylmagnesium chloride lithium chloride (15.3 mL, 1.3 M in THF, 19.9 mmol) was added dropwise to a solution of ethyl 4-iodobenzoate (5000 mg, 18.11 mmol) in tetrahydrofuran (30 mL). The solution was stirred at −40° C. for 40 minutes. Butyraldehyde (1830 mg, 25.4 mmol) was added. The mixture was allowed to warm to room temperature over 3 hours. The reaction was quenched with 1N HCl and extracted three times with ethyl acetate. The combined organic layers were dried over sodium sulfate, filtered and concentrated to give ethyl 4-(1-hydroxybutyl)benzoate. $^1$H NMR (400 MHz, CDCl$_3$) δ 8.02 (d, J=8.6 Hz, 2H), 7.41 (d, J=8.0 Hz, 2H), 4.83-4.66 (m, 1H), 4.38 (q, J=7.2 Hz, 2H), 1.86 (d, J=3.7 Hz, 1H), 1.83-1.61 (m, 2H), 1.51-1.42 (m, 1H), 1.39 (t, J=7.2 Hz, 3H), 1.36-1.23 (m, 1H), 0.94 (t, J=7.6 Hz, 3H).

A mixture of the crude alcohol (1.0 g, 4.5 mmol) in dichloromethane (16.7 mL), dimethylsulfoxide (4.79 mL) and triethylamine (2.28 g, 22.5 mmol) was cooled to 0° C. Sulfur trioxide pyridine complex (2.15 g, 13.5 mmol) was added in portions and the mixture stirred at 0° C. for 1 hour. The reaction was then allowed to warm to room temperature and stir for 2 hours. The reaction was quenched with brine and diluted with dichloromethane. The layers were separated and the aqueous was extracted again with dichloromethane. The combined organic layers were dried over sodium sulfate, filtered and concentrated. Purification by column chromatography (0-30% ethyl acetate in heptane) gave ethyl 4-butyrylbenzoate (Intermediate 1). $^1$H NMR (400 MHz, CDCl$_3$) δ 8.05-8.17 (m, 2 H), 8.04-7.92 (m, 2 H), 4.40 (q, J=7.15 Hz, 2 H), 2.96 (t, J=7.22 Hz, 2 H), 1.86-1.69 (m, 2 H), 1.40 (t, J=7.12 Hz, 3 H), 1.00 (t, J=7.22 Hz, 3 H).

Intermediate 2

Ethyl (+/−)-4-(1-aminobutyl)benzoate

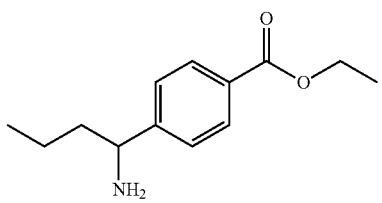 [SMILES: CCCC(N)c1ccc(C(=O)OCC)cc1]

Sodium cyanoborohydride (29.8 g, 0.450 mol) was added to a solution of Intermediate 1 (66.1 g, 0.300 mol) and ammonium acetate (236 g, 3.00 mol) in methanol (1000 mL). The solution was fitted with a reflux condenser and heated to 60° C. for 16 h. The solution was allowed to cool to room temperature. The reaction was quenched by dropwise addition of 1N HCl (300 mL) and allowed to stir at room temperature for 1 h. The reaction mixture was concentrated to remove methanol. This mixture was diluted by careful addition of 1N NaOH (500 mL) followed by extraction with dichloromethane (3×500 mL). The combined organic layers were dried over sodium sulfate, filtered and concentrated. Purification by silica gel flash chromatography (methanol/dichloromethane) gave ethyl (+/−)-4-(1-aminobutyl)benzoate (Intermediate 2). $^1$H NMR (400 MHz, CDCl$_3$) δ 8.01 (d, J=8.2 Hz, 2 H), 7.40 (d, J=8.2 Hz, 2 H), 4.38 (q, J=7.2 Hz, 2 H), 3.98 (t, J=6.9 Hz, 1 H), 1.95 (br. s., 2 H), 1.74-1.56 (m, 2 H), 1.40 (t, J=7.1 Hz, 3 H), 1.16-1.37 (m, 2 H), 0.91 (t, J=7.4 Hz, 3 H).

Intermediate 3

3-Methylquinoline 1-oxide

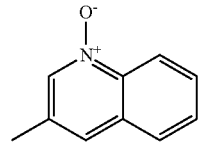

3-Methylquinoline (30.0 mL, 224 mmol) was dissolved in acetic acid (85 mL), and 30% aqueous hydrogen peroxide (30.4 mL) was added. The reaction was stirred at 80° C. for 16 h before cooling in an ice bath. 10% aq Na$_2$SO$_3$ (199 mL, 0.5 equiv) was added followed by sodium iodide (2.358 g, 0.05 equiv). This mixture was stirred for 5 min. A peroxide test strip indicated no peroxide remaining. 5 N aq NaOH was then added, keeping the internal temperature below 24° C. A dark color formed, indicating that the solution was basic (tested as pH 10). The solution was extracted with four portions of dichloromethane. The combined organics were dried over MgSO$_4$ and filtered, and the filtrate was concentrated under reduced pressure. Purification by silica gel flash chromatography (methanol/ethyl acetate) gave 3-methylquinoline 1-oxide (Intermediate 3, 32.09 g) as a yellow solid. $^1$H NMR (400 MHz, CDCl$_3$) δ 8.69 (d, J=8.8 Hz, 1 H), 8.42 (s, 1 H), 7.77 (d, J=8.2 Hz, 1 H), 7.68 (td, J=7.8, 1.1 Hz, 1 H), 7.56-7.63 (m, 1 H), 7.52 (s, 1 H), 2.45 (s, 3 H); MS (M+1): 160.2.

Intermediate 4

Ethyl (+/−)-4-(1-((3-methylquinolin-2-yl)amino)butyl)benzoate

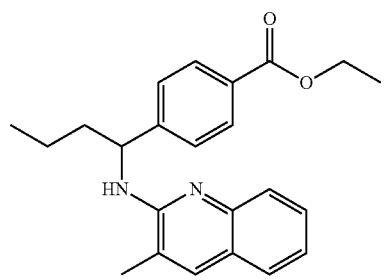 [SMILES: CCCC(Nc1nc2ccccc2cc1C)c1ccc(C(=O)OCC)cc1]

Intermediate 2 (22.9 g, 104 mmol) was combined with 3-methylquinoline-N-oxide (Intermediate 3, 17.3 g, 109 mmol) and dichloromethane (414 mL). Diisopropylethylamine (68.0 mL, 389 mmol) was added, followed by bromotripyrrolidinophosphonium hexafluorophosphate (61.0 g, 130 mmol). The solution was stirred at room temperature for 12 h before diluting with sat. aq NaHCO$_3$ (400 mL). The mixture was extracted with ethyl acetate (3×400 mL). The combined organics were dried over Na$_2$SO$_4$ and filtered, and the filtrate was concentrated under reduced pressure. Purification by silica gel flash chromatography (ethyl acetate/heptane) gave ethyl (+/−)-4-(1-((3-methylquinolin-2-yl)amino) butyl)benzoate (Intermediate 4). $^1$H NMR (400 MHz, CDCl$_3$) δ 7.99 (d, J=8.2 Hz, 2 H), 7.65-7.58 (m, 2 H), 7.56-7.48 (m, 3 H), 7.43 (t, J=7.5 Hz, 1 H), 7.16 (t, J=7.4 Hz, 1 H), 5.50 (q, J=7.2 Hz, 1 H), 4.79 (d, J=7.0 Hz, 1 H), 4.35 (q, J=7.0 Hz, 2 H), 2.30 (s, 3 H), 2.04-1.83 (m, 2 H), 1.54-1.39 (m, 2 H), 1.37 (t, J=7.1 Hz, 3 H), 0.98 (t, J=7.4 Hz, 3 H).

Intermediate 5

(+/−)-4-(1-((3-Methylquinolin-2-yl)amino)butyl) benzoic acid

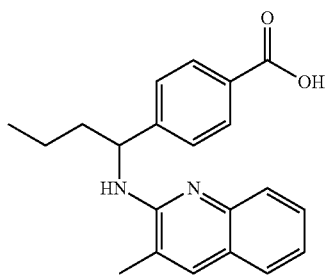 [SMILES: CCCC(Nc1nc2ccccc2cc1C)c1ccc(C(=O)O)cc1]

To a solution of Intermediate 4 (34.29 g, 94.60 mmol) in tetrahydrofuran (234 mL) and methanol (234 mL) was added 1 N aq sodium hydroxide (473 mL). The solution was stirred at room temperature for 16 h. The solution was concentrated under reduced pressure to remove tetrahydrofuran and methanol. 3 N aqueous hydrochloric acid was added dropwise to pH 2. The resulting slurry was filtered, and the solid was washed with water (300 mL, then 100 mL). The solid was dried by azeotropic removal of water first with toluene, then heptane (7×100 mL), followed by heating to 70° C. under reduced pressure to afford (+/−)-4-(1-((3-methylquinolin-2-yl) amino)butyl)benzoic acid (Intermediate 5). $^1$H NMR (400 MHz, CD$_3$OD) δ 8.09 (s, 1 H), 8.02 (d, J=8.4 Hz, 2 H), 7.84 (d, J=8.4 Hz, 1 H), 7.72 (d, J=7.8 Hz, 1 H), 7.66-7.58 (m, 3 H), 7.40 (t, J=7.6 Hz, 1 H), 5.56 (dd, J=6.0, 8.6 Hz, 1 H), 2.49 (s, 3 H), 2.24-2.10 (m, 1 H), 2.08-1.95 (m, 1 H), 1.66-1.52 (m, 1 H), 1.52-1.39 (m, 1 H), 1.03 (t, J=7.4 Hz, 3 H).

Intermediate 6

Methyl (+)-3-(4-(1-((3-methylquinolin-2-yl)amino) butyl)benzamido)propanoate and Intermediate 7: Methyl (−)-3-(4-(1-((3-methylquinolin-2-yl)amino) butyl)benzamido)propanoate

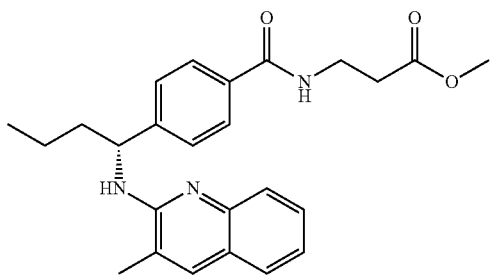

Intermediate 5 (31.64 g, 94.61 mmol), β-alanine ethyl ester hydrochloride (45.9 g, 284 mmol), and 1-hydroxybenzotriazole hydrate (80%, 20 wt % water, 47.9 g, 284 mmol) were suspended in dichloromethane (946 mL). Triethylamine (119 mL, 852 mmol) followed by N-(3-dimethylaminopropyl)-N'-ethylcarbodiimide hydrochloride (46.0 g, 237 mmol) were added, and the solution was stirred at room temperature for 10 h. The reaction mixture was washed with water (3×900 mL), then sat. aq NaCl (300 mL). The organic layer was dried over Na$_2$SO$_4$ and filtered, and the filtrate was concentrated under reduced pressure. Purification by silica gel flash chromatography (ethyl acetate/heptane) followed by chiral SFC (Chiralpak AD-H column, 30×250, 20% methanol/carbon dioxide eluent, 0.2% isopropylamine modifier) gave methyl (+)-3-(4-(1-((3-methylquinolin-2-yl)amino)butyl)benzamido)propanoate (Intermediate 6, analytical chiral SFC 4.6 min retention) and methyl (−)-3-(4-(1-((3-methylquinolin-2-yl)amino) butyl)benzamido)propanoate (Intermediate 7, analytical chiral SFC 6.5 min retention)—note that ethyl ester was converted to methyl ester during the reaction and/or purification sequence. $^1$H NMR (400 MHz, CDCl$_3$) δ 7.71 (d, J=8.4 Hz, 2H), 7.64-7.58 (m, 2 H), 7.55-7.48 (m, 3 H), 7.44 (t, J=7.7 Hz, 1 H), 7.16 (t, J=7.4 Hz, 1 H), 6.76 (t, J=5.5 Hz, 1 H), 5.48 (q, J=7.2 Hz, 1 H), 4.78 (d, J=7.0 Hz, 1 H), 3.76 (q, J=6.0 Hz, 2 H), 3.70 (s, 3 H), 2.64 (t, J=5.9 Hz, 2 H), 2.29 (s, 3 H), 2.04-1.82 (m, 2 H), 1.52-1.29 (m, 2 H), 0.98 (t, J=7.3 Hz, 3 H).

Intermediate 8

(+/−)-4-(1-hydroxy-3-methyl-butyl)-benzoic acid ethyl ester

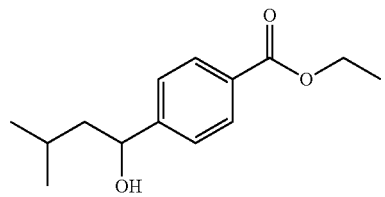 [SMILES: CCOC(=O)c1ccc(C(O)CC(C)C)cc1]

To a solution of ethyl 4-iodobenzoate (140 g, 507 mmol) in tetrahydrofuran at −40° C. was added Isopropylmagnesium chloride lithium chloride complex solution (1.0 M in tetrahydrofuran, 429 mL, 558 mmol) dropwise at a rate to maintain the internal temperature below −30° C. The mixture was stirred for 30 minutes at which point isobutyraldehyde (61 g, 710 mmol) was added dropwise while maintaining the temperature below −35° C. The mixture was stirred at this temperature for 15 minutes and then slowly warmed to room temperature. The reaction was quenched with 1N HCl (3 L) and the mixture extracted with ethyl acetate (2 L×2). The combined organics were washed with brine (1 L) and water (1 L), and then dried over anhydrous Na$_2$SO$_4$. This was concentrated in vacuo to give (+/−)-4-(1-hydroxy-3-methyl-butyl)-

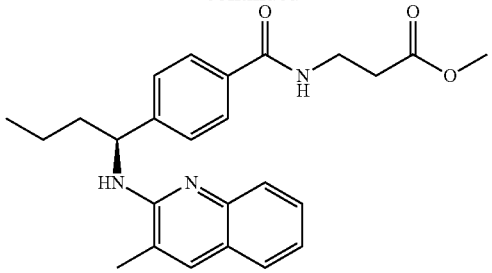

benzoic acid ethyl ester (120 g, 100%) as an oil. $^1$H NMR (400 MHz, CDCl$_3$) δ 7.95 (d, J=8.4 Hz, 2 H), 7.47 (s, J=7.2 Hz, 2 H), 4.76-4.73 (m, 1 H), 4.33-4.28 (m, 2 H), 1.71-1.60 (m, 2 H), 1.46-1.41 (m, 1 H), 1.39-1.31 (m, 3 H), 0.92-0.87 (m, 6 H).

Intermediate 9

(+/−)-4-(1-hydroxy-3-methyl-butyl)-benzoic acid

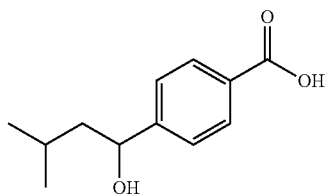

To a solution of Intermediate 8 (15 g, 63 mmol) in tetrahydrofuran (63.5 mL) was added 2 N NaOH (63.5 mL). The resulting mixture was stirred at room temperature for 2 h and then at 60° C. overnight. The mixture was acidified with 1 N HCl to pH 4 and then extracted with ethyl acetate (3×50 mL). The combined organic layers were dried over anhydrous Na$_2$SO$_4$, filtered and concentrated under reduced pressure to give (+/−)-4-(1-hydroxy-3-methyl-butyl)-benzoic acid (11 g, 83%) as a yellow solid. $^1$H NMR (400 MHz, CD$_3$OD) δ 8.06 (d, J=8.4 Hz, 2 H), 7.51 (d, J=8.4 Hz, 2 H), 4.81 (q, J=8.4 Hz, 5.2 Hz, 1 H), 1.81-1.71 (m, 2 H), 1.55-1.51 (m, 1 H), 1.03 (q, J=6.4 Hz, 2.4 Hz, 6 H).

Intermediate 10

(+/−)-3-[4-(1-hydroxy-3-methyl-butyl)-benzoylamino]-propionic acid tert-butyl ester

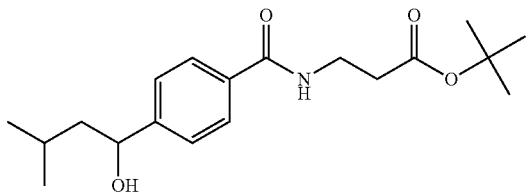 [SMILES: CC(C)CC(O)c1ccc(C(=O)NCCC(=O)OC(C)(C)C)cc1]

To a solution of the Intermediate 9 (9.5 g, 46 mmol) in DMF (120 mL) was added HATU (34.7 g, 91.2 mmol) at room temperature. The mixture was stirred for 20 min and beta-alanine tert-butyl ester (13.2 g, 91.2 mmol) and diisopropylethylamine (35.4 g, 274 mmol) were slowly added to the reaction mixture at 0° C. The resulting mixture was stirred at room temperature for 1.5 h before adding ethyl acetate (50 mL) and brine (100 mL). The separated aqueous layer was extracted with ethyl acetate (4×50 mL) and the combined organic layers were washed with brine (50 mL), dried over anhydrous Na$_2$SO$_4$, filtered and concentrated under reduced pressure to give crude compound (40 g) as a brown oil. Purification by silica gel flash chromatography (ethyl acetate/petroleum ether) gave (+/−)-3-[4-(1-hydroxy-3-methyl-butyl)-benzoylamino]-propionic acid tert-butyl ester (14 g, 90%) as a yellow solid. $^1$H NMR (400 MHz, CD$_3$OD) δ 7.84 (d, J=8.4 Hz, 2 H), 7.50 (d, J=8.4 Hz, 2 H), 4.80 (dd, J=8.4 Hz, 5.6 Hz, 1 H), 3.67 (t, J=7.2 Hz, 2 H), 2.64 (t, J=5.6 Hz, 2 H), 1.78-1.72 (m, 2 H), 1.55-1.52 (m, 1 H), 1.50 (s, 9 H), 1.02 (d, J=6.4 Hz, 6 H).

Intermediate 11

(+/−)-3-{4-[1-(1,3-dioxo-1,3-dihydro-isoindol-2-yl)-3-methyl-butyl]-benzoylamino}-propionic acid tert-butyl ester

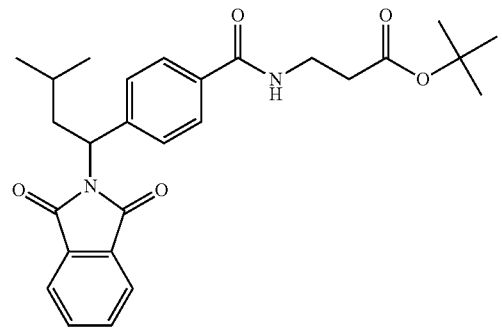 [SMILES: CC(C)CC(c1ccc(C(=O)NCCC(=O)OC(C)(C)C)cc1)N1C(=O)c2ccccc2C1=O]

To a solution of Intermediate 10 (14 g, 42 mmol), phthalimide (12.3 g, 83.5 mmol) and PPh$_3$ (21.9 g, 83.5 mmol) in tetrahydrofuran was added diisopropyl azodicarboxylate (16.9 g, 83.5 mmol) at 0° C. The resulting mixture was stirred at room temperature overnight before adding water (60 mL) and ethyl acetate (50 mL). The aqueous layers were extracted with ethyl acetate (3×50 mL) and the combined organic extracts were dried over Na$_2$SO$_4$, filtered and concentrated in vacuo to give crude (+/−)-3-{4-[1-(1,3-dioxo-1,3-dihydro-isoindol-2-yl)-3-methyl-butyl]-benzoylamino}-propionic acid tert-butyl ester (26 g) as a yellow oil. The crude compound was used in the next step directly.

Intermediate 12

(+/−)-3-[4-(1-amino-3-methyl-butyl)-benzoylamino]-propionic acid tert-butyl ester

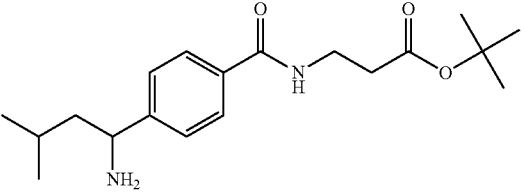 [SMILES: CC(C)CC(N)c1ccc(C(=O)NCCC(=O)OC(C)(C)C)cc1]

To a solution of crude Intermediate 11 (26 g, 26 mmol) in ethanol (100 mL) was added hydrazine hydrate (30 mL). The reaction mixture was heated to reflux and stirred overnight. After cooling, water (100 mL) and ethyl acetate (50 mL) were added, the layers separated, and the aqueous layer was extracted with ethyl acetate (3×75 mL). The combined organic extracts were dried over Na$_2$SO$_4$, filtered and concentrated in vacuo to give crude compound (20 g) as a yellow oil. Purification by silica gel flash chromatography (methanol/dichloromethane) gave (+/−)-3-[4-(1-amino-3-methyl-butyl)-benzoylamino]-propionic acid tert-butyl ester (6.8 g, 79%) as a yellow solid. $^1$H NMR (400 MHz, CDCl$_3$) δ 7.72 (d, J=8.0 Hz, 2 H), 7.38 (d, J=8.0 Hz, 2 H), 6.87 (s, 1 H), 4.01 (t, J=6.8 Hz, 1 H), 3.69 (t, J=6.0 Hz, 2 H), 2.55 (t, J=6.0 Hz, 2 H), 2.05-1.81 (m, 2 H), 1.59-1.48 (m, 3 H), 1.46 (s, 9 H), 0.94-0.89 (m, 6 H); MS (M+23): 357.3.

Intermediate 13

(E)-methyl 3-(2-amino-4-(trifluoromethyl)phenyl) acrylate

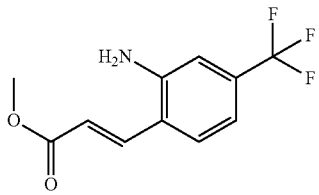 [SMILES: COC(=O)/C=C/c1ccc(C(F)(F)F)cc1N]

A 100 ml 3-neck flask with magnetic stirrer was charged with 2-bromo-5-(trifluoromethyl)aniline (500 mg, 2.08 mmol), methyl acrylate (538 mg, 6.25 mmol), Pd(OAc)$_2$ (23.3 mg, 0.104 mmol), P(o-tolyl)$_3$ (64 mg, 0.21 mmol), triethylamine (422 mg, 4.7 mmol) and acetonitrile (20 mL). The flask was purge with N$_2$ and heated to 90° C. overnight. Saturated aqueous NH$_4$Cl (40 mL) was added, and the mixture was extracted with ethyl acetate (10 mL×3). The combined organic layers were dried over Na$_2$SO$_4$, filtered and concentrated under reduce pressure. The crude product was purified by silica gel chromatography to give (E)-methyl 3-(2-amino-4-(trifluoromethyl)phenyl)acrylate (180.9 mg, 37%) as a light green solid. $^1$H NMR (400 MHz, CDCl$_3$): δ 7.71 (d, J=16 Hz, 1H), δ 7.38 (d, J=8 Hz, 1H), δ 6.92 (d, J=8 Hz, 1H), δ 6.86 (s, 1H), δ 6.34 (d, J=8 Hz, 1H), δ 4.05 (s, 2H), δ 3.73 (s, 3H).

Intermediate 14

7-(trifluoromethyl)quinolin-2-ol

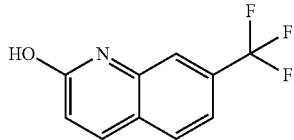 [SMILES: Oc1ccc2ccc(C(F)(F)F)cc2n1]

A 100 mL flask equipped with magnetic stirrer was charged with Intermediate 13 (600 mg, 2.44 mmol), concentrated aqueous HCl (893 mg), THF (6 mL) and water (6 mL). The mixture was heated at reflux overnight. The mixture was extracted with ethyl acetate (3×10 mL). The organic layer was dried over Na$_2$SO$_4$, filtered, and evaporated to dryness. The crude residue was purified by silica gel chromatography to give 7-(trifluoromethyl)quinolin-2-ol (440 mg, 84.3%) as a green solid. $^1$H NMR (400 MHz, DMSO-d$_6$) δ 12.56 (s, 1H), 7.99 (d, J=15.6 Hz, 1 H), 7.81 (d, J=8 Hz, 1H), 7.20 (s, 1H), 6.97 (d, J=8 Hz, 1H), 6.59 (d, J=15.6 Hz, 1H).

Intermediate 15

2-chloro-7-(trifluoromethyl)quinoline

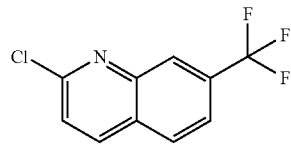 [SMILES: FC(F)(F)c1ccc2ccc(Cl)nc2c1]

A 50 mL round-bottom flask equipped with magnetic stirrer was charged with Intermediate 14 (100 mg, 0.47 mmol) and POCl$_3$ (5 mL). The mixture was heated to reflux for 3 hours. The POCl$_3$ was removed under reduce pressure and saturated aqueous NaHCO$_3$ (20 mL) was added. The mixture was extracted with ethyl acetate (3×10 mL). The organic layer was dried over Na$_2$SO$_4$, filtered and concentrated under reduced pressure. The crude product was purified by silica gel chromatography to give 2-chloro-7-(trifluoromethyl)quinoline (27.7 mg, 25.4%) as a yellow solid. $^1$H NMR (400 MHz, MeOD): δ 8.35 (d, J=8.8 Hz, 1H), 8.16 (s, 1H), δ 8.08 (d, J=8.4 Hz, 1H), δ 7.75 (d, J=8.4 Hz, 1H), δ 7.57 (d, J=8.8 Hz, 1H).

Intermediate 16

(E)-methyl 3-(2-amino-5-(trifluoromethyl)phenyl) acrylate

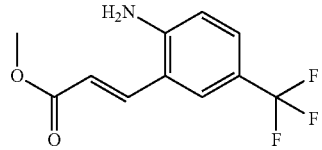 [SMILES: COC(=O)/C=C/c1cc(C(F)(F)F)ccc1N]

A 100 ml 3-neck flask with magnetic stirrer was charged with 2-bromo-4-(trifluoromethyl)aniline (500 mg, 2.08 mmol), methyl acrylate (538 mg, 6.25 mmol), Pd(OAc)$_2$ (23.3 mg, 0.104 mmol), P(o-tolyl)$_3$ (64 mg, 0.21 mmol), triethylamine (422 mg, 4.7 mmol) and acetonitrile (20 ml). The flask was purged with N$_2$ and heated to 90° C. overnight. Saturated aqueous NH$_4$Cl (40 ml) was added, and the mixture was extracted with ethyl acetate (10 ml*3). The organic layer was dried over Na$_2$SO$_4$, filtered, and concentrated to dryness. The crude product was purified by silica gel chromatography to give (E)-methyl 3-(2-amino-5-(trifluoromethyl)phenyl) acrylate (185.9 mg, 36.5%) as a yellow solid. $^1$H NMR (400 MHz, CDCl$_3$) δ 7.69 (d, J=16 Hz, 1H), 7.53 (s, 1H), 7.32 (d, J=8.8 Hz, 1H), 6.67 (d, J=8.8 Hz, 1H), 6.34 (d, J=16 Hz, 1H), 4.20 (s, 2H), 3.74 (s, 3H).

Intermediate 17

2-chloro-6-(trifluoromethyl)quinoline

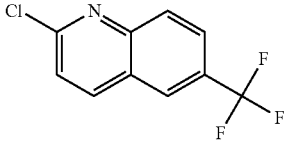 [SMILES: FC(F)(F)c1ccc2nc(Cl)ccc2c1]

A 100 mL flask equipped with magnetic stirrer was charged with Intermediate 16 (740 mg, 3.02 mmol), concentrated aqueous HCl (3.1 mL), THF (7 mL) and water (7 mL). The mixture was heated at reflux overnight. the mixture was extracted with ethyl acetate (3×10 mL). The combined organic layers were dried over Na$_2$SO$_4$, filtered, and evaporated to give 560 mg of a yellow solid. The crude residue was dissolved in POCl$_3$ (20 mL). The mixture was heated to reflux for 3 hours. The POCl$_3$ was removed underreduced pressure and saturated aqueous NaHCO$_3$ (40 mL) was added. The solution was extracted with ethyl acetate (3×15 mL). The combined organic layers were dried over Na$_2$SO$_4$, filtered, and concentrated to dryness. The crude product was purified by silica gel chromatography to give 2-chloro-6-(trifluoromethyl)quinoline (438 mg, 63%) as a colorless solid. $^1$H NMR (400 MHz, CDCl$_3$) δ 8.14 (d, J=8.4 Hz, 1H), 8.08-8.06 (m, 2H), 7.85-7.90 (m, 1H), 7.44 (d, J=8.4 Hz, 1H).

Intermediate 18

3-amino-2-methylquinoline

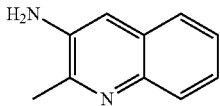

A solution of 2-methyl-3-nitroquinoline (400 mg, 2.13 mmol) in conc. HCl (8 mL) was heated to 50° C. Tin (II) chloride dihydrate (1.2 g, 5.3 mmol) was added. The mixture was stirred at 50° C. overnight. The mixture was diluted with water (20 mL). The pH was brought to 9 by addition of aqueous 5 N NaOH. The mixture was cooled to 4° C. and extracted with ethyl acetate (2×30 mL). The combined extracts were washed with ice-cold water (40 mL) and dried over anhydrous Na$_2$SO$_4$, filtered, and concentrated to give 3-amino-2-methylquinoine (270 mg, 80%) as a yellow solid. 1H NMR (400 MHz, CDCl3): δ 7.84 (d, J=8.4 Hz, 1H), 7.51 (dd, J=1.2, 8.0 Hz, 1H), 7.39-7.30 (m, 2H), 7.16 (s, 1H), 3.77 (s, 2H), 2.56 (s, 3H).

Intermediate 19 ethyl 4-(3-methyl-1-(methylsulfonyloxy)butyl)benzoate

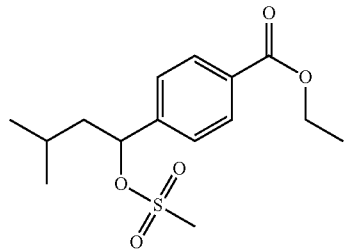 [SMILES: CCOC(=O)c1ccc(C(CC(C)C)OS(C)(=O)=O)cc1]

To a 0° C. solution of Intermediate 8 (350 mg, 1.48 mmol) in anhydrous dichloromethane (20 mL) was added triethylamine (449.4 mg, 16.7 mmol), followed by methanesulfonyl chloride (186.8 mg, 1.63 mmol). The resulting mixture was stirred at 0° C. for 1 h and room temperature for 30 min. The reaction mixture was quenched with water (10 mL) and extracted with ethyl acetate (3×10 mL). The combined organic layers were dried over Na$_2$SO$_4$, filtered, and concentrated under reduced pressure to give ethyl 4-(3-methyl-1-(methylsulfonyloxy)butyl)benzoate (180 mg, 39%) as an oil containing some triethylammonium hydrochloride. This material was used without further purification. $^1$HNMR (400 MHz, CDCl$_3$) δ 8.01 (d, J=8.0 Hz, 2H), 7.40 (d, J=8.0 Hz, 2H), 5.56 (m, 1H), 4.32 (q, J=7.2 Hz, 2H), 2.01-1.92 (m, 1H), 1.69-1.51 (m, 2H), 1.31-1.40 (m, 3H, overlaps with triethylammonium hydrochloride peak), 0.89-0.95 (m, 6H).

Intermediate 20

3-amino-4-methylquinoline

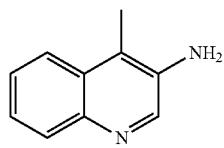

A solution of 4-methyl-3-nitroquinoline (500 mg, 2.66 mmol) in conc. HCl (10 mL) was heated to 50° C. Tin (II) chloride dihydrate (1.5 g, 6.6 mmol) was added. The mixture was stirred at 50° C. overnight. The mixture was diluted with water (20 mL). The mixture was adjusted to pH 9 by addition of 5N aqueous sodium hydroxide. The mixture was cooled to 4° C. and extracted twice with ethyl acetate (30 mL). The combined extracts were washed with ice-cold water (40 mL) and dried over anhydrous Na$_2$SO$_4$, filtered, and concentrated to give 3-amino-4-methylquinoline (340 mg, 80%) as a yellow solid. $^1$H NMR (400 MHz, CDCl$_3$) δ 8.42 (s, 1H), 7.89-7.91 (m, 1H), 7.79-7.82 (m, 1H), 7.44-7.38 (m, 2H), 3.77 (br s, 2H), 2.37 (s, 3H).

Intermediate 21 ethyl 4-(3-methyl-1-(4-methylquinolin-3-ylamino)butyl)benzoate

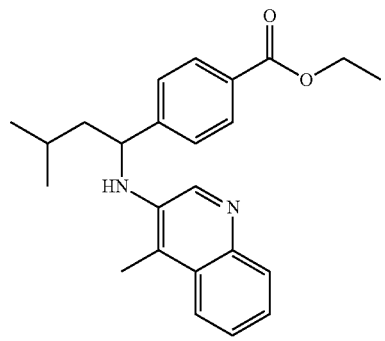 [SMILES: CCOC(=O)c1ccc(C(CC(C)C)Nc2cnc3ccccc3c2C)cc1]

A mixture of Intermediate 20 (200 mg, 1.26 mmol), Intermediate 19 (476 mg) and potassium carbonate (349 mg, 2.53 mmol) in acetonitrile (10 mL) was stirred at 80° C. overnight. The reaction mixture was poured into brine (20 mL) and extracted with ethyl acetate (30 mL×2). The combined organic layers were washed with brine (30 mL×2) and water (30 mL), then dried over anhydrous Na$_2$SO$_4$, filtered, and concentrated under reduced pressure. Purification by silica gel chromatography provided ethyl 4-(3-methyl-1-(4-methylquinolin-3-ylamino)butyl)benzoate (40 mg, 10%) as a yellow solid. $^1$H NMR (400 MHz, CDCl$_3$) δ 8.23 (s, 1H), 7.91 (d, J=8.4 Hz, 2H), 7.86 (d, J=8.0 Hz, 1H), 7.80 (d, J=8.0 Hz, 1H), 7.42-7.33 (m, 4H), 4.62-4.65 (m, 1H), 4.27 (q, J=7.2 Hz, 2H), 2.44 (s, 3H), 1.78-1.70 (m, 1H), 1.68-1.64 (m, 2H), 1.17 (q, J=7.2 Hz, 3H), 0.97 (d, J=6.4 Hz, 3H), 0.90 (d, J=6.4 Hz, 3H).

Intermediate 22

3,3-dimethylcyclobutanecarbonyl chloride

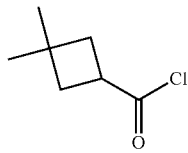

3,3-Dimethyl-cyclobutanecarboxylic acid (Parkway Scientific, New York, N.Y., USA) (500 mg, 3.90 mmol) was dissolved in dichloromethane (3 mL) and oxalyl chloride (1.02 mL, 11.7 mmol) was added. The solution was stirred at room temperature for 4 h before concentrating in vacuo to provide 3,3-dimethylcyclobutanecarbonyl chloride which was carried on without purification. $^1$H NMR (400 MHz, CDCl$_3$) δ 3.49 (quin, J=8.9 Hz, 1 H) 2.15-2.27 (m, 2 H) 2.06-2.14 (m, 2 H) 1.18 (s, 3 H) 1.12 (s, 3 H).

Intermediate 23

4-(3,3-dimethyl-cyclobutanecarbonyl)-benzoic acid ethyl ester

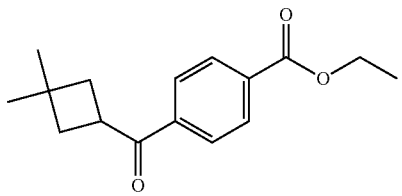 [SMILES: CCOC(=O)c1ccc(C(=O)C2CC(C)(C)C2)cc1]

Ethyl 4-iodobenzoate (600 mg, 2.17 mmol) was dissolved in tetrahydrofuran (6.0 mL) and brought to −40° C. Isopropylmagnesium chloride lithium chloride complex solution (1.0 M in tetrahydrofuran, 0.365 mL, 2.17 mmol) was added dropwise and the yellow-red solution was stirred at −40° C. for 40 min. CuI (124 mg, 0.65 mmol) was added in one portion and the mixture was then stirred at −15° C. for 20 min to dissolve all the solids. The yellow solution was then brought back to −40° C. and 3,3-dimethylcyclobutanecarbonyl chloride (Intermediate 22) (450 mg, 3.07 mmol) was added dropwise. The color changed from slightly green to yellow, then red, then yellow. The mixture was warmed to 0° C. over 2 h in the same bath. The mixture was diluted with 1 N HCl and extracted with ethyl acetate (3 times). The combined organic layers were washed with brine, dried over Na$_2$SO$_4$, and concentrated in vacuo. The crude material was partially purified by silica gel flash chromatography (ethyl acetate/heptane) to give impure 4-(3,3-dimethyl-cyclobutanecarbonyl)-benzoic acid ethyl ester (588 mg). $^1$H NMR (400 MHz, CDCl$_3$) δ 8.11 (d, J=8.4 Hz, 2 H) 7.94 (d, J=8.4 Hz, 2 H) 4.38-4.48 (m, 2 H) 3.90 (quin, J=8.8 Hz, 1 H) 2.16-2.29 (m, 2 H) 2.04-2.13 (m, 2 H) 1.42 (t, J=7.2 Hz, 3 H) 1.28 (s, 3 H) 1.09 (s, 3 H); MS (M+1): 261.4.

Intermediate 24

(+/−)-4-[amino-(3,3-dimethyl-cyclobutyl)-methyl]-benzoic acid ethyl ester

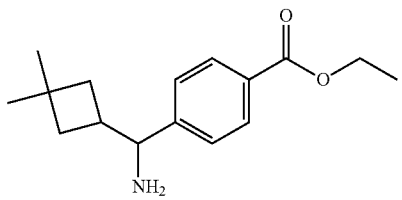 [SMILES: CCOC(=O)c1ccc(C(N)C2CC(C)(C)C2)cc1]

4-(3,3-dimethyl-cyclobutanecarbonyl)-benzoic acid ethyl ester (Intermediate 23) (235 mg, 0.903 mmol) was dissolved in methanol (5 mL). Ammonium acetate (710 mg, 9.03 mmol) was added followed by sodium cyanoborohydride (89.6 mg, 1.36 mmol). This was heated to 60° C. for 17 h before cooling and adding 1 N HCl (3 mL). This was stirred for 15 min and then 1N NaOH (10 mL) was added. The material was extracted into two portions of ethyl acetate and the combined organics dried over MgSO$_4$. Purification by silica gel flash chromatography (methanol/ethyl acetate) gave (+/−)-4-[amino-(3,3-dimethyl-cyclobutyl)-methyl]-benzoic acid ethyl ester (137 mg) as a pale yellow oil. $^1$H NMR (400 MHz, CDCl$_3$) δ 7.99 (d, J=8.4 Hz, 2 H) 7.37 (d, J=8.2 Hz, 2 H) 4.38 (q, J=7.0 Hz, 2 H) 3.82 (d, J=9.2 Hz, 1H) 2.39 (sxt, J=8.7 Hz, 1 H) 1.90-2.02 (m, 1 H) 1.60-1.70 (m, 1 H) 1.46-1.57 (m, 2 H) 1.40 (t, J=7.1 Hz, 3 H) 1.11 (s, 3 H) 1.06 (s, 3H); GCMS (M): 261.

Intermediate 25

(+/−)-4-[(3,3-dimethyl-cyclobutyl)-(3-methyl-quinolin-2-ylamino)-methyl]-benzoic acid ethyl ester

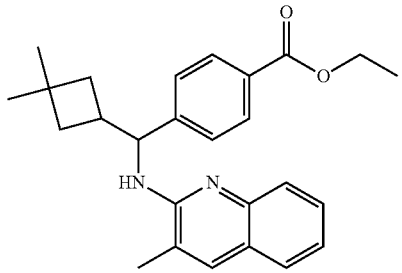 [SMILES: CCOC(=O)c1ccc(C(Nc2nc3ccccc3cc2C)C2CC(C)(C)C2)cc1]

(+/−)-4-[amino-(3,3-dimethyl-cyclobutyl)-methyl]-benzoic acid ethyl ester (Intermediate 24) (45 mg, 0.17 mmol) was combined with 3-methylquinoline-N-oxide (27.4 mg, 0.172 mmol, Alfa Aesar, Ward Hill, Mass., USA) and dichloromethane (2 mL). Diisopropylethylamine (0.112 mL, 0.645 mmol) was added followed by bromotripyrrolidinophosphonium hexafluorophosphate (109 mg, 0.224 mmol). The solution was stirred at room temperature for 28 h before partitioning between ethyl acetate and aq. sat. NaHCO$_3$. The separated aqueous layer was extracted with additional ethyl acetate and the combined organics dried over MgSO$_4$. Purification by silica gel flash chromatography (ethyl acetate/heptane) gave (+/−)-4-[(3,3-dimethyl-cyclobutyl)-(3-methyl-quinolin-2-ylamino)-methyl]-benzoic acid ethyl ester (44.0 mg) as a clear oil. $^1$H NMR (400 MHz, CDCl$_3$) δ 7.96 (d, J=8.4 Hz, 2 H) 7.56-7.62 (m, 2 H) 7.46-7.53 (m, 3 H) 7.38-7.46 (m, 1 H) 7.12-7.20 (m, 1 H) 5.33 (dd, J=9.5, 6.7 Hz, 1 H) 4.77 (d, J=6.6 Hz, 1 H) 4.34 (q, J=7.2 Hz, 2 H) 2.67 (sxt, J=8.8 Hz, 1 H) 2.30 (s, 3 H) 1.97 (ddd, J=11.1, 8.1, 3.2 Hz, 1 H) 1.74-1.85 (m, 1 H) 1.66-1.73 (m, 2 H) 1.36 (t, J=7.1 Hz, 3 H) 1.16 (s, 3 H) 1.10 (s, 3 H); MS (M+1): 403.3.

Intermediate 26

(+/−)-4-[(3,3-dimethyl-cyclobutyl)-(3-methyl-quinolin-2-ylamino)-methyl]-benzoic acid

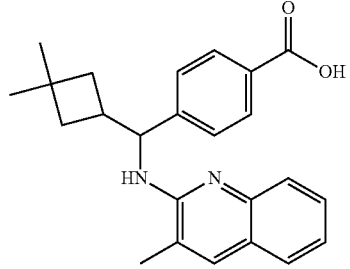 [SMILES: Cc1cc2ccccc2nc1NC(c1ccc(C(=O)O)cc1)C1CC(C)(C)C1]

(+/−)-4-[(3,3-dimethyl-cyclobutyl)-(3-methyl-quinolin-2-ylamino)-methyl]-benzoic acid ethyl ester (Intermediate 25) (43 mg, 0.11 mmol) was dissolved in tetrahydrofuran (3 mL) and methanol (1 mL), and 1.0 M NaOH (2 mL) was added. This was stirred at 50° C. at first as a suspension then as a clear solution for 4 h before cooling to room temperature. 1 N HCl was added until the solution was pH 5. This was extracted twice with ethyl acetate and the combined organics were dried over MgSO$_4$. The solution was concentrated in vacuo to give (+/−)-4-[(3,3-dimethyl-cyclobutyl)-(3-methyl-quinolin-2-ylamino)-methyl]-benzoic acid (37.7 mg) as a white solid. MS (M+1): 375.1.

Intermediate 27

(+/−)-3-{4-[(3,3-dimethyl-cyclobutyl)-(3-methyl-quinolin-2-ylamino)-methyl]-benzoylamino}-propionic acid ethyl ester

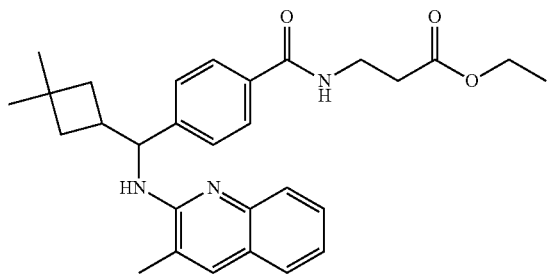 [SMILES: CCOC(=O)CCNC(=O)c1ccc(C(Nc2nc3ccccc3cc2C)C2CC(C)(C)C2)cc1]

(+/−)-4-[(3,3-dimethyl-cyclobutyl)-(3-methyl-quinolin-2-ylamino)-methyl]-benzoic acid (Intermediate 26) (37 mg, 0.099 mmol) was combined with 1-hydrobenzotriazole hydrate (23.0 mg, 0.149 mmol), N-(3-dimethylaminopropyl)-N'-ethylcarbodiimide hydrochloride (29.0 mg, 0.149 mmol), and beta-alanine ethyl ester hydrochloride (18.0 mg, 0.119 mmol). Anhydrous dichloromethane (5 mL) was added followed by triethylamine (0.027 mL, 0.198 mmol). The solution was stirred at room temperature for 3 d before partitioning between ethyl acetate and aq. sat. ammonium chloride. The separated aqueous layer was extracted with ethyl acetate and the combined organics dried over MgSO$_4$. Purification by silica gel flash chromatography (ethyl acetate/heptane) gave (+/−)-3-{4-[(3,3-dimethyl-cyclobutyl)-(3-methyl-quinolin-2-ylamino)-methyl]-benzoylamino}-propionic acid ethyl ester (37.9 mg) as a clear oil. $^1$H NMR (400 MHz, CDCl$_3$) δ 7.68 (d, J=8.2 Hz, 2 H) 7.59 (t, J=3.9 Hz, 2 H) 7.46-7.52 (m, 3 H) 7.37-7.45 (m, 1 H) 7.11-7.19 (m, 1 H) 6.75 (t, J=5.8 Hz, 1 H) 5.32 (dd, J=9.7, 6.7 Hz, 1 H) 4.75 (d, J=6.6 Hz, 1 H) 4.10-4.21 (m, 2 H) 3.70 (q, J=6.0 Hz, 2 H) 2.55-2.74 (m, 3 H) 2.29 (s, 3 H) 1.96 (ddd, J=11.1, 8.2, 2.9 Hz, 1 H) 1.75-1.84 (m, 1 H) 1.64-1.73 (m, 2 H) 1.26 (m, 3 H) 1.16 (s, 3 H) 1.09 (s, 3 H); MS (M+1): 474.7.

Intermediate 28

6-fluoro-3-methyl-quinoline

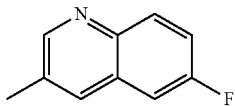

(4-Fluoro-phenyl)-carbamic acid tert-butyl ester (2.11 g, 10.0 mmol, ABCR, Karlsruhe, Germany) was added to a round bottom and purged with nitrogen. Anhydrous tetrhydrofuran (200 mL) was added to dissolve the solids and the flask placed in a dry ice/acetone bath (internal temperature −74° C. uncorrected). tert-Butyl lithium (1.7 M in pentane, 14.2 mL, 24.0 mmol) was added over 5 min causing a yellow color to develop. After the addition was complete the reaction was stirred in a −20° C. bath for 1 h. At this point, 3-ethoxymethacrolein (1.43 mL, 12.0 mmol) was added dropwise over 5 min, keeping the temperature below −19° C.

The reaction was stirred at −20° C. for 2 h before slowly adding trifluoroacetic acid (14 mL) over 5 min. The red solution was stirred at room temperature for 16 h before bring to pH 12 with 1 N NaOH. This was extracted twice with ethyl acetate and the combined organics dried over MgSO$_4$. Purification by silica gel flash chromatography (ethyle acetate/heptanes) gave impure desired material. This was extracted into three portions of 1 N HCl, the combined aqueous layers were brought to pH 12 with 6 N NaOH, and then extracted into two portions of ethyl acetate. The combined organics were dried over MgSO$_4$ and concentrated in vacuo to give 6-fluoro-3-methyl-quinoline (48.0 mg) as an orange oil. $^1$H NMR (400 MHz, CDCl$_3$) δ 8.74 (s, 1 H) 8.07 (dd, J=9.1, 5.4 Hz, 1 H) 7.88 (s, 1 H) 7.33-7.46 (m, 2 H) 2.53 (s, 3 H); MS (M+1): 162.1.

Intermediate 29

6-fluoro-3-methyl-quinoline 1-oxide

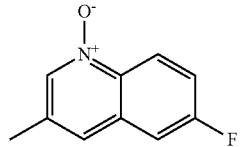

6-Fluoro-3-methyl-quinoline (Intermediate 28) (48.0 mg, 0.298 mmol) was dissolved in acetic acid (1 mL) and 30% aqueous H$_2$O$_2$ (0.040 mL, 0.396 mmol) was added. This was stirred at 80° C. for 16 h before cooling. A few mLs of a 10% aq. solution of Na$_2$SO$_3$ was added followed by a spatula tip of sodium iodide. This was stirred for 10 min before partitioning between ethyl acetate and sat. NaHCO$_3$. The separated aqueous layer was extracted with ethyl acetate and the combined organics dried over MgSO$_4$. Purification by silica gel flash chromatography (methanol/ethyl acetate) gave 6-fluoro-3-methyl-quinoline 1-oxide (29.4 mg) as a white solid. $^1$H NMR (400 MHz, CDCl$_3$) δ 8.72 (dd, J=9.4, 5.3 Hz, 1 H) 8.38 (s, 1 H) 7.36-7.50 (m, 3 H) 2.46 (s, 3 H); MS (M+1): 178.1.

Intermediate 30

3-bromo-7-fluoro-quinoline

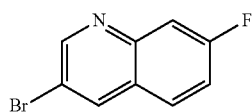

6-Fluoroindole (500 mg, 3.70 mmol) was combined with benzyltriethylammonium chloride (44.4 mg, 0.185 mmol) and toluene (0.32 mL) was added. Bromoform (0.342 mL, 3.70 mmol) was added and the temperature was brought to 40° C. A solution of NaOH (1.110 g, 7.50 mmol) in water (2.22 mL) was then added over 15 minutes. This caused a very dark color to form. The reaction was stirred as a biphasic mixture at 40° C. for 16 h before cooling and partitioning between ethyl acetate and water. The separated aqueous layer was extracted with ethyl acetate and the combined organics dried over MgSO$_4$. Purification by silica gel flash chromatography (ethyl acetate/heptane) gave 3-bromo-7-fluoro-quinoline (171.9 mg) as a white solid. $^1$H NMR (400 MHz, CDCl$_3$)

δ 8.93 (d, J=2.1 Hz, 1 H) 8.33 (d, J=2.0 Hz, 1 H) 7.68-7.82 (m, 2 H) 7.39 (td, J=8.6, 2.5 Hz, 1 H); MS (M+1): 226.0.

Intermediate 31

7-fluoro-3-methyl-quinoline

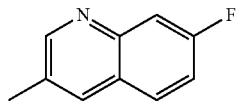

3-bromo-7-fluoro-quinoline (Intermediate 30) (100 mg, 0.442 mmol) was combined with K$_2$CO$_3$ (153 mg, 1.10 mmol), anhydrous 1,4-dioxane (3 mL), and trimethylboroxine (0.092 mL, 0.663 mmol). Nitrogen was bubbled in to degas the reaction and Pd(PPh$_3$)$_4$ (50.9 mg, 0.044 mmol) was added. This was degassed again and then heated to 90° C. for 5 h. The reaction was cooled and partitioned between ethyl acetate and sat. aq. NaHCO$_3$. The separated aqueous layer was extracted with ethyl acetate and the combined organics dried over MgSO$_4$. Purification by silica gel flash chromatography (ethyl acetate/heptane) gave 7-fluoro-3-methyl-quinoline (52.7 mg) as a yellow solid. $^1$H NMR (400 MHz, CDCl$_3$) δ 8.78 (d, J=1.8 Hz, 1 H) 7.93 (s, 1 H) 7.65-7.79 (m, 2 H) 7.32 (td, J=8.6, 2.5 Hz, 1 H) 2.52 (s, 3 H); MS (M+1): 162.1.

Intermediate 32 ethyl 4-(3,3-dimethylcyclobutanecarbonyl)benzoate

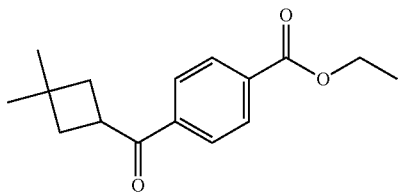 [SMILES: CCOC(=O)c1ccc(C(=O)C2CC(C)(C)C2)cc1]

In a 3-neck flask at −30° C. (monitored with thermocouple) containing ethyl 4-iodobenzoate (25.0 g, 89.0 mmol) in anhydrous tetrahydrofuran (148 mL) was added isopropylmagnesium chloride (51.0 mL, 20.4 mmol) dropwise over 30 min. and then stirred at the same temperature for another 105 min. Copper iodide (5.07 g, 26.6 mmol) was then added quickly in one portion. The mixture was brought to −20° C. for 25 min. to ensure the solid has dissolved. The reaction is then brought back to −40° C. 3,3-dimethylcyclobutanecarbonyl chloride (15.6 g, 106 mmol) was then added over 5 min. the reaction was then warmed to 0° C. over 4 h. The mixture was then diluted with 1 N HCl and extracted three times with ethyl acetate. The combined organic layers were then washed two times with brine and then dried over sodium sulfate, filtered, and concentrated to provide 26.6 g of crude brown oil. Purification by silica gel flash chromatography twice (0-5% ethyl acetate in heptane) afforded ethyl 4-(3,3-dimethylcyclobutanecarbonyl)benzoate (17.2 g, 74% yield) as an oil. $^1$H NMR (400 MHz, CDCl$_3$, δ): 8.11 (d, J=8.2 Hz, 2H), 7.93 (d, J=8.2 Hz, 2H), 4.40 (q, J=7.2 Hz, 2H), 3.89 (quin, J=8.8 Hz, 1H), 2.27-2.14 (m, 2H), 2.12-2.02 (m, 2H), 1.41 (t, J=7.1 Hz, 3H), 1.27 (s, 3H), 1.08 (s, 3H). MS (M+1): 261.2.

Intermediate 33

4-(3,3-dimethylcyclobutanecarbonyl)benzoic acid

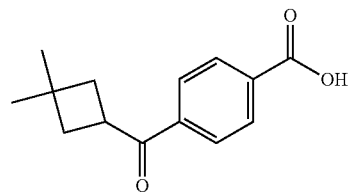 [SMILES: CC1(C)CC(C(=O)c2ccc(C(=O)O)cc2)C1]

To a flask containing ethyl 4-(3,3-dimethylcyclobutanecarbonyl)benzoate (3.00 g, 12.0 mmol) was added anhydrous tetrahydrofuran (28.8 mL), methanol (28.8 mL), and 1 N sodium hydroxide (28.8 mL, 28.8 mmol). After 1 h, the reaction was concentrated to a white solid. The solid was the redissolved in 700 mL of water. With vigorous stirring, 1 N HCl (29.0 mL) was added dropwise and the suspension was stirred for 30 min. at room temperature. The solid was then collected with a Buchner funnel and the solid was washed two times with water. The solid was then azeotrophed with toluene to give 4-(3,3-dimethylcyclobutanecarbonyl)benzoic acid (2.15 g, 92% yield) as a white solid. $^1$H NMR (400 MHz, CDCl$_3$, δ): 8.21-8.15 (m, 2H), 8.01-7.94 (m, 2H), 3.91 (quin, J=8.9 Hz, 1H), 2.28-2.17 (m, 2H), 2.15-2.04 (m, 2H), 1.28 (s, 3H), 1.09 (s, 3H). MS (M−1): 231.4.

Intermediate 34 tert-butyl 4-(3,3-dimethylcyclobutanecarbonyl)benzoate

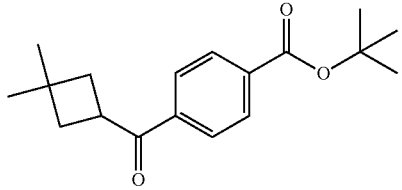 [SMILES: CC1(C)CC(C(=O)c2ccc(C(=O)OC(C)(C)C)cc2)C1]

To a flask containing 4-(3,3-dimethylcyclobutanecarbonyl)benzoic acid (1.89 g, 8.14 mmol) in anhydrous methylene chloride (20.3 mL) was added 2-tert-butyl-1,3-diisopropylurea (6.28 g, 31.3 mmol). The reaction was refluxed for 24 h. The reaction was then diluted with methylene chloride and quenched with a solution of saturated sodium bicarbonate. The aqueous layer was extracted three times with methylene chloride. The combined organic layers were washed with brine and dried with sodium sulfate, filtered, and concentrated to afford 3.09 g of a crude oil. Purification by silica gel flash chromatography (0-10% ethyl acetate in heptane) provided tert-butyl 4-(3,3-dimethylcyclobutanecarbonyl)benzoate (1.33 g, 57% yield) as a white solid. $^1$H NMR (400 MHz, CDCl$_3$, δ): 8.08-8.02 (m, 2H), 7.94-7.88 (m, 2H), 3.89

(quin, J=8.8 Hz, 1H), 2.24-2.16 (m, 2H), 2.11-2.02 (m, 2H), 1.62-1.59 (m, 9H), 1.27 (s, 3H), 1.08 (s, 3H). MS (M+1): 289.3.

Intermediate 35 tert-butyl 4-(amino(3,3-dimethylcyclobutyl)methyl)benzoate

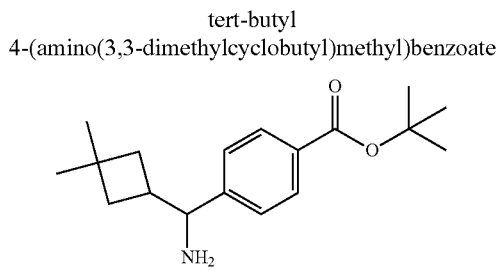

To a solution of tert-butyl 4-(3,3-dimethylcyclobutanecarbonyl)benzoate (1.46 g, 5.06 mmol) and ammonium acetate (3.98 g, 50.6 mmol) in anhydrous methanol (25.3 mL) was added sodium cyanoborohydride (502 mg, 7.60 mmol). The reaction was heated at 60° C. for 18 h. The reaction was then cooled to room temperature and 1 N hydrochloric acid (18.6 mL) was added dropwise. The clear colorless solution becomes cloudy white. The mixture is stirred for 1 h. The remaining methanol is removed and 1 N sodium hydroxide (32.0 mL) is added slowly. The mixture is extracted three times with methylene chloride. The combined organic layers are washed with brine, dried with sodium sulfate, filtered, and concentrated to give 1.62 g of an oil. Purification by silica gel flash chromatography (30-100% ethyl acetate in heptane) afforded tert-butyl 4-(amino(3,3-dimethylcyclobutyl)methyl)benzoate (860 mg, 59% yield) as an oil. $^1$H NMR (400 MHz, CDCl$_3$, δ): 7.92 (d, J=8.4 Hz, 2H), 7.34 (d, J=8.0 Hz, 2H), 3.80 (d, J=9.2 Hz, 1H), 2.45-2.30 (m, 1H), 2.01-1.88 (m, 1H), 1.68-1.60 (m, 2H), 1.60-1.56 (m, 10H), 1.48 (d, J=9.0 Hz, 2H), 1.10 (s, 3H), 1.05 (s, 3H). MS (M+1): 290.2.

Intermediate 36

3-bromo-6-fluoroquinoline

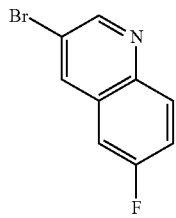 [SMILES: Fc1ccc2ncc(Br)cc2c1]

To a solution of 5-Fluoroindole (2.00 g, 14.8 mmol) and benzyltriethylammonium chloride (168.5 mg, 0.740 mmol) in toluene (3.00 mL) and bromoform (3.00 mL) at 40° C. was added a solution of sodium hydroxide (4.44 g, 111 mmol) in water (12.0 mL) in a dropwise manner. The reaction then stirred at 40° C. for 48 h. After cooling, the solvent was evaporated and the residue was diluted with methyl tert-butyl ether (100 mL) and water (100 mL). The aqueous layer was extracted with methyl tert-butyl ether. The combined organic layers were dried over sodium sulfate and concentrated under reduced pressure to give 2.00 g of crude material. Purification by silica gel flash chromatography (0-2% ethyl acetate in petroleum ether) provided 3-bromo-6-fluoroquinoline (503 mg, 15% yield) as a white solid. $^1$H NMR (400 MHz, CD$_3$OD, δ): 8.87 (d, J=2.0 Hz, 1H), 8.27 (d, J=2.0 Hz, 1H), 8.08 (dd, J=9.2, 5.6 Hz, 1H), 7.52-7.41 (m, 1H), 7.35 (dd, J=8.8, 2.8 Hz, 1H). (M+1): 225.6.

Intermediate 37 tert-butyl 4-((3,3-dimethylcyclobutyl)(7-fluoroquinolin-3-ylamino)methyl)benzoate

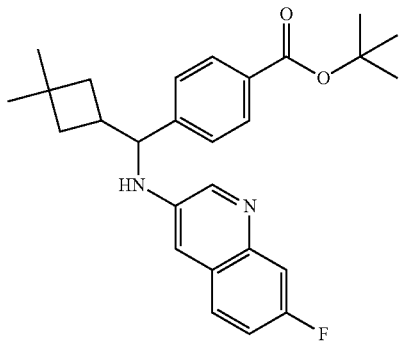 [SMILES: CC1(C)CC(C(Nc2cnc3cc(F)ccc3c2)c2ccc(C(=O)OC(C)(C)C)cc2)C1]

To a solution containing chloro(2-dicyclohexylphosphino-3,6-dimethoxy-2',4',6'-triisopropyl-1,1'-biphenyl)[2-(2-aminoethyl)phenyl]palladium(II) (11.2 mg, 0.0140 mmol) and (Intermediate 30) 3-bromo-7-fluoroquinoline (65.6 mg, 0.290 mmol) was added anhydrous tetrahydrofuran (1.00 mL) and a solution of tert-butyl 4-(amino(3,3-dimethylcyclobutyl)methyl)benzoate (80.0 mg, 0.280 mmol) in anhydrous tetrahydrofuran (0.380 mL). Lithium hexamethyldisilazide (0.690 mL, 0.690 mmol, 1 M in THF) was added dropwise. The clear, slightly yellow solution became green, yellow, then brown. The reaction was heated at 65° C. for 18 h. The reaction was then cooled to room temperature and diluted with water and extracted three times with ethyl acetate. The combined organic layers were dried with sodium sulfate, filtered, and concentrated to give 138 mg of a brown oil. Purification by silica gel flash chromatography (0-30% ethyl acetate in heptane) afforded tert-butyl 4-((3,3-dimethylcyclobutyl)(7-fluoroquinolin-3-ylamino)methyl)benzoate (12.0 mg, 10% yield) as a brown oil. $^1$H NMR (400 MHz, CDCl$_3$, δ): 8.55-8.48 (m, 1H), 7.97-7.90 (m, 2H), 7.59-7.52 (m, 1H), 7.42 (d, J=8.4 Hz, 2H), 7.40-7.33 (m, 1H), 7.14 (td, J=8.7, 2.7 Hz, 1H), 6.71 (d, J=2.7 Hz, 1H), 4.24 (dd, J=9.1, 4.2 Hz, 1H), 2.53 (q, J=8.8 Hz, 1H), 2.08-1.98 (m, 1H), 1.72 (t, J=9.7 Hz, 2H), 1.67-1.59 (m, 1H), 1.57 (s, 9H), 1.13 (s, 3H), 1.09 (s, 3H). MS (M+1): 435.3.

Intermediate 38

4-((3,3-dimethylcyclobutyl)(7-fluoroquinolin-3-ylamino)methyl)benzoic acid

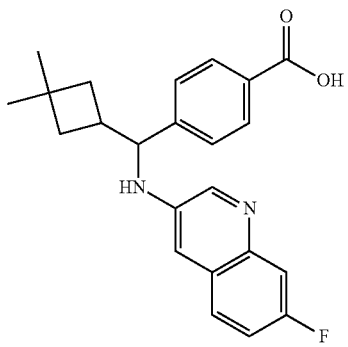 [SMILES: CC1(C)CC(C(Nc2cnc3cc(F)ccc3c2)c2ccc(C(=O)O)cc2)C1]

To a vial containing tert-butyl 4-((3,3-dimethylcyclobutyl)(7-fluoroquinolin-3-ylamino)methyl)benzoate (12.0 mg, 0.0280 mmol) was added methylene chloride (0.140 mL) and trifluoroacetic acid (0.140 mL, 0.0280 mmol). The reaction was stirred at room temperature for 1.5 h. The mixture was concentrated and azeotrophed with toluene to provide crude 4-((3,3-dimethylcyclobutyl)(7-fluoroquinolin-3-ylamino)methyl)benzoic acid (11 mg, 99% yield) as an oil. (M+1): 379.2.

Intermediate 39 ethyl 3-(4-((3,3-dimethylcyclobutyl)(7-fluoroquinolin-3-ylamino)methyl)benzamido)propanoate

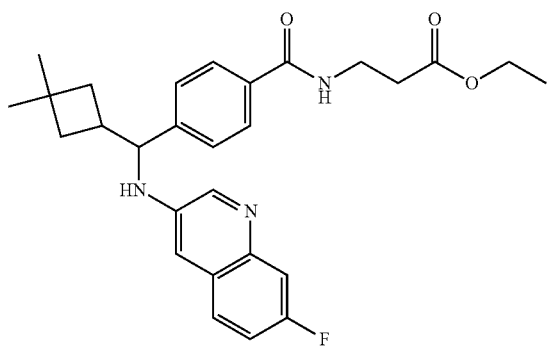 [SMILES: CCOC(=O)CCNC(=O)c1ccc(C(Nc2cnc3cc(F)ccc3c2)C2CC(C)(C)C2)cc1]

To a vial containing 4-((3,3-dimethylcyclobutyl)(7-fluoroquinolin-3-ylamino)methyl)benzoic acid (11.0 mg, 0.0290 mmol) was added 3-aminopropionic acid ethyl ester hydrochloride (4.90 mg, 0.0320 mmol), 1-Hydroxy-7-azabenzotriazole (4.80 mg, 0.0350 mmol) and 1-ethyl-3-(3-dimethylamino propyl)carbodiimide hydrochloride (6.70 mg, 0.0350 mmol). Anhydrous methylene chloride (0.290 mL) was added followed by triethylamine (0.005 mL, 0.0380 mmol). After 2 h, the reaction was diluted with methylene chloride and quenched with a saturated solution of ammonium chloride. The aqueous layer was extracted three times with methylene chloride. The combined organic layers were dried with sodium sulfate, filtered, and concentrated to give 16.0 mg of crude material. Purification by silica gel flash chromatography (0-70% ethyl acetate in heptane) provided ethyl 3-(4-((3,3-dimethylcyclobutyl)(7-fluoroquinolin-3-ylamino)methyl)benzamido)propanoate (6.20 mg, 45% yield) as a yellow solid. $^1$H NMR (400 MHz, CDCl$_3$, δ): 8.50 (d, J=2.3 Hz, 1H), 7.75-7.68 (m, 2H), 7.54 (dd, J=9.9, 2.5 Hz, 1H), 7.45-7.41 (m, 2H), 7.38 (dd, J=9.1, 6.0 Hz, 1H), 7.14 (td, J=8.7, 2.7 Hz, 1H), 6.80 (t, J=5.9 Hz, 1H), 6.70 (d, J=2.7 Hz, 1H), 4.40 (s, 1H), 4.23 (dd, J=9.4, 4.1 Hz, 1H), 4.20-4.08 (m, 2H), 3.70 (q, J=6.2 Hz, 2H), 2.62 (t, J=6.0 Hz, 2H), 2.52 (sxt, J=8.8 Hz, 1H), 2.09-1.97 (m, 1H), 1.71 (dd, J=19.7, 0.4 Hz, 2H), 1.63 (dd, J=8.0, 4.1 Hz, 1H), 1.31-1.21 (m, 3H), 1.13 (s, 3H), 1.09 (s, 3H). (M+1): 478.3.

Intermediate 40 tert-butyl 4-((3,3-dimethylcyclobutyl)(6-fluoroquinolin-3-ylamino)methyl)benzoate

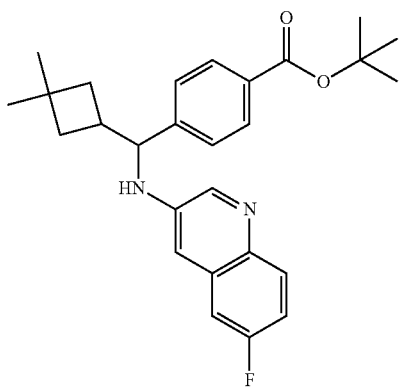 [SMILES: CC1(C)CC(C(Nc2cnc3ccc(F)cc3c2)c2ccc(C(=O)OC(C)(C)C)cc2)C1]

To a solution containing 2-(dicyclohexylphosphino)-3,6-dimethoxy-2'-4'-6'-tri-i-propyl-1,1'-biphenyl (16.3 mg, 0.0300 mmol), chloro(2-dicyclohexylphosphino-3,6-dimethoxy-2',4',6'-triisopropyl-1,1'-biphenyl)[2-(2-aminoethyl)phenyl]palladium(II) (25.0 mg, 0.0300 mmol) and 3-bromo-6-fluoroquinoline (164 mg, 0.670 mmol) was added anhydrous tetrahydrofuran (6.00 mL) and tert-butyl 4-(amino (3,3-dimethylcyclobutyl)methyl)benzoate (175 mg, 0.600 mmol). The mixture was warmed gently and then potassium tert-butoxide (150 mg, 1.30 mmol) was added as a solid. The reaction was then heated at reflux for 18 h. The reaction was then cooled to room temperature and quenched with saturated aqueous ammonium chloride and extracted three times with ethyl acetate. The combined organic layers were dried with sodium sulfate, filtered, and concentrated to give 401 mg of a red oil. Purification by silica gel flash chromatography (0-50% ethyl acetate in heptane) afforded tert-butyl 4-((3,3-dimethylcyclobutyl)(6-fluoroquinolin-3-ylamino)methyl)benzoate (14.0 mg, 5.3% yield) as a brown oil. $^1$H NMR (400 MHz, CDCl$_3$, δ): 8.43 (s, 1H), 7.97-7.92 (m, 2H), 7.86 (dd, J=9.1, 5.8 Hz, 1H), 7.43-7.37 (m, 2H), 7.10 (td, J=8.7, 2.7 Hz, 1H), 7.01 (dd, J=9.6, 2.7 Hz, 1H), 6.61 (d, J=2.5 Hz, 1H), 4.25 (dd, J=9.3, 4.6 Hz, 1H), 2.59-2.46 (m, 1H), 2.00 (s, 1H), 1.76-1.67 (m, 2H), 1.66-1.58 (m, 1H), 1.56 (s, 9H), 1.13 (s, 3H), 1.09 (s, 3H). MS (M+1): 435.3.

Intermediate 41

4-((3,3-dimethylcyclobutyl)(6-fluoroquinolin-3-ylamino)methyl)benzoic acid

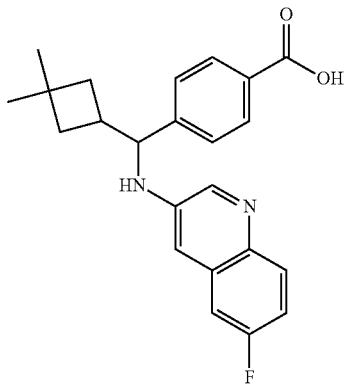 [SMILES: CC1(C)CC(C(Nc2cnc3ccc(F)cc3c2)c2ccc(C(=O)O)cc2)C1]

To a flask containing tert-butyl 4-((3,3-dimethylcyclobutyl)(6-fluoroquinolin-3-ylamino)methyl)benzoate (13.0 mg, 0.0300 mmol) was added anhydrous methylene chloride (0.150 mL) and trifluoroacetic acid (0.150 mL, 0.0300 mmol). The reaction was stirred at room temperature for 1 h. The mixture was concentrated and azeotrophed with toluene to provide crude 4-((3,3-dimethylcyclobutyl)(6-fluoroquinolin-3-ylamino)methyl)benzoic acid (11 mg, 96% yield) as an oil. (M+1): 379.2.

Intermediate 42 ethyl 3-(4-((3,3-dimethylcyclobutyl)(6-fluoroquinolin-3-ylamino)methyl)benzamido)propanoate

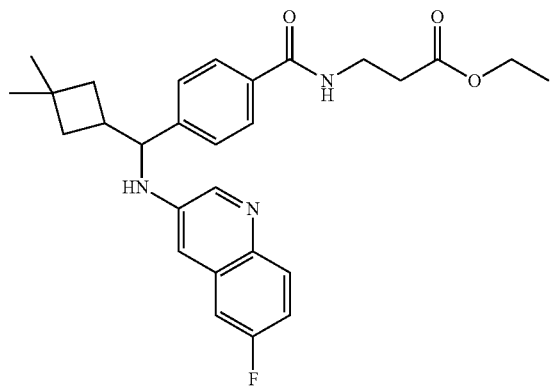 [SMILES: CCOC(=O)CCNC(=O)c1ccc(C(Nc2cnc3ccc(F)cc3c2)C2CC(C)(C)C2)cc1]

To a vial containing 4-((3,3-dimethylcyclobutyl)(6-fluoroquinolin-3-ylamino)methyl)benzoic acid (11.0 mg, 0.0290 mmol), was added 3-aminopropionic acid ethyl ester hydrochloride (4.90 mg, 0.0320 mmol), 1-Hydroxy-7-azabenzotriazole (4.80 mg, 0.0350 mmol) and 1-ethyl-3-(3-dimethylamino propyl)carbodiimide hydrochloride (6.70 mg, 0.0350 mmol). Anhydrous methylene chloride (0.290 mL) was added followed by triethylamine (0.005 mL, 0.0380 mmol). After 18 h, the reaction was diluted with methylene chloride and quenched with a saturated solution of ammonium chloride. The aqueous layer was extracted three times with methylene chloride. The combined organic layers were dried with sodium sulfate, filtered, and concentrated to give 28.6 mg of crude material. Purification by silica gel flash chromatography (0-70% ethyl acetate in heptane) provided ethyl 3-(4-((3,3-dimethylcyclobutyl)(6-fluoroquinolin-3-ylamino)methyl)benzamido)propanoate (7.40 mg, 54% yield) as an oil. $^1$H NMR (400 MHz, CDCl$_3$, δ): 7.86 (s, 1H), 7.72 (d, J=8.2 Hz, 2H), 7.42 (d, J=8.4 Hz, 2H), 7.14-7.06 (m, 1H), 7.05-6.96 (m, 1H), 6.80 (t, J=5.9 Hz, 1H), 6.60 (s, 1H), 4.45 (s, 1H), 4.24 (dd, J=9.3, 4.4 Hz, 1H), 4.19-4.08 (m, 2H), 3.70 (q, J=6.0 Hz, 2H), 2.62 (t, J=6.0 Hz, 2H), 2.58-2.44 (m, 1H), 2.06-1.96 (m, 1H), 1.75-1.67 (m, 2H), 1.67-1.55 (m, 2H), 1.28-1.22 (m, 3H), 1.13 (s, 3H), 1.09 (s, 3H). (M+1): 478.3.

Intermediate 43 ethyl 4-((3,3-dimethylcyclobutyl)(quinolin-3-ylamino)methyl)benzoate

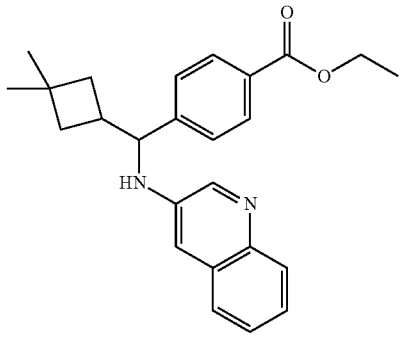 [SMILES: CCOC(=O)c1ccc(C(Nc2cnc3ccccc3c2)C2CC(C)(C)C2)cc1]

A flask containing ethyl 4-(3,3-dimethylcyclobutanecarbonyl)benzoate (397 mg, 1.53 mmol) was charged with toluene (13.9 mL), quinolin-3-amine (200 mg, 1.39 mmol), and para-toluene sulfonic acid (26.8 mg, 0.139 mmol). The reaction was refluxed with a Dean-Stark for 24 h. The reaction was quenched with water and extracted three times with ethyl acetate. The combined organic layers were dried over sodium sulfate, filtered, and concentrated to give 508 mg of crude material. To this crude material was added anhydrous methanol (6.47 mL) and the solution was cooled to 0° C. Sodium borohydride (147 mg, 3.88 mmol) was then added. After 5 h, the reaction was partly concentrated and quenched with saturated aqueous ammonium chloride. The reaction mixture was extracted three times with ethyl acetate. The combined organic layers were then dried over sodium sulfate, filtered, and concentrated to give 560 mg of crude material. Purification by column chromatography (0-50% ethyl acetate in heptane) provided ethyl 4-((3,3-dimethylcyclobutyl)(quinolin-3-ylamino)methyl)benzoate (17.0 mg, 3.4% yield) as an oil. $^1$H NMR (400 MHz, CDCl$_3$) δ: 8.47 (d, J=2.9 Hz, 1H), 8.03-7.97 (m, 2H), 7.90-7.86 (m, 1H), 7.46-7.42 (m, 2H), 7.42-7.30 (m, 3H), 6.69 (d, J=2.7 Hz, 1H), 4.40-4.31 (m, 2H), 4.27 (dd, J=9.2, 4.3 Hz, 1H), 2.58-2.47 (m, 1H), 2.03 (ddd, J=11.2, 7.6, 4.2 Hz, 1H), 1.79-1.67 (m, 2H), 1.67-1.55 (m, 1H), 1.36 (t, J=7.1 Hz, 3H), 1.14 (s, 3H), 1.09 (s, 3H). MS (M+1): 389.3.

Intermediate 44

4-((3,3-dimethylcyclobutyl)(quinolin-3-ylamino)methyl)benzoic acid

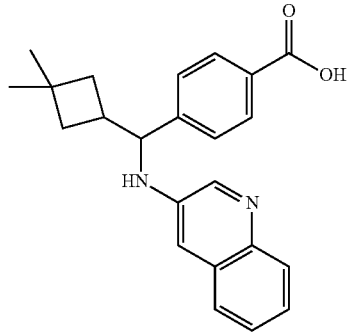 [SMILES: CC1(C)CC(C(Nc2cnc3ccccc3c2)c2ccc(C(=O)O)cc2)C1]

To a flask containing ethyl 4-((3,3-dimethylcyclobutyl)(quinolin-3-ylamino)methyl)benzoate (17.0 mg, 0.0440 mmol) was added tetrahydrofuran (0.110 mL), methanol (0.110 mL), and 1 N sodium hydroxide (0.110 mL, 0.110 mmol). The reaction was stirred for 18 h at room temperature. The reaction was then diluted with ethyl acetate and water. 1 N hydrochloric acid (0.110 mL) was then added dropwise to bring the pH to 3. The aqueous layer was extracted three times with ethyl acetate. The combined organic layers were dried with sodium sulfate, filtered, and concentrated to provide 4-((3,3-dimethylcyclobutyl)(quinolin-3-ylamino)methyl)benzoic acid; (14.8 mg, 93% yield) as a solid. $^1$H NMR (400 MHz, CDCl$_3$) δ: 8.67 (br. s., 1H), 8.06 (d, J=8.2 Hz, 2H), 7.96 (d, J=7.4 Hz, 1H), 7.48 (d, J=8.4 Hz, 2H), 7.46-7.32 (m, 3H), 6.76 (d, J=2.5 Hz, 1H), 4.30 (d, J=9.4 Hz, 1H), 2.62-2.50 (m, 1H), 2.10-1.98 (m, 1H), 1.80-1.69 (m, 2H), 1.69-1.58 (m, 1H), 1.14 (s, 3H), 1.09 (s, 3H). MS (M+1): 361.2.

Intermediate 45 ethyl 3-(4-((3,3-dimethylcyclobutyl)(quinolin-3-ylamino)methyl)benzamido) propanoate

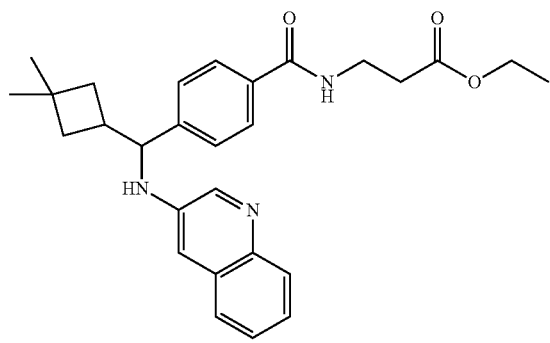 [SMILES: CCOC(=O)CCNC(=O)c1ccc(C(Nc2cnc3ccccc3c2)C2CC(C)(C)C2)cc1]

To a vial containing 4-((3,3-dimethylcyclobutyl)(quinolin-3-ylamino)methyl)benzoic acid (14.0 mg, 0.0390 mmol) was added 3-aminopropionic acid ethyl ester hydrochloric (6.60 mg, 0.0430 mmol), 1-Hydroxy-7-azabenzotriazole (6.40 mg, 0.0470 mmol) and 1-ethyl-3-(3-dimethylamino propyl)carbodiimide hydrochloride (9.00 mg, 0.0470 mmol). Anhydrous methylene chloride (0.390 mL) was added followed by triethylamine (0.007 mL, 0.0510 mmol). After 18 h, the reaction was diluted with methylene chloride and quenched with a saturated solution of ammonium chloride. The aqueous layer was extracted three times with methylene chloride. The combined organic layers were dried with sodium sulfate, filtered, and concentrated to give 26.0 mg of crude material. Purification by column chromatography (0-70% ethyl acetate in heptane) provided ethyl 3-(4-((3,3-dimethylcyclobutyl)(quinolin-3-ylamino)methyl)benzamido)propanoate (11.9 mg, 66% yield) as an oil. $^1$H NMR (400 MHz, CDCl$_3$) δ: 8.48 (d, J=2.7 Hz, 1H), 7.88 (dd, J=8.3, 1.3 Hz, 1H), 7.74-7.67 (m, 2H), 7.46-7.41 (m, 2H), 7.41-7.29 (m, 3H), 6.81 (t, J=6.1 Hz, 1H), 6.69 (d, J=2.7 Hz, 1H), 4.42 (br. s., 1H), 4.25 (dd, J=9.3, 4.4 Hz, 1H), 4.19-4.08 (m, 2H), 3.70 (q, J=6.0 Hz, 2H), 2.61 (t, J=5.7 Hz, 2H), 2.59-2.45 (m, 1H), 2.07-1.97 (m, 1H), 1.76-1.67 (m, 2H), 1.66-1.55 (m, 1H), 1.28-1.21 (m, 3H), 1.13 (s, 3H), 1.09 (m, 3H). MS (M+1): 460.4.

Intermediate 46 ethyl 4-(1-amino-3-methylbutyl)benzoate

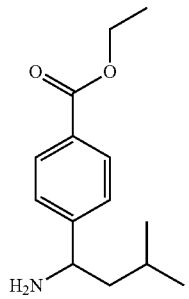 [SMILES: CCOC(=O)c1ccc(C(N)CC(C)C)cc1]

A mixture of 4-(3-Methyl-butyryl)-benzoic acid ethyl ester (2000 mg, 8.536 mM), ammonium acetate (6580 mg, 85.4 mM) and sodium cyanoborohydride (1070 mg, 17.1 mmol) in methanol (17.1 mL) was heated to 60° C. for 6 h. The reaction was cooled, quenched with NH$_4$Cl solution (10 mL). MeOH was removed under reduced pressure. The aqueous solution was extracted with EtOAc (3×30 mL). The organic solution was separated, dried (Na$_2$SO$_4$) and concentrated. The crude material was separated by a 40 g HC silica gel column with 0-15% MeOH in DCM. The desired product was collected as colorless oily material (1560 mg, 77.7%). $^1$H NMR (500 MHz, CDCl$_3$) δ ppm 0.91 (dd, J=13.66, 6.59 Hz, 6 H) 1.40 (t, J=7.07 Hz, 3 H) 1.84-1.99 (m, 3 H) 4.27-4.42 (m, 3 H) 6.36 (br. s., 2 H) 7.51 (d, J=8.05 Hz, 2 H) 8.05 (d, J=8.05 Hz, 2 H). GC: m/z 235.

Intermediate 47

4-[3-Methyl-1-(8-methyl-quinoline-3-ylamino)-butyl]-benzoic acid ethyl ester

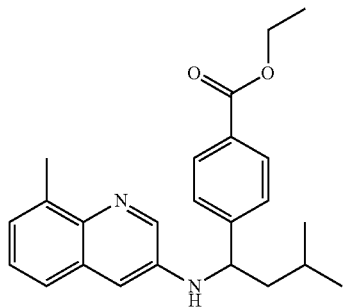 [SMILES: CCOC(=O)c1ccc(C(CC(C)C)Nc2cnc3c(C)cccc3c2)cc1]

To a reaction vial with 4-(1-Amino-3-methyl-butyryl)-benzoic acid ethyl ester (340 mg, 1.5 mM) was added DMSO (4.88 mL), 3-bromo-8-methylquinoline (325 mg, 1.46 mM), followed by CuI catalyst (27.8 mg, 0.146 mM) and CsOAc (562 mg, 2.93 mM). The mixture was purged with argon gas and then the tube was sealed. The reaction mixture was heated to 100° for 24 h. The reaction mixture was cooled, diluted with EtOAc (10 mL), washed with water (3×5 mL), dried (Na$_2$SO$_4$) and concentrated. The crude material was separated by a 40 g silica gel with 0-50% EtOAc in heptanes to give a yellow color solid product (62 mg, 11%). $^1$H NMR (400 MHz, CDCl$_3$) δ ppm 0.95 (d, J=6.25 Hz, 3 H) 1.00 (d, J=6.25 Hz, 3 H) 1.35 (t, 3 H) 1.58-1.68 (m, 1 H) 1.68-1.84 (m, 2 H) 2.70 (s, 3 H) 4.33 (q, 2 H) 4.36-4.42 (m, 1 H) 4.44-4.54

Intermediate 48

4-[3-Methyl-1-(8-methyl-quinolin-3-ylamino)-butyl]-benzoic acid

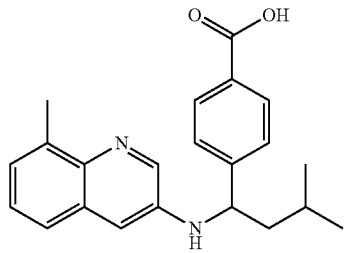 [SMILES: Cc1cccc2cc(NC(CC(C)C)c3ccc(C(=O)O)cc3)cnc12]

A mixture of 4-[3-Methyl-1-(8-methyl-quinoline-3-ylamino)-butyl]-benzoic acid ethyl ester (62 mg, 0.16 mM) and 1N aqueous NaOH solution (0.413 mL, 0.413 mM) in THF-MeOH (1:1, 3.3 mL) was heated to 50° C. for 4 h. The reaction was cooled, concentrated to remove organic solvent. The aqueous solution was diluted with DCM (5 mL), acidified by 1N HCl solution to pH=3-4. The organic solution was separated and the aqueous solution was extracted with 10% i-PrOH-DCM (5×5 mL). The combined organic solution were dried (Na$_2$SO$_4$) and concentrated to give a yellow solid product (45.7 mg, 79%). $^1$H NMR (400 MHz, CD$_3$OD) δ ppm 0.98 (d, J=6.44 Hz, 3 H) 1.03 (d, J=6.25 Hz, 3 H) 1.56-1.68 (m, 1 H) 1.73-1.93 (m, 2 H) 2.68 (d, 3 H) 4.60-4.68 (m, 1 H) 7.23-7.35 (m, 2 H) 7.38 (d, 1 H) 7.44 (d, 1 H) 7.48-7.61 (m, 2 H) 7.96 (d, 2 H) 8.53 (dd, 1 H), two protons (COOH and NH) were exchanged. This material will be used for the next step reaction without further work-up.

Intermediate 49

3-{4-[3-Methyl-1-(8-methyl-quinolin-3-ylamino)-butyl]-benzoylamino}-propionic acid methyl ester

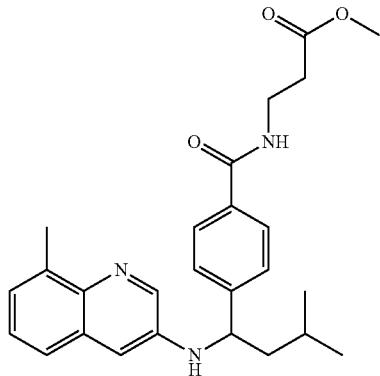 [SMILES: COC(=O)CCNC(=O)c1ccc(C(CC(C)C)Nc2cnc3c(C)cccc3c2)cc1]

To a solution of 4-[3-Methyl-1-(8-methyl-quinolin-3-ylamino)-butyl]-benzoic acid (5) (45 mg, 0.131 mM) in DCM (1 mL) was added TEA (66.3 mg, 0.655 mM) and followed by 3-amino-propionic acid methyl ester hydrochloric acid (6) (27.5 mg, 0.197 mM) and then HBTU (59.5 mg, 0.157 mM). The reaction was stirred at RT for 16 h. The reaction mixture was diluted with EtOAc (5 mL) and washed with water (2×2 mL). The organic layer was separated, dried over Na$_2$SO$_4$ and concentrated. The crude material was separated by a 12 g silica gel column with 10-80% EtOAc in heptane to afford desired product (44 mg, 77%). $^1$H NMR (500 MHz, CDCl$_3$) δ ppm 0.98 (d, J=6.34 Hz, 3 H) 1.05 (d, 3 H) 1.62-1.71 (m, 1 H) 1.71-1.86 (m, 2 H) 2.62-2.67 (m, 2 H) 2.72 (s, 3 H) 3.67-3.79 (m, 5 H) 4.39 (d, J=5.37 Hz, 1 H) 4.49-4.55 (m, 1 H) 6.76 (d, J=2.44 Hz, 1 H) 6.77-6.85 (m, 1 H) 7.20-7.27 (m, 1 H) 7.28 (s, 1 H) 7.30 (d, J=7.07 Hz, 1 H) 7.46 (d, J=8.05 Hz, 2 H) 7.74 (d, J=8.29 Hz, 2 H) 8.50 (d, J=2.68 Hz, 1 H). LC-MS: m/z 434.2 (M+1).

Intermediate 50

4-[3-Methyl-1-(7-methyl-quinoline-3-ylamino)-butyl]-benzoic acid ethyl ester

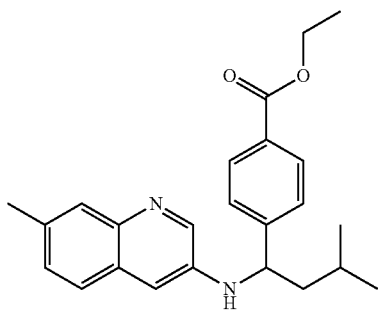 [SMILES: CCOC(=O)c1ccc(C(CC(C)C)Nc2cnc3cc(C)ccc3c2)cc1]

To a reaction vial with 4-(1-Amino-3-methyl-butyryl)-benzoic acid ethyl ester (2) (440 mg, 1.9 mM) was added DMSO (6.33 mL), 3-bromo-7-methylquinoline (9) (420 mg, 1.9 mM), followed by CuI catalyst (36 mg, 0.19 mM) and CsOAc (726 mg, 3.78 mM). The mixture was purged with argon gas and then the tube was sealed. The reaction mixture was heated to 100° for 48 h. The reaction mixture was cooled, diluted with EtOAc (10 mL), washed with water (3×5 mL), dried (Na$_2$SO$_4$) and concentrated. The crude material was separated by a 40 g silica gel with 0-80% EtOAc in heptane to give a yellow color product (108 mg, 15%). $^1$H NMR (500 MHz, CDCl$_3$) δ ppm 0.98 (d, J=6.34 Hz, 3 H) 1.04 (d, J=6.34 Hz, 3 H) 1.39 (t, 3 H) 1.61-1.71 (m, 1 H) 1.71-1.86 (m, 2 H) 2.46 (s, 3 H) 4.36 (q, 2 H) 4.38-4.43 (m, 1 H) 4.47-4.56 (m, 1 H) 6.75 (d, J=1.95 Hz, 1 H) 7.20 (d, J=8.29 Hz, 1 H) 7.36 (d, J=8.05 Hz, 1 H) 7.47 (d, J=8.29 Hz, 2 H) 7.69 (s, 1 H) 8.03 (d, 2 H) 8.47 (br. s., 1 H). LC-MS: m/z 377.2 (M+1).

Intermediate 51

4-[3-Methyl-1-(8-methyl-quinolin-3-ylamino)-butyl]-benzoic acid

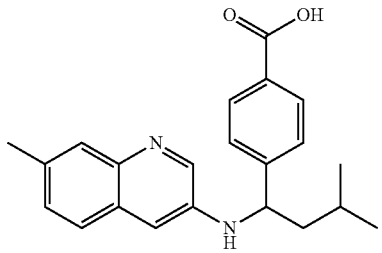 [SMILES: Cc1ccc2cc(NC(CC(C)C)c3ccc(C(=O)O)cc3)cnc2c1]

A mixture of 4-[3-Methyl-1-(7-methyl-quinoline-3-ylamino)-butyl]-benzoic acid ethyl ester (48 mg, 0.13 mM) and 1N aqueous NaOH solution (0.318 mL, 0.318 mM) in THF-MeOH (1:1, 1.5 mL) was heated to 50° for 5 h. The reaction was cooled, concentrated to remove organic solvent. The aqueous solution was diluted with DCM (5 mL), acidified by 1N HCl solution to pH=3-4. The organic solution was separated and the aqueous solution was extracted with DCM (3×5 mL). The combined organic solution were dried (Na₂SO₄) and concentrated to give a yellow solid product (44 mg, ~100%). ¹H NMR (400 MHz, CD₃OD) δ ppm 0.97 (d, J=6.44 Hz, 3 H) 1.02 (d, J=6.44 Hz, 3 H) 1.54-1.67 (m, 1 H) 1.73-1.91 (m, 2 H) 2.43 (s, 3 H) 4.57-4.65 (m, 1 H) 7.14 (d, J=2.54 Hz, 1 H) 7.28 (dd, J=8.49, 1.27 Hz, 1 H) 7.46-7.58 (m, 4 H) 7.97 (d, 2 H) 8.44 (d, J=2.34 Hz, 1 H), two protons (COOH and NH) were exchanged. LC-MS: m/z 349.1 (M+1). This material will be used for the next step reaction without further work-up.

Intermediate 52

3-{4-[3-Methyl-1-(7-methyl-quinolin-3-ylamino)-butyl]-benzoylamino}-propionic acid methyl ester

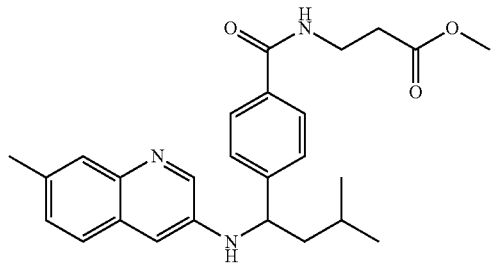

To a solution of 4-[3-Methyl-1-(7-methyl-quinolin-3-ylamino)-butyl]-benzoic acid (44 mg, 0.13 mM) in DCM (1 mL) was added TEA (63.6 mg, 0.629 mM) and followed by 3-amino-propionic acid methyl ester hydrochloric acid (6) (26.4 mg, 0.189 mM) and then HBTU (57.3 mg, 0.151 mM). The reaction was stirred at RT for 16 h. The reaction mixture was diluted with EtOAc (5 mL) and washed with water (2×2 mL). The organic layer was separated, dried over Na₂SO₄ and concentrated. The crude material was separated by a 12 g silica gel column with 10-100% EtOAc in heptane to afford desired product (49 mg, 90%). ¹H NMR (500 MHz, CDCl3) δ ppm 0.98 (d, J=6.10 Hz, 3 H) 1.04 (d, J=6.34 Hz, 3 H) 1.61-1.70 (m, 1 H) 1.71-1.86 (m, 2 H) 2.66 (t, 2 H) 2.82 (s, 3 H) 3.68-3.76 (m, 5 H) 4.36 (d, J=4.88 Hz, 1 H) 4.44-4.54 (m, 1 H) 6.73 (d, J=2.20 Hz, 1 H) 6.80 (t, J=5.49 Hz, 1 H) 7.20 (d, J=8.29 Hz, 1 H) 7.35 (d, J=8.54 Hz, 1 H) 7.45 (d, J=8.29 Hz, 2 H) 7.67 (s, 1 H) 7.75 (d, 2 H) 8.45 (d, J=2.44 Hz, 1 H). LC-MS: 434.2 (M+1).

Intermediate 53

3-bromo-6-methylquinoline

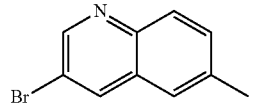

6-Methylquinoline (1.9906 g, 13.903 mmol) was dissolved in 20 mL of carbon tetrachloride. Bromine (0.72 mL, 14 mmol) was added dropwise to the reaction solution and the suspension was heated to reflux (80° C.). Pyridine (1.15 mL, 13.9 mmol) was added while reaction was heating to 80° C. and the reaction was allowed to stir at reflux for 1.5 hours. The reaction was cooled to room temperature and diluted with dichloromethane. The reaction was washed with water and the organic was dried over sodium sulfate, filtered and concentrated to give a thick brown oil that solidified upon standing. The crude solid was purified on an 80 g silica gel ISCO column eluting with a very slow gradient: 0% to 15% to 20% ethyl acetate in heptanes to give the desired 3-bromo-6-methylquinoline. ¹H NMR (400 MHz, CDCl₃) δ ppm 2.52 (s, 3 H) 7.47 (s, 1 H) 7.54 (dd, J=8.59, 1.95 Hz, 1 H) 7.95 (d, J=8.59 Hz, 1 H) 8.19 (d, J=2.15 Hz, 1 H) 8.81 (d, J=2.34 Hz, 1 H). GCMS=221 at 2.93 minutes.

Intermediate 54 ethyl (+/−)-4-(4,4,4-trifluoro-1-hydroxybutyl)benzoate

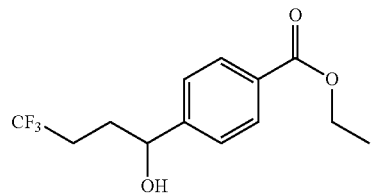 [SMILES: CCOC(=O)c1ccc(C(O)CCC(F)(F)F)cc1]

To a solution of the ethyl 4-iodobenzoate (1.21 ml, 7.24 mmol) in tetrahydrofuran (12 ml) at −40° C. was added isopropylmagnesium chloride lithium chloride complex (6.13 ml, 7.97 mmol, 1.3 M in tetrahydrofuran) dropwise. The mixture was stirred for approximately 1 hour whereupon 4,4,4-trifluorobutanal (0.761 ml, 0.724 mmol) was added dropwise. The mixture was stirred at −40° C. for 15 minutes and slowly warmed to ambient temperature over 12 hours. The reaction was quenched with aqueous 1.0 M hydrochloric acid, and the aqueous layer was extracted with ethyl acetate (3×). The combined organic layers were dried over magnesium sulfate, filtered, and concentrated under reduced pressure to give ethyl (+/−)-4-(4,4,4-trifluoro-1-hydroxybutyl) benzoate, which was used without further purification.

Intermediate 55 ethyl (+/−)-4-(4,4,4-trifluoro-1-((methylsulfonyl)oxy)butyl)benzoate

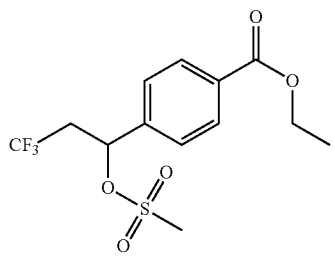 [SMILES: CCOC(=O)c1ccc(C(CC(F)(F)F)OS(C)(=O)=O)cc1]

To a solution of ethyl (+/−)-4-(4,4,4-trifluoro-1-hydroxybutyl)benzoate (264 mg, 0.956 mmol) in tert-butyl methyl ether (4.8 mL) was added triethylamine (0.201 mL, 1.43 mmol), followed by methanesulfonyl chloride (0.091 mL, 1.15 mmol). The resulting mixture was stirred for 1 hour. Then, the reaction mixture was diluted with tert-butyl methyl ether (25 mL) and washed with water (15 mL), sat. aq sodium bicarbonate (15 mL), then sat. aq sodium chloride (15 mL). The organic layer was dried over Na₂SO₄ and filtered, and the filtrate was concentrated under reduced pressure to give ethyl (+/−)-4-(4,4,4-trifluoro-1-((methylsulfonyl)oxy)butyl)benzoate. This material was used without further purification. ¹HNMR (400 MHz, CDCl₃) δ 8.12 (d, J=8.4 Hz, 2 H), 7.48 (d, J=8.2 Hz, 2 H), 5.63 (dd, J=7.9, 4.8 Hz, 1 H), 4.41 (q, J=7.0 Hz, 2 H), 2.77 (s, 3 H), 2.39-2.08 (m, 4 H), 1.41 (t, J=7.1 Hz, 3 H).

Intermediate 56 ethyl (+/−)-4-(4,4,4-trifluoro-1-(quinolin-3-ylamino)butyl)benzoate

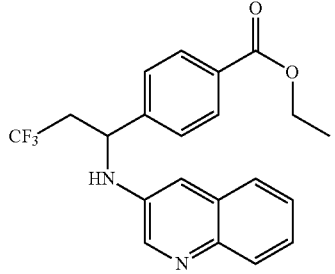 [SMILES: CCOC(=O)c1ccc(C(CC(F)(F)F)Nc2cnc3ccccc3c2)cc1]

To a solution of ethyl (+/−)-4-(4,4,4-trifluoro-1-((methylsulfonyl)oxy)butyl)benzoate (123 mg, 0.347 mmol) in acetonitrile (1.74 mL) was added 3-amino quinoline (60.6 mg, 0.416 mmol), followed by potassium phosphate (155 mg, 0.694 mmol). The resulting mixture was heated to 60° C. for 20 hours. The reaction mixture was cooled to room temperature, diluted with water (20 mL), and extracted with ethyl acetate (3×20 mL). The combined organic layers were dried over $Na_2SO_4$ and filtered, and the filtrate was concentrated under reduced pressure. Purification by silica gel flash chromatography (ethyl acetate/heptane) gave ethyl (+/−)-4-(4,4,4-trifluoro-1-(quinolin-3-ylamino)butyl)benzoate. $^1$H NMR (400 MHz, $CDCl_3$) δ 8.51 (d, J=2.5 Hz, 1H), 8.06 (d, J=8.4 Hz, 2 H), 7.92 (d, J=7.8 Hz, 1 H), 7.50-7.44 (m, 3 H), 7.44-7.35 (m, 2 H), 6.81 (d, J=2.5 Hz, 1 H), 4.62-4.54 (m, 1 H), 4.44-4.33 (m, 3 H), 2.36-2.10 (m, 4 H), 1.38 (t, J=7.1 Hz, 3 H).

Intermediate 57

(+/−)-4-(4,4,4-trifluoro-1-(quinolin-3-ylamino)butyl)benzoic acid

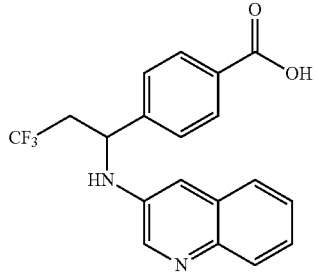 [SMILES: O=C(O)c1ccc(C(CC(F)(F)F)Nc2cnc3ccccc3c2)cc1]

To a solution of ethyl (+/−)-4-(4,4,4-trifluoro-1-(quinolin-3-ylamino)butyl)benzoate (95 mg, 0.24 mmol) in methanol (1.2 mL) and tetrahydrofuran (1.2 mL) was added 1 N aq sodium hydroxide (1.2 mL, 1.2 mmol). After 17 hours, the solution was concentrated under reduced pressure to remove methanol and tetrahydrofuran. The mixture was then acidified to pH 5 with 1 N aq hydrochloric acid and diluted with sat. aq sodium chloride (20 mL). The mixture was extracted with ethyl acetate (3×20 mL). The combined organic layers were dried over $Na_2SO_4$ and filtered, and the filtrate was concentrated under reduced pressure to give (+/−)-4-(4,4,4-trifluoro-1-(quinolin-3-ylamino)butyl)benzoic acid. $^1$HNMR (400 MHz, $CD_3OD$) δ 8.50 (br. s, 1 H), 8.02 (d, J=8.2 Hz, 2 H), 7.80-7.73 (m, 1 H), 7.57 (d, J=8.2 Hz, 2 H), 7.53-7.47 (m, 1 H), 7.40-7.32 (m, 2 H), 6.95 (d, J=2.5 Hz, 1 H), 4.73-4.64 (m, 1 H), 2.55-2.39 (m, 1 H), 2.39-2.22 (m, 1 H), 2.22-2.04 (m, 2 H).

Intermediate 58 ethyl (+/−)-3-(4-(4,4,4-trifluoro-1-(quinolin-3-ylamino)butyl)benzamido) propanoate

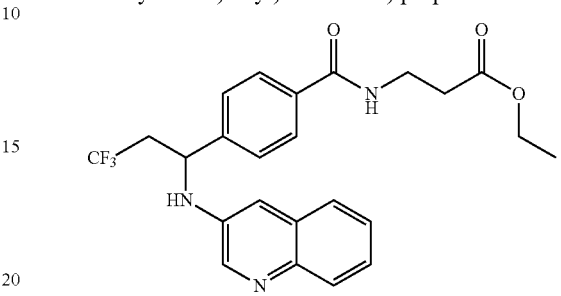

To a suspension of (+/−)-4-(4,4,4-trifluoro-1-(quinolin-3-ylamino)butyl)benzoic acid (74.0 mg, 0.200 mmol), β-alanine ethyl ester hydrochloride (96.0 mg, 0.594 mmol), and 1-hydroxybenzotriazole hydrate (80%, 20 wt % water, 100 mg, 0.594 mmol) in dichloromethane (2 mL) was added triethylamine (0.250 mL, 1.78 mmol) followed by N-(3-dimethylaminopropyl)-N'-ethylcarbodiimide hydrochloride (96.3 mg, 0.495 mmol), and the solution was stirred at room temperature for 19 hours. The reaction mixture was diluted with dichloromethane (15 mL) and washed with water (3×15 mL) then sat. aq sodium chloride (10 mL). The organic layer was dried over $Na_2SO_4$ and filtered, and the filtrate was concentrated under reduced pressure. Purification by silica gel flash chromatography (ethyl acetate/heptane) gave ethyl (+/−)-3-(4-(4,4,4-trifluoro-1-(quinolin-3-ylamino)butyl)benzamido) propanoate. $^1$H NMR (400 MHz, $CDCl_3$) δ 8.69-8.59 (m, 1 H), 7.96 (d, J=7.6 Hz, 1 H), 7.78 (d, J=8.2 Hz, 2 H), 7.52-7.46 (m, 3 H), 7.46-7.37 (m, 2 H), 6.88-6.79 (m, 2 H), 4.61-4.52 (m, 1 H), 4.16 (q, J=7.0 Hz, 2 H), 3.72 (q, J=6.1 Hz, 2 H), 2.63 (t, J=5.9 Hz, 2 H), 2.37-2.08 (m, 4 H), 1.26 (t, J=7.1 Hz, 4 H).

Intermediate 59 tert-butyl 4-(3-methylbutanoyl)benzoate

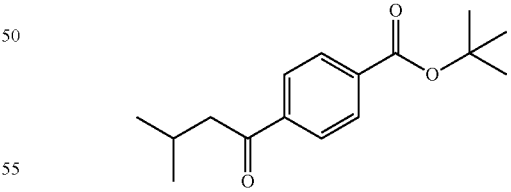

To a slurry of 4-(3-methylbutanoyl)benzoic acid (499 mg, 2.42 mmol) in dichloromethane (6 mL) was added O-tert-butyl-N,N'-diisopropylisourea (1.82 g, 9.07 mmol). The mixture was stirred at room temperature for 50 hours then diluted with tert-butyl methyl ether (75 mL). The mixture was washed with sat. aq sodium bicarbonate (50 mL), dried over anhydrous $Na_2SO_4$, and filtered, and the filtrate was concentrated. Purification by silica gel flash chromatography (ethyl acetate/heptane) gave tert-butyl 4-(3-methylbutanoyl)benzoate as a colorless oil. $^1$H NMR (400 MHz, $CDCl_3$) δ 8.09-

8.04 (m, 2 H), 8.00-7.94 (m, 2 H), 2.86 (d, J=6.8 Hz, 2 H), 2.37-2.23 (m, 1 H), 1.62 (s, 9 H), 1.01 (d, J=6.7 Hz, 6 H).

Intermediate 60 tert-butyl (+/−)-4-(1-amino-3-methylbutyl)benzoate

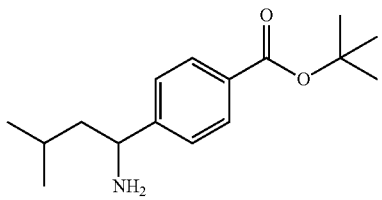 [SMILES: CC(C)CC(N)c1ccc(C(=O)OC(C)(C)C)cc1]

To a solution of tert-butyl 4-(3-methylbutanoyl)benzoate (500 mg, 1.91 mmol) and ammonium acetate (1.50 g, 19.1 mmol) in methanol (9.5 mL) was added sodium cyanoborohydride (189 mg, 2.86 mmol). The mixture was heated to 60° C. for 21 hours, then cooled to room temperature. 1 N hydrochloric acid (7 mL) was added dropwise. After 1 hour, the mixture was concentrated under reduced pressure to remove methanol. 1 N sodium hydroxide (10 mL) was added, and the mixture was extracted with dichloromethane (3×25 mL). The combined organics were washed with sat. aq sodium chloride (15 mL), dried over anhydrous $Na_2SO_4$, and filtered, and the filtrate was concentrated. Purification by silica gel flash chromatography (methanol/dichloromethane) gave tert-butyl (+/−)-4-(1-amino-3-methylbutyl)benzoate as a colorless oil. $^1$H NMR (400 MHz, $CDCl_3$) δ 7.99-7.94 (m, 2 H), 7.41-7.37 (m, 2 H), 4.08-4.01 (m, 1 H), 1.60 (s, 9 H), 1.59-1.43 (m, 3 H), 0.92 (d, J=6.5 Hz, 3 H), 0.90 (d, J=6.3 Hz, 3 H).

Intermediate 61 tert-butyl (+/−)-4-(3-methyl-1-((3-methylquinolin-2-yl)amino)butyl)benzoate

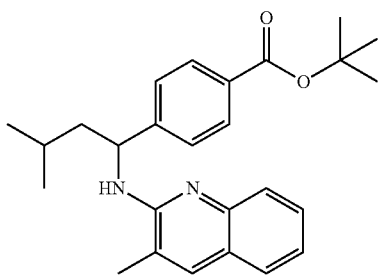 [SMILES: Cc1cc2ccccc2nc1NC(CC(C)C)c1ccc(C(=O)OC(C)(C)C)cc1]

To a solution of tert-butyl (+/−)-4-(3-methylbutanoyl)benzoate (527 mg, 2.00 mmol) and 3-methylquinoline N-oxide (318 mg, 2.00 mmol) in dichloromethane (8.0 mL) was added diisopropylethylamine (1.31 mL, 7.50 mmol) followed by bromotripyrrolidinophosphonium hexafluorophosphate (1.18 g, 2.50 mmol). The solution was stirred at room temperature for 18 hours then diluted with sat. aq sodium bicarbonate (20 mL). The mixture was extracted with ethyl acetate (3×20 mL). The combined organics were dried over anhydrous $Na_2SO_4$ and filtered, and the filtrate was concentrated. Purification by silica gel flash chromatography (ethyl acetate/heptane) gave tert-butyl (+/−)-4-(3-methyl-1-((3-methylquinolin-2-yl)amino)butyl)benzoate as a white solid. $^1$H NMR (400 MHz, $CDCl_3$) δ 7.94 (d, J=8.2 Hz, 2 H), 7.63 (d, J=8.2 Hz, 1 H), 7.59 (s, 1 H), 7.54-7.48 (m, 3 H), 7.47-7.41 (m, 1 H), 7.19-7.13 (m, 1 H), 5.56 (q, J=7.4 Hz, 1 H), 4.73 (d, J=7.0 Hz, 1 H), 2.28 (s, 3 H), 1.94-1.83 (m, 1 H), 1.81-1.70 (m, 1 H), 1.70-1.60 (m, 1 H), 1.57 (s, 9 H), 1.04 (d, J=6.6 Hz, 3 H), 0.97 (d, J=6.6 Hz, 3 H).

Intermediate 62

(+/−)-4-(3-methyl-1-((3-methylquinolin-2-yl)amino)butyl)benzoic acid trifluoroacetic acid salt

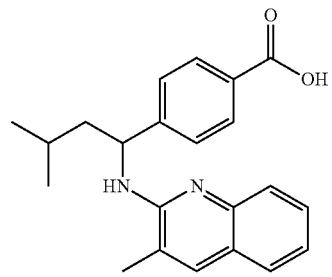 [SMILES: Cc1cc2ccccc2nc1NC(CC(C)C)c1ccc(C(=O)O)cc1]

To a solution of tert-butyl (+/−)-4-(3-methyl-1-((3-methylquinolin-2-yl)amino)butyl)benzoate (325 mg, 0.803 mmol) in dichloromethane (8.0 mL) was added trifluoroacetic acid (0.62 mL, 8.0 mmol). The solution was stirred at room temperature for 17 hours then concentrated under reduced pressure. Toluene (3 mL) was added, and the solution was again concentrated under reduced pressure to remove excess trifluoroacetic acid to give (+/−)-4-(3-methyl-1-((3-methylquinolin-2-yl)amino)butyl)benzoic acid trifluoroacetic acid salt as a white solid. $^1$H NMR (400 MHz, $CD_3OD$) δ 8.26 (s, 1 H), 8.06 (d, J=8.4 Hz, 2 H), 7.84 (d, J=7.8 Hz, 1 H), 7.80-7.75 (m, 1 H), 7.75-7.69 (m, 1 H), 7.58 (d, J=8.4 Hz, 2 H), 7.55-7.48 (m, 1 H), 5.50 (dd, J=5.0, 9.5 Hz, 1 H), 2.56 (s, 3 H), 2.24-2.14 (m, 1 H), 1.92-1.75 (m, 2 H), 1.08 (d, J=6.4 Hz, 3 H), 1.05 (d, J=6.2 Hz, 3 H).

Intermediate 63

Ethyl 3-(4-(3-methyl-1-((3-methylquinolin-2-yl)amino)butyl)benzamido)propanoate, Isomer 1 and Isomer 2

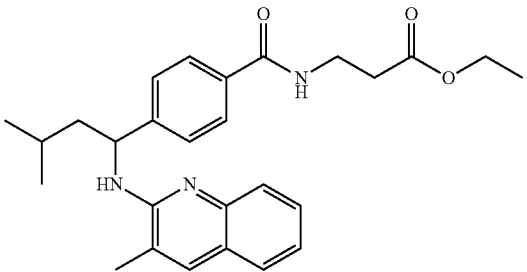 [SMILES: CCOC(=O)CCNC(=O)c1ccc(C(CC(C)C)Nc2nc3ccccc3cc2C)cc1]

(+/−)-4-(3-methyl-1-((3-methylquinolin-2-yl)amino)butyl)benzoic acid trifluoroacetic acid salt (461 mg, 1.00 mmol), β-alanine ethyl ester hydrochloride (645 mg, 3.99 mmol), and 1-hydroxybenzotriazole hydrate (80%, 20 wt % water, 674 mg, 3.99 mmol) were suspended in dichloromethane (10.0 mL). Triethylamine (1.40 mL, 9.97 mmol) followed by N-(3-dimethylaminopropyl)-N'-ethylcarbodiimide hydrochloride (776 mg, 3.99 mmol) were added, and the solution was stirred at room temperature for 66 hours. The reaction mixture was diluted with dichloromethane (40 mL), washed with water (3×30 mL) and sat. aq NaCl (20 mL), dried over $Na_2SO_4$, and filtered, and the filtrate was concentrated under reduced pressure. Purification by silica gel flash chromatography (ethyl acetate/heptane) followed by chiral SFC (Chiralpak AD-H column, 10 mm×250 cm, 25% methanol/carbon dioxide eluent, 0.2% isopropylamine modifier) gave ethyl 3-(4-(1-((3-methylquinolin-2-yl)amino)butyl)benzamido)propanoate, isomer 1 (analytical chiral SFC 6.1 min retention) and 3-(4-(1-((3-methylquinolin-2-yl)amino)butyl) benzamido) propanoate as a mixture of methyl and ethyl esters, isomer 2 (analytical chiral SFC 6.7 min retention). Ethyl ester: $^1$H NMR (400 MHz, CDCl$_3$) δ 7.71 (d, J=8.2 Hz, 2 H), 7.66-7.57 (m, 2 H), 7.56-7.48 (m, 3 H), 7.44 (t, J=7.4 Hz, 1 H), 7.16 (t, J=7.4 Hz, 1 H), 6.81-6.73 (m, 1 H), 5.60-5.52 (m, 1 H), 4.73 (d, J=6.8 Hz, 1 H), 4.16 (q, J=7.0 Hz, 2 H), 3.71 (q, J=6.0 Hz, 2 H), 2.62 (t, J=5.9 Hz, 2 H), 2.28 (s, 3 H), 1.93-1.82 (m, 1 H), 1.81-1.70 (m, 1 H), 1.69-1.60 (m, 1 H), 1.26 (t, J=7.1 Hz, 3 H), 1.04 (d, J=6.4 Hz, 3 H), 0.97 (d, J=6.2 Hz, 3 H). Methyl ester: $^1$H NMR (400 MHz, CDCl$_3$) δ 7.71 (d, J=8.2 Hz, 2 H), 7.66-7.57 (m, 2 H), 7.56-7.48 (m, 3 H), 7.44 (t, J=7.4 Hz, 1 H), 7.16 (t, J=7.3 Hz, 1 H), 6.81-6.71 (m, 1 H), 5.60-5.52 (m, 1 H), 4.77-4.69 (m, 1 H), 3.76-3.66 (m, 5 H), 2.66-2.59 (m, 2 H), 2.28 (s, 3 H), 1.93-1.82 (m, 1 H), 1.81-1.70 (m, 1 H), 1.69-1.60 (m, 1 H), 1.04 (d, J=6.4 Hz, 3 H), 0.97 (d, J=6.4 Hz, 3 H).

Intermediate 64

(+/−)-methyl 4-(1-hydroxybutyl)benzoate

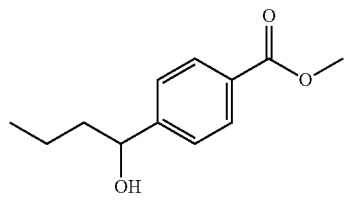

A solution of methyl 4-iodobenzoate (151.3 g, 565.8 mmol) in tetrahydrofuran (908 mL) was cooled to −30° C. To this solution was added isopropylmagnesium chloride solution (2 M in tetrahydrofuran, 325.4 mL, 650.7 mmol) dropwise over 20 minutes. The reaction was stirred at −33° C. for 1 hour, then butanal (61.09 mL, 679.0 mmol) was added dropwise over 15 minutes. The reaction was warmed to 0° C. Methyl tert-butyl ether (1000 mL) and citric acid solution (5 wt % aq, 1000 mL) were added, and the mixture was stirred for 1 hour. The layers were separated, and the organic phase was washed with water (500 mL). The combined aqueous phases were back-extracted with methyl tert-butyl ether (250 mL). The combined organic phases were dried over magnesium sulfate, filtered and concentrated under vacuum to afford Intermediate 64 as a yellow oil. $^1$H NMR (400 MHz, CDCl$_3$, δ): 7.97-8.02 (m, 2 H), 7.40 (d, J=8.4 Hz, 2 H), 4.74 (dd, J=7.8, 5.7 Hz, 1 H), 3.90 (s, 3 H), 1.61-1.82 (m, 2 H), 1.23-1.49 (m, 2 H), 0.92 (t, J=7.32 Hz, 3 H).

Intermediate 65 methyl 4-butyrylbenzoate

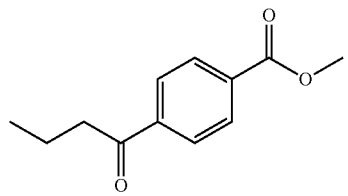

To a solution of Intermediate 64 (129.5 g, 565.9 mmol) in dichloromethane (129.5 mL) was added triethylamine (394.4 mL, 2.83 mol). The solution was cooled to 10° C., then a solution of sulfur trioxide pyridine complex (202.2 g, 1.24 mol) in dimethyl sulfoxide (777.0 mL) was added slowly over 30 minutes, keeping the internal temperature below 15° C. The reaction was warmed to 25° C. After 16 hours, the mixture was diluted slowly with hydrochloric acid (1.22 M in water, 2780 mL). The reaction was stirred for 15 minutes, then the layers were separated. The organic layer was washed with water (1000 mL), then treated with Darco KB-B (13 g), magnesium sulfate (13 g), and celite and slurried for 30 minutes. The slurry was filtered, and the solids were washed with methyl tert-butyl ether (250 mL). The filtrate was concentrated at atmospheric pressure (internal temperature 55-58° C.) to a volume of approximately 500 mL. This solution was cooled at 2° C./minute to 15° C. Heptane (250 mL) was added, and the slurry was cooled to 10° C. and stirred for 1 hour. The slurry was filtered, and the solids were washed with 1:2 methyl tert-butyl ether: heptane (260 mL, cooled to 5° C.) then heptane (250 mL). The resulting off-white solid was dried under vacuum to provide Intermediate X202. $^1$H NMR (400 MHz, CDCl$_3$, δ): 8.08-8.13 (m, 2 H), 7.97-8.01 (m, 2 H), 3.94 (s, 3 H), 2.96 (t, J=7.3 Hz, 2 H), 1.77 (m, 2 H), 1.00 (t, J=7.4 Hz, 3 H).

Intermediate 66

(S)-methyl 4-(1-hydroxybutyl)benzoate

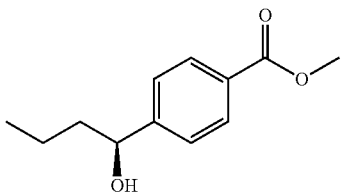

To a solution of borane-diethylaniline complex (49.79 mL, 280.0 mmol) and (R)-(+)-2-methyl-CBS-oxaborolidine solution (1 M in toluene, 18.67 mL, 18.67 mmol) in tetrahydrofuran (154 mL) at 20° C. was added a solution of Intermediate 65 (77.00 g, 373.4 mmol) in tetrahydrofuran (385 mL) over 2 hours. After stirring for 10 minutes, the reaction was quenched by slow addition of methanol (34.75 mL, 858.7 mmol) over 30 minutes while maintaining the temperature below 20° C. Hydrochloric acid (1 N in water, 373.4 mL, 373.4 mmol) was then added over 10 minutes while maintaining the temperature below 20° C. Methyl tert-butyl ether (385 mL) was added and mixture was stirred for 30 minutes. The layers were separated. Hydrochloric acid (1 N in water, 373.4 mL) was added to the organic layer, and the mixture was stirred for 10 minutes. The layers were separated, and the organic layer was diluted with water (77.0 mL). The mixture was stirred for 5 minutes, then the layers were separated. The combined aqueous layers were back-extracted with methyl tert-butyl ether (2×150 mL). The combined organic layers were distilled at atmospheric pressure (temperature less than 80° C.) until 250 mL of solution remained. The solution was then diluted with heptane (847 mL) and distilled at atmospheric pressure (100-110° C.) until 650 mL of solvent had been distilled. Again, heptane (462 mL) was added, and the solution was distilled at atmospheric pressure (100-110° C.) until the internal temperature reached 100° C. Heptane was added to a total volume of 700 mL. The solution was then cooled to −15° C. with vigorous stirring. The slurry was warmed to 15° C. and stirred overnight. The mixture was then cooled to −15° C. and stirred for 3.5 hours. The resulting slurry was filtered, and the solid was washed with heptane (50 mL, cooled to 0° C.). The resulting solid was dried under vacuum to provide Intermediate 66. ¹H NMR (400 MHz, CDCl₃, δ): 7.97-8.02 (m, 2 H), 7.40 (d, J=8.4 Hz, 2 H), 4.74 (dd, J=7.8, 5.7 Hz, 1 H), 3.90 (s, 3 H), 1.61-1.82 (m, 2 H), 1.23-1.49 (m, 2 H), 0.92 (t, J=7.32 Hz, 3 H).

Intermediate 67

(R)-methyl 4-(1-aminobutyl)benzoate

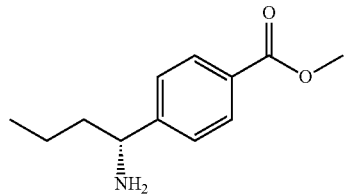

A solution of Intermediate 66 (20.00 g, 96.04 mmol) in tetrahydrofuran (120 mL) was cooled to 5° C. Triethylamine (10.24 g, 101.2 mmol) followed by methanesulfonyl chloride (11.75 g, 102.6 mmol) were added while maintaining the reaction temperature below 20° C. The resulting slurry was filtered, and the solid was washed with tetrahydrofuran (40 mL). To the combined filtrates was added azidotrimethylsilane (18.80 g, 163.2 mmol). A flow system was used with two feed streams, the reaction solution and tetrabutylammonium fluoride (75 wt % in water). The streams were combined at rates such that the instantaneous stoichiometry through the system was maintained at 1.6 equivalents of tetrabutylammonium fluoride relative to Intermediate 66. The combined streams were discharged into a nitrogen-purged reactor precharged with zinc dust (14.6 g, 223.3 mmol) and ammonium formate (14.3 g, 226.8 mmol). The mixture was stirred vigorously until the reaction was complete. The mixture was then filtered, and resulting solid was washed with tetrahydrofuran. The combined filtrates were diluted with saturated aq potassium carbonate (300 mL) and water (900 mL). The layers were separated, and the aqueous layer was extracted with methyl tert-butyl ether (5×700 mL). The combined organics were dried over sodium sulfate and filtered. The filtrate was concentrated under reduced pressure to afford Intermediate 67 as a yellow oil. ¹H NMR (400 MHz, CDCl₃, δ): 8.03-7.98 (m, 2 H), 7.42-7.37 (m, 2 H), 3.97 (t, J=6.9 Hz, 1 H), 3.92 (s, 3 H), 1.73-1.59 (m, 4 H), 1.43-1.20 (m, 2 H), 0.91 (t, J=7.3 Hz, 3 H).

Intermediate 68

(R)-methyl 4-(1-((3-methylquinolin-2-yl)amino) butyl)benzoate

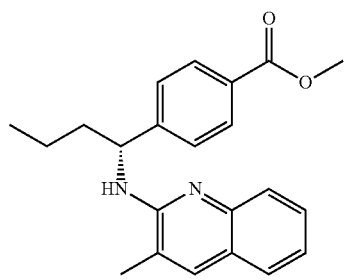 [SMILES: CCC[C@@H](Nc1nc2ccccc2cc1C)c1ccc(C(=O)OC)cc1]

The title compound was prepared by a method analogous to that described for Intermediate 4 using Intermediate 67. ¹H NMR (400 MHz, CDCl₃, δ): 8.01-7.96 (m, 2 H), 7.64-7.59 (m, 2 H), 7.55-7.49 (m, 3 H), 7.43 (ddd, J=8.5, 7.0, 1.5 Hz, 1 H), 7.17 (ddd, J=8.0, 7.0, 1.3 Hz, 1 H), 5.51 (q, J=7.2 Hz, 1 H), 4.79 (d, J=7.2 Hz, 1 H), 3.89 (s, 3 H), 2.30 (d, J=0.8 Hz, 3 H), 2.04-1.82 (m, 2 H), 1.39 (s, 2 H), 1.02-0.94 (m, 3 H).

Intermediate 69

(R)-ethyl 3-(4-(1-((3-methylquinolin-2-yl)amino) butyl)benzamido)propanoate

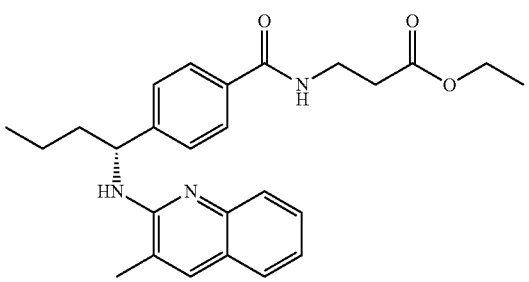 [SMILES: CCC[C@@H](Nc1nc2ccccc2cc1C)c1ccc(C(=O)NCCC(=O)OCC)cc1]

The title compound was prepared by a method analogous to that described for Intermediate 6 using Intermediate 68. ¹H NMR (400 MHz, CDCl₃, δ): 7.73-7.68 (m, 2 H), 7.64-7.59 (m, 2 H), 7.54-7.49 (m, 3 H), 7.43 (ddd, J=8.4, 6.9, 1.5 Hz, 1 H), 7.16 (ddd, J=8.0, 6.9, 1.2 Hz, 1 H), 6.78 (t, J=5.9 Hz, 1 H), 5.48 (q, J=7.2 Hz, 1 H), 4.78 (d, J=7.0 Hz, 1 H), 4.16 (q, J=7.0 Hz, 2 H), 3.71 (q, J=6.0 Hz, 2 H), 2.65-2.58 (m, 2 H), 2.29 (d, J=1.0 Hz, 3 H), 2.04-1.82 (m, 2 H), 1.53-1.30 (m, 2 H), 1.26 (t, J=7.1 Hz, 3 H), 0.97 (t, J=7.4 Hz, 3 H).

Intermediate 70

3-{4-[(3,3-dimethyl-cyclobutyl)-(3-methyl-quinolin-2-ylamino)-methyl]-benzoylamino}-propionic acid methyl ester, isomer 1

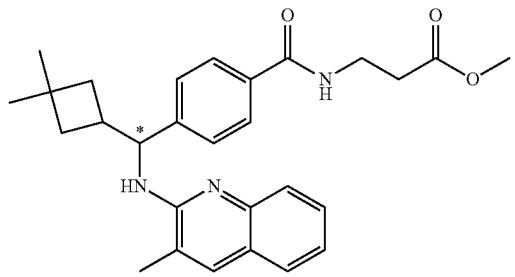

(+/−)-4-[(3,3-dimethyl-cyclobutyl)-(3-methyl-quinolin-2-ylamino)-methyl]-benzoic acid (Intermediate 26, 1.0 eq.), 1-hydrobenzotriazole hydrate (1.2 eq.), N-(3-dimethylaminopropyl)-N'-ethylcarbodiimide hydrochloride (1.2 eq.), beta-alanine methyl ester hydrochloride (1.1 eq.), and triethylamine (1.3 eq.) were combined in anhydrous dichloromethane in a similar manner as described in the experimental for intermediate 27 to provide (+/−)-3-{4-[(3,3-dimethyl-cyclobutyl)-(3-methyl-quinolin-2-ylamino)-methyl]-benzoylamino}-propionic acid methyl ester which was resolved via chiral chromatography to provide the title compound. Preparative chiral SFC: (Chiralpak AD-H column, 21 mm×25 cm, 40% methanol/carbon dioxide eluent, 0.2% isopropylamine modifier, 65.0 mL/min flow rate, 2.71 retention time); ¹H NMR (400 MHz, CDCl₃) δ 7.63-7.69 (m, 2H), 7.58

(t, J=3.9 Hz, 2H), 7.45-7.51 (m, 3H), 7.41 (ddd, J=8.4, 7.0, 1.6 Hz, 1H), 7.14 (ddd, J=8.0, 6.9, 1.2 Hz, 1H), 6.72 (t, J=6.0 Hz, 1H), 5.31 (dd, J=9.7, 6.7 Hz, 1H), 4.75 (d, J=6.8 Hz, 1H), 3.69 (q, J=6.2 Hz, 5H), 2.55-2.71 (m, 3H), 2.28 (d, J=0.8 Hz, 3H), 1.95 (ddd, J=11.2, 8.0, 3.0 Hz, 1H), 1.78 (dd, J=11.1, 9.0 Hz, 1H), 1.64-1.72 (m, 2H), 1.15 (s, 3H), 1.08 (s, 3H); MS (M+1): 460.4.

Intermediate 71

3-{4-[(3,3-dimethyl-cyclobutyl)-(3-methyl-quinolin-2-ylamino)-methyl]-benzoylamino}-propionic acid methyl ester, isomer 2

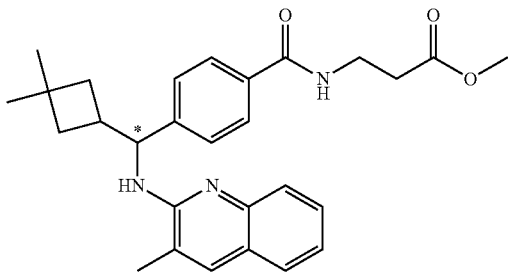

(+/−)-3-{4-[(3,3-dimethyl-cyclobutyl)-(3-methyl-quinolin-2-ylamino)-methyl]-benzoylamino}-propionic acid methyl ester was resolved via chiral chromatography to provide the title compound. Preparative chiral SFC: (Chiralpak AD-H column, 21 mm×25 cm, 40% methanol/carbon dioxide eluent, 0.2% isopropylamine modifier, 65.0 mL/min flow rate, 5.17 retention time); $^1$H NMR (400 MHz, CDCl$_3$) δ 7.67 (d, J=8.0 Hz, 2H), 7.60 (br. s., 2H), 7.46-7.55 (m, 3H), 7.36-7.46 (m, 1H), 7.15 (br. s, 1H), 6.73 (t, J=5.7 Hz, 1H), 5.30 (br. s, 1H), 4.73 (br. s, 1H), 3.62-3.75 (m, 5H), 2.56-2.74 (m, 3H), 2.30 (br. s., 3H), 1.95 (ddd, J=11.2, 8.1, 2.5 Hz, 1H), 1.75-1.88 (m, 1H), 1.61-1.75 (m, 2H), 1.14 (s, 3H), 1.09 (s, 3H); MS (M+1): 460.4.

Intermediate 72

(+/−)-4-[(3,3-dimethyl-cyclobutyl)-(6-fluoro-3-methyl-quinolin-2-ylamino)-methyl]-benzoic acid ethyl ester

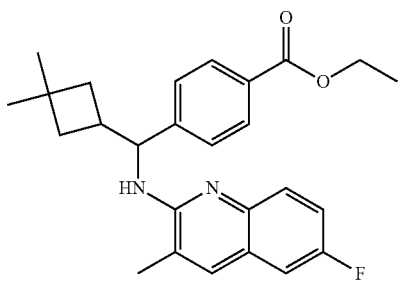 [SMILES: CCOC(=O)c1ccc(C(Nc2nc3ccc(F)cc3cc2C)C2CC(C)(C)C2)cc1]

The title compound was prepared by treating intermediate 29 in a similar manner as described in the experimental for intermediate 25.

Intermediate 73

(+/−)-4-((3,3-dimethylcyclobutyl)((6-fluoro-3-methylquinolin-2-yl)amino)methyl)benzoic acid

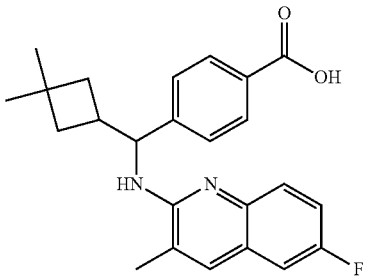 [SMILES: Cc1cc2cc(F)ccc2nc1NC(c1ccc(C(=O)O)cc1)C1CC(C)(C)C1]

The title compound was prepared by treating (+/−)-4-[(3,3-dimethyl-cyclobutyl)-(6-fluoro-3-methyl-quinolin-2-ylamino)-methyl]-benzoic acid ethyl ester (intermediate 72) in a similar as described in the experimental for intermediate 26.

Intermediate 74

3-{4-[(3,3-Dimethyl-cyclobutyl)-(6-fluoro-3-methyl-quinolin-2-ylamino)-methyl]-benzoylamino}-propionic acid methyl ester, isomer 1

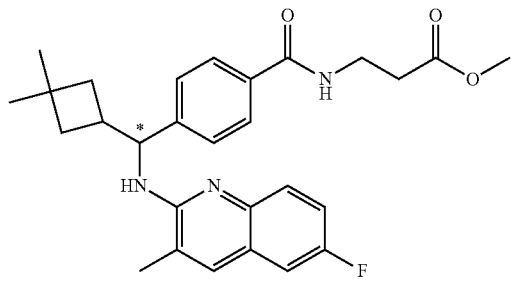

(+/−)-4-((3,3-dimethylcyclobutyl)(6-fluoroquinolin-3-ylamino)methyl)benzoic acid (Intermediate 73, 1.0 eq.), 1-hydrobenzotriazole hydrate (1.2 eq.), N-(3-dimethylaminopropyl)-N'-ethylcarbodiimide hydrochloride (1.2 eq.), beta-alanine methyl ester hydrochloride (1.1 eq.), and triethylamine (1.3 eq.) were combined in anhydrous dichloromethane in a manner similar to that described in the experimental for intermediate 27 to provide (+/−)-3-{4-[(3,3-Dimethyl-cyclobutyl)-(6-fluoro-3-methyl-quinolin-2-ylamino)-methyl]-benzoylamino}-propionic acid methyl ester which was resolved via chiral chromatography to provide the title compound. Preparative chiral SFC: (Chiralpak AD-H column, 10 mm×25 cm, 30% propanol/carbon dioxide eluent, 10.0 mL/min flow rate, 4.16 retention time); $^1$H NMR (400 MHz, CDCl$_3$) δ 7.67 (d, J=8.1 Hz, 2H), 7.50-7.59 (m, 2H), 7.42-7.50 (m, 2H), 7.08-7.22 (m, 2H), 6.65-6.80 (m, 1H), 5.18-5.28 (m, 1H), 4.68-4.75 (m, 1H), 3.62-3.75 (m, 5H), 2.55-2.72 (m, 3H), 2.28 (s, 3H), 1.95 (ddd, J=11.1, 8.1, 3.0 Hz, 1H), 1.73-1.83 (m, 1H), 1.61-1.73 (m, 2H), 1.14 (s, 3H), 1.09 (s, 3H); MS (M+1): 478.3.

Intermediate 75

3-{4-[(3,3-Dimethyl-cyclobutyl)-(6-fluoro-3-methyl-quinolin-2-ylamino)-methyl]-benzoylamino}-propionic acid methyl ester, isomer 2

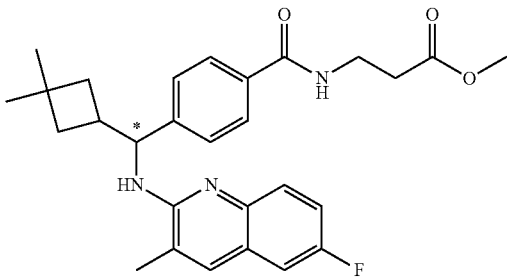

(+/−)-3-{4-[(3,3-Dimethyl-cyclobutyl)-(6-fluoro-3-methyl-quinolin-2-ylamino)-methyl]-benzoylamino}-propionic acid methyl ester was resolved via chiral chromatography to provide the title compound. Preparative chiral SFC: (Chiralpak AD-H column, 10 mm×25 cm, 30% propanol/carbon dioxide eluent, 10.0 ml/min flow rate, 5.88 retention time); $^1$H NMR (400 MHz, CDCl$_3$) δ 7.67 (d, J=7.8 Hz, 2H), 7.51-7.59 (m, 2H), 7.47 (d, J=8.1 Hz, 2H), 7.08-7.22 (m, 2H), 6.66-6.78 (m, 1H), 5.19-5.27 (m, 1H), 4.72 (d, J=5.4 Hz, 1H), 3.62-3.74 (m, 5H), 2.52-2.71 (m, 3H), 2.28 (s, 3H), 1.90-2.00 (m, 1H), 1.71-1.81 (m, 1H), 1.62-1.71 (m, 2H), 1.14 (s, 3H), 1.08 (s, 3H); MS (M+1): 478.3.

Preparation of Compounds of Formula I

Example 1

(+)-3-(4-(1-((3-Methylquinolin-2-yl)amino)butyl)benzamido)propanoic acid

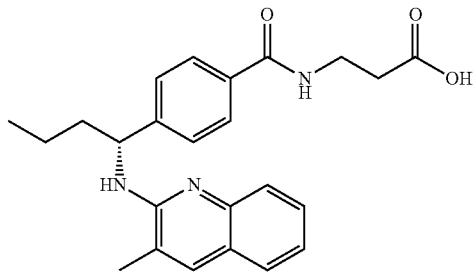 [SMILES: CCC[C@@H](Nc1nc2ccccc2cc1C)c1ccc(C(=O)NCCC(=O)O)cc1]

To a solution of Intermediate 6 (17.66 g, 42.10 mmol) in tetrahydrofuran (210 mL) and methanol (210 mL) was added 1 N aq sodium hydroxide (210 mL). The solution was stirred at room temperature for 10 min. The solution was concentrated under reduced pressure to remove tetrahydrofuran and methanol. 1 N aq hydrochloric acid was added dropwise to pH 4.75. The resulting slurry was filtered, and the solid was washed with water (2×50 mL). The solid was dried in a vacuum oven for 16 h. The resulting solid was slurried in water and ethyl acetate. The mixture was filtered, and the resulting biphasic filtrate was separated. The aqueous layer was extracted with ethyl acetate. The aqueous layer was then used to slurry the filtered solid. The pH was adjusted to 4 with 1 N aq NaOH, then ethyl acetate was added. The process of filtration, separation, extraction, reslurry, and pH adjustment was repeated until no solid remained and thin layer chromatography indicated no remaining product in the aqueous layer. The combined organic layers were concentrated under reduced pressure and dried in a vacuum oven to afford (+)-3-(4-(1-((3-methylquinolin-2-yl)amino)butyl)benzamido) propanoic acid (Example 1). $^1$H NMR (400 MHz, DMSO-d$_6$) δ 12.18 (s, 1H), 8.40 (t, J=5.6 Hz, 1H), 7.74 (d, J=8.4 Hz, 2H), 7.68 (s, 1H), 7.57 (d, J=8.2 Hz, 2H), 7.53 (d, J=7.4 Hz, 1H), 7.45-7.40 (m, 1H), 7.40-7.33 (m, 1H), 7.13-7.06 (m, 1H), 6.62 (br. s., 1H), 5.46-5.35 (m, 1H), 3.48-3.38 (m, 2H), 2.48 (t, J=7.1 Hz, 2H), 2.32 (s, 3H), 2.06-1.93 (m, 1H), 1.85-1.74 (m, 1H), 1.52-1.38 (m, 1H), 1.38-1.23 (m, 1H), 0.92 (t, J=7.3 Hz, 3H); HPLC: XBridge C$_{18}$ 150 mm×4.6 mm, 5 μm column, flow rate 1.50 mL/min, linear gradient of 5% acetonitrile/water (0.1% trifluoroacetic acid modifier) to 100% acetonitrile over 11 min, retention time=6.34 min; MS (M+1): 406.5. An additional preparation of the hydrochloride salt of the compound of Example 1, (+)-3-(4-(1-((3-Methylquinolin-2-yl)amino)butyl)benzamido)propanoic acid hydrochloride salt is as follows:

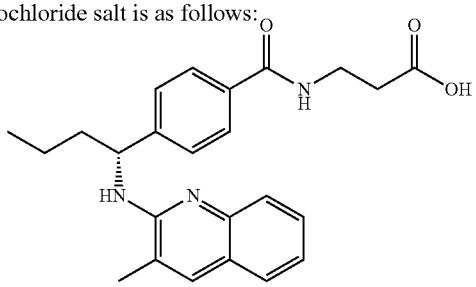

To a solution of Intermediate 69 (33.55 g, 77.38 mmol) in tetrahydrofuran (161 mL) and methanol (161 mL) was added sodium hydroxide (1 N in water, 161 mL, 161 mmol). The solution was stirred 10 minutes then concentrated under reduced pressure to remove tetrahydrofuran and methanol. Hydrochloric acid (1 N in water, 130 mL) was added dropwise with vigorous stirring. After 1.5 hours, the slurry was diluted with sat. aq sodium chloride (600 mL) and extracted with dichloromethane (3×1000 mL). The aqueous layer was then acidified to pH 5 with hydrochloric acid and extracted with dichloromethane (5×500 mL). The combined organic layers were dried over magnesium sulfate and filtered. The filtrate was concentrated under reduced pressure to a sticky yellow solid. $^1$H NMR (400 MHz, DMSO-d$_6$) δ 12.18 (s, 1H), 8.40 (t, J=5.6 Hz, 1H), 7.74 (d, J=8.4 Hz, 2H), 7.68 (s, 1H), 7.57 (d, J=8.2 Hz, 2H), 7.53 (d, J=7.4 Hz, 1H), 7.45-7.40 (m, 1H), 7.40-7.33 (m, 1H), 7.13-7.06 (m, 1H), 6.62 (br. s., 1H), 5.46-5.35 (m, 1H), 3.48-3.38 (m, 2H), 2.48 (t, J=7.1 Hz, 2H), 2.32 (s, 3H), 2.06-1.93 (m, 1H), 1.85-1.74 (m, 1H), 1.52-1.38 (m, 1H), 1.38-1.23 (m, 1H), 0.92 (t, J=7.3 Hz, 3H); HPLC: XBridge C$_{18}$ 150 mm×4.6 mm, 5 μm column, flow rate 1.50 mL/min, linear gradient of 5% acetonitrile/water (0.1% trifluoroacetic acid modifier) to 100% acetonitrile over 11 min, retention time=6.34 min; MS (M+1): 406.5.

To this sticky yellow solid was added dichloromethane (1520 mL). Slight warming of the mixture was required to fully dissolve the solid. Hydrogen chloride (2 M in diethyl ether, 37.7 mL, 75.5 mmol) was added dropwise over 30 minutes. The resulting white slurry was stirred for 10 minutes before filtering. The resulting solid was dried under vacuum. The solid was suspended in water (250 mL) and heated to 60° C. Methanol (280 mL) was added slowly with stirring until all solid dissolved. The solution was allowed to cool to room temperature. After 11 hours, the mixture was cooled to 0° C. over 2 hours. The resulting white solid was filtered, and the solid was dried under vacuum to afford Example 1 hydrochloride salt. Additional solid could be obtained by concentration of the filtrate under vacuum to approximately 300 mL total volume and filtration of the resulting slurry.

Example 2

(−)-3-(4-(1-((3-Methylquinolin-2-yl)amino)butyl)benzamido)propanoic acid

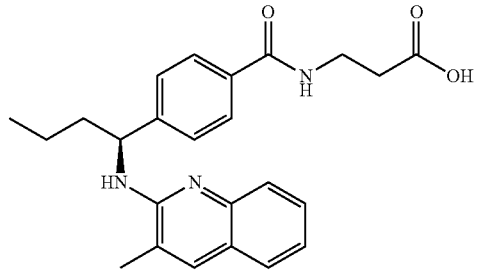 [SMILES: CCC[C@H](Nc1nc2ccccc2cc1C)c1ccc(C(=O)NCCC(=O)O)cc1]

Example 2 was made in an analogous manner to Example 1 from Intermediate 7. $^1$H NMR (400 MHz, DMSO-$d_6$) δ 12.18 (s, 1 H), 8.40 (t, J=5.6 Hz, 1 H), 7.74 (d, J=8.4 Hz, 2 H), 7.68 (s, 1 H), 7.57 (d, J=8.2 Hz, 2 H), 7.53 (d, J=7.4 Hz, 1 H), 7.45-7.40 (m, 1 H), 7.40-7.33 (m, 1 H), 7.13-7.06 (m, 1 H), 6.62 (br. s., 1 H), 5.46-5.35 (m, 1 H), 3.48-3.38 (m, 2 H), 2.48 (t, J=7.1 Hz, 2 H), 2.32 (s, 3 H), 2.06-1.93 (m, 1 H), 1.85-1.74 (m, 1 H), 1.52-1.38 (m, 1 H), 1.38-1.23 (m, 1 H), 0.92 (t, J=7.3 Hz, 3 H); HPLC: XBridge $C_{18}$ 150 mm×4.6 mm, 5 µm column, flow rate 1.50 mL/min, linear gradient of 5% acetonitrile/water (0.1% trifluoroacetic acid modifier) to 100% acetonitrile over 11 min, retention time=6.34 min; MS (M+1): 406.5.

Example 3

(+/−)3-{4-[3-methyl-1-(quinolin-3-ylamino)-butyl]-benzoylamino}-propionic acid

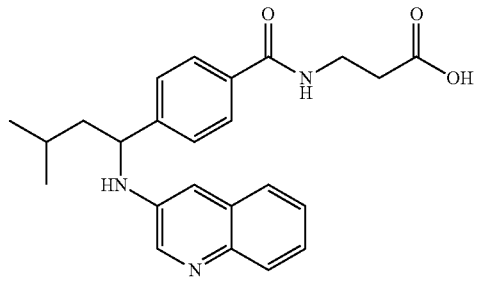 [SMILES: CC(C)CC(Nc1cnc2ccccc2c1)c1ccc(C(=O)NCCC(=O)O)cc1]

Intermediate 12 was dissolved to form a 0.1 M solution in 1,4-dioxane. 3-Bromo-quinoline (100 µmol, 1.0 eq.) was added to an 8 mL vial followed by 1 mL (100 µmol, 1.0 eq.) of the intermediate 12 dioxane solution. To the vial was added sodium tert-butoxide (19 mg, 200 µmol, 2.0 eq.), brettphos-precatalyst (4 mg, 5 µmol, 0.05 eq.), and brettphos (3 mg, 5 µmol, 0.05 eq.). The vial was capped, flushed with nitrogen, and shaken at 80° C. for 16 h. Water (100 µL) was added to the vial to quench the reaction. The dioxane was removed by Speedvac. Saturated aqueous NaHCO$_3$ (2 mL) was added and the resulting mixture extracted with ethyl acetate (2 mL×2). The organic phase was collected, dried over anhydrous Na$_2$SO$_4$, filtered, and the filtrate was concentrated by Speedvac. Purification by reversed-phase HPLC on a DIKMA Diamonsil(2) $C_{18}$ 200×20 mm, 5 µm column eluting with a gradient of acetonitrile in water (0.1% trifluoroacetic acid modifier) gave (+/−)-3-{4-[3-methyl-1-(quinolin-3-ylamino)-butyl]-benzoylamino}-propionic acid. Analytical LCMS: retention time 2.356 minutes (Xbridge $C_{18}$ 2.1×50 mm, 5 µm column; 10% acetonitrile (0.01875% trifluoroacetic acid modifier)/water (0.0375% trifluoroacetic acid modifier) hold for 0.5 minutes, linear gradient to 100% acetonitrile over 3.5 minutes, linear gradient to 10% acetonitrile/water over 0.3 minutes, hold at 10% acetonitrile/water for 0.4 minutes; flow rate 0.8 mL/minute); MS (M+1): 506.

Example 4

(+/−)-3-{4-[1-(7-fluoro-quinazolin-2-ylamino)-3-methyl-butyl]-benzoylamino}-propionic acid

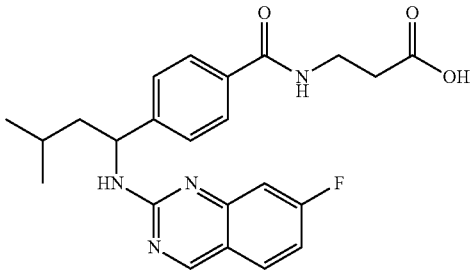 [SMILES: CC(C)CC(Nc1ncc2ccc(F)cc2n1)c1ccc(C(=O)NCCC(=O)O)cc1]

Step A: Intermediate 12 was dissolved to form a 0.1 M solution in DMSO. 2-Chloro-7-fluoro-quinazoline (100 µmol, 1.0 eq.) was added to an 8 mL vial followed by 1 mL (100 µmol, 1.0 eq.) of the intermediate 12 DMSO solution. Diisopropylethylamine (35 µL, 200 µmol, 2.0 eq.) was added and the vial was capped and shaken at 80° C. for 16 h. The solvent was removed by lyophilization and the residue was used in the next step.

Step B: A solution of trifluoroacetic acid in dichloromethane (v/v=1:4) was prepared. 1.0 mL of this solution was added to the vial containing the residue from Step A. The vial was capped and shaken at 30° C. for 2 h. The solvent was removed by Speedvac. Purification by reversed-phase HPLC on an Agella Venusil ASB $C_{18}$ 150×21.2 mm×5 µM column eluting with a gradient of acetonitrile in water (0.225% formic acid modifier) gave (+/−)-3-{4-[1-(7-fluoro-quinazolin-2-ylamino)-3-methyl-butyl]-benzoylamino}-propionic acid. Analytical LCMS: retention time 2.456 minutes (Xbridge $C_{18}$ 2.1×50 mm, 5 µm column; 10% acetonitrile (0.01875% trifluoroacetic acid modifier)/water (0.0375% trifluoroacetic acid modifier) hold for 0.5 minutes, linear gradient to 100% acetonitrile over 3.5 minutes, linear gradient to 10% acetonitrile/water over 0.3 minutes, hold at 10% acetonitrile/water for 0.4 minutes; flow rate 0.8 mL/minute); MS (M+1): 425.

Example 5

(+/−)-3-{4-[3-methyl-1-(quinolin-2-ylamino)-butyl]-benzoylamino}-propionic acid

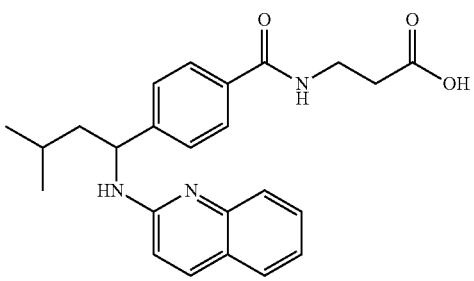

This example was synthesized by analogous procedure to Example 3 by using 2-chloro-quinoline. Purification by reversed-phase HPLC on a Phenomenex Gemini C$_{18}$ 250× 21.2 mm, 8 μm column eluting with a gradient of acetonitrile in NH$_4$OH (pH 10) gave (+/−)-3-{4-[3-methyl-1-(quinolin-2-ylamino)-butyl]-benzoylamino}-propionic acid. Analytical LCMS: retention time 2.263 minutes (Xbridge C$_{18}$ 2.1×50 mm, 5 μm column; 10% acetonitrile (0.01875% trifluoroacetic acid modifier)/water (0.0375% trifluoroacetic acid modifier) hold for 0.5 minutes, linear gradient to 100% acetonitrile over 3.5 minutes, linear gradient to 10% acetonitrile/water over 0.3 minutes, hold at 10% acetonitrile/water for 0.4 minutes; flow rate 0.8 mL/minute); MS (M+1): 406.

Example 6

(+/−)-3-{4-[1-(8-methoxy-quinolin-2-ylamino)-3-methyl-butyl]-benzoylamino}-propionic acid

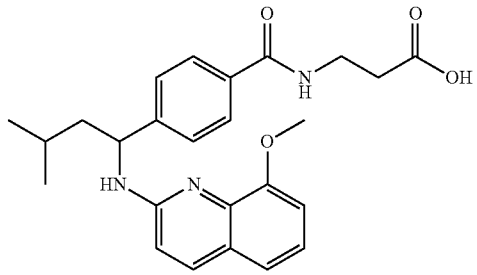 [SMILES: COc1cccc2ccc(NC(CC(C)C)c3ccc(C(=O)NCCC(=O)O)cc3)nc12]

This example was synthesized by analogous procedure to Example 3 by using 2-chloro-8-methoxy-quinoline. Purification by reversed-phase HPLC on a Phenomenex Gemini C$_{18}$ 250×21.2 mm, 8 μm column eluting with a gradient of acetonitrile in NH$_4$OH (pH 10) gave (+/−)-3-{4-[1-(8-methoxy-quinolin-2-ylamino)-3-methyl-butyl]-benzoylamino}-propionic acid. Analytical LCMS: retention time 2.342 minutes (Xbridge C$_{18}$ 2.1×50 mm, 5 μm column; 10% acetonitrile (0.01875% trifluoroacetic acid modifier)/water (0.0375% trifluoroacetic acid modifier) hold for 0.5 minutes, linear gradient to 100% acetonitrile over 3.5 minutes, linear gradient to 10% acetonitrile/water over 0.3 minutes, hold at 10% acetonitrile/water for 0.4 minutes; flow rate 0.8 mL/minute); MS (M+1): 436.

Example 7

(+/−)-3-{4-[3-methyl-1-(quinoxalin-2-ylamino)-butyl]-benzoylamino}-propionic acid

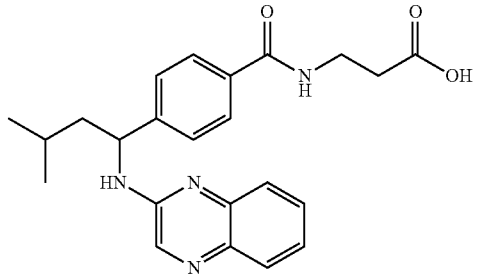

This example was synthesized by analogous procedure to Example 3 by using 2-chloro-quinoxaline. Purification by reversed-phase HPLC on a Phenomenex Gemini C$_{18}$ 250× 21.2 mm, 8 μm column eluting with a gradient of acetonitrile in NH$_4$OH (pH 10) gave (+/−)-3-{4-[3-methyl-1-(quinoxalin-2-ylamino)-butyl]-benzoylamino}-propionic acid. Analytical LCMS: retention time 2.689 minutes (Xbridge C$_{18}$ 2.1×50 mm, 5 μm column; 10% acetonitrile (0.01875% trifluoroacetic acid modifier)/water (0.0375% trifluoroacetic acid modifier) hold for 0.5 minutes, linear gradient to 100% acetonitrile over 3.5 minutes, linear gradient to 10% acetonitrile/water over 0.3 minutes, hold at 10% acetonitrile/water for 0.4 minutes; flow rate 0.8 mL/minute); MS (M+1): 407.

Example 8

(+/−)-3-{4-[3-methyl-1-(3-methyl-quinoxalin-2-ylamino)-butyl]-benzoylamino}-propionic acid

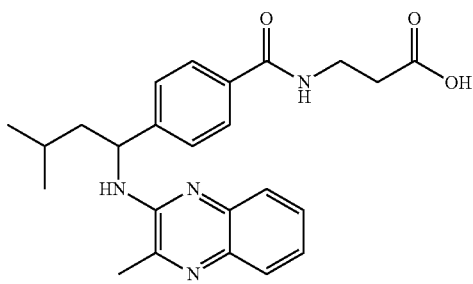 [SMILES: Cc1nc2ccccc2nc1NC(CC(C)C)c1ccc(C(=O)NCCC(=O)O)cc1]

This example was synthesized by analogous procedure to Example 3 by using 2-chloro-3-methyl-quinoxaline. Purification by reversed-phase HPLC on a DIKMA Diamonsil(2) C$_{18}$ 200×20 mm, 5 μm column eluting with a gradient of acetonitrile in water (0.1% trifluoroacetic acid modifier) gave (+/−)-3-{4-[3-methyl-1-(3-methyl-quinoxalin-2-ylamino)-butyl]-benzoylamino}-propionic acid. Analytical LCMS: retention time 2.837 minutes (Xbridge C$_{18}$ 2.1×50 mm, 5 μm column; 10% acetonitrile (0.01875% trifluoroacetic acid modifier)/water (0.0375% trifluoroacetic acid modifier) hold for 0.5 minutes, linear gradient to 100% acetonitrile over 3.5 minutes, linear gradient to 10% acetonitrile/water over 0.3 minutes, hold at 10% acetonitrile/water for 0.4 minutes; flow rate 0.8 mL/minute); MS (M+1): 421.

Example 9

(+/−)-3-{4-[1-(isoquinolin-3-ylamino)-3-methyl-butyl]-benzoylamino}-propionic acid trifluoroacetate

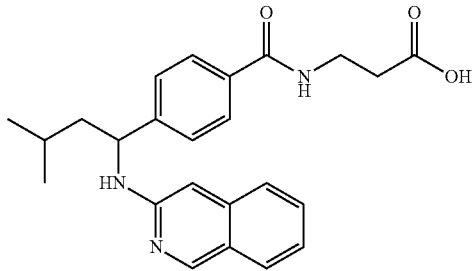 [SMILES: CC(C)CC(Nc1cc2ccccc2cn1)c1ccc(C(=O)NCCC(=O)O)cc1]

This example was synthesized by analogous procedure to Example 3 by using 3-chloro-isoquinoline. Purification by reversed-phase HPLC on a DIKMA Diamonsil(2) C$_{18}$ 200× 20 mm, 5 μM column eluting with a gradient of acetonitrile in water (0.1% trifluoroacetic acid modifier) gave (+/−)-3-{4-[1-(isoquinolin-3-ylamino)-3-methyl-butyl]-benzoylamino}-propionic acid trifluoroacetate. Analytical LCMS: retention time 2.423 minutes (Xbridge C$_{18}$ 2.1×50 mm, 5 μm column; 10% acetonitrile (0.01875% trifluoroacetic acid modifier)/water (0.0375% trifluoroacetic acid modifier) hold for 0.5 minutes, linear gradient to 100% acetonitrile over 3.5 minutes, linear gradient to 10% acetonitrile/water over 0.3 minutes, hold at 10% acetonitrile/water for 0.4 minutes; flow rate 0.8 mL/minute); MS (M+1): 406.

Example 10

(+/−)-3-{4-[3-methyl-1-(4-methyl-quinolin-2-ylamino)-butyl]-benzoylamino}-propionic acid

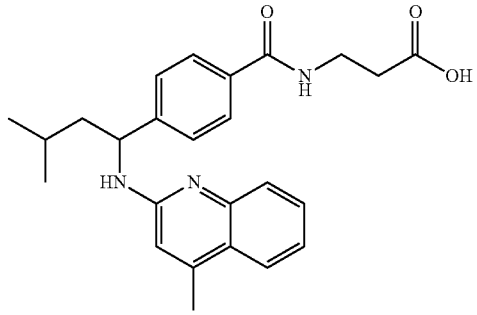 [SMILES: Cc1cc(NC(CC(C)C)c2ccc(C(=O)NCCC(=O)O)cc2)nc2ccccc12]

This example was synthesized by analogous procedure to Example 3 by using 2-chloro-4-methyl-quinoline. Purification by reversed-phase HPLC on a Phenomenex Gemini $C_{18}$ 250×21.2 mm, 10 μm column eluting with a gradient of acetonitrile in $NH_4OH$ (pH 10) gave (+/−)-3-{4-[3-methyl-1-(4-methyl-quinolin-2-ylamino)-butyl]-benzoylamino}-propionic acid. Analytical LCMS: retention time 2.368 minutes (Xbridge $C_{18}$ 2.1×50 mm, 5 μm column; 10% acetonitrile (0.01875% trifluoroacetic acid modifier)/water (0.0375% trifluoroacetic acid modifier) hold for 0.5 minutes, linear gradient to 100% acetonitrile over 3.5 minutes, linear gradient to 10% acetonitrile/water over 0.3 minutes, hold at 10% acetonitrile/water for 0.4 minutes; flow rate 0.8 mL/minute); MS (M+1): 420.

Example 11

(+/−)-3-{4-[3-methyl-1-(3-methyl-quinolin-2-ylamino)-butyl]-benzoylamino}-propionic acid

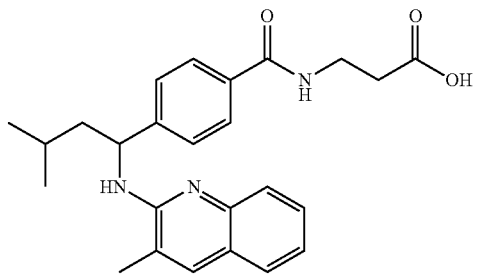 [SMILES: Cc1cc2ccccc2nc1NC(CC(C)C)c1ccc(C(=O)NCCC(=O)O)cc1]

This example was synthesized by analogous procedure to Example 3 by using 2-chloro-3-methyl-quinoline. Purification by reversed-phase HPLC on a Phenomenex Gemini $C_{18}$ 250×21.2 mm, 10 μm column eluting with a gradient of acetonitrile in $NH_4OH$ (pH 10) gave (+/−)-3-{4-[3-methyl-1-(3-methyl-quinolin-2-ylamino)-butyl]-benzoylamino}-propionic acid. Analytical LCMS: retention time 2.326 minutes (Xbridge $C_{18}$ 2.1×50 mm, 5 μm column; 10% acetonitrile (0.01875% trifluoroacetic acid modifier)/water (0.0375% trifluoroacetic acid modifier) hold for 0.5 minutes, linear gradient to 100% acetonitrile over 3.5 minutes, linear gradient to 10% acetonitrile/water over 0.3 minutes, hold at 10% acetonitrile/water for 0.4 minutes; flow rate 0.8 mL/minute); MS (M+1): 420.

Example 12

(+/−)-3-{4-[1-(7-fluoro-4-methyl-quinolin-2-ylamino)-3-methyl-butyl]-benzoylamino}-propionic acid

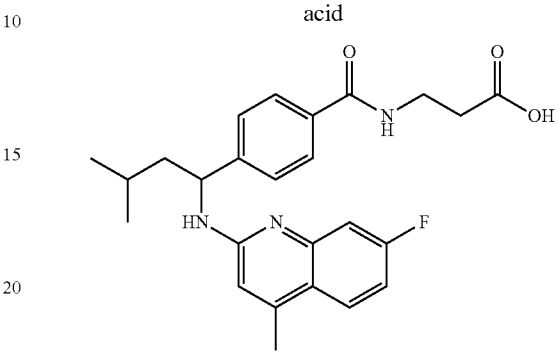

This example was synthesized by analogous procedure to Example 3 by using 2-chloro-7-fluoro-4-methyl-quinoline. Purification by reversed-phase HPLC on a Phenomenex Gemini $C_{18}$ 250×21.2 mm, 8 μm column eluting with a gradient of acetonitrile in $NH_4OH$ (pH 10) gave (+/−)-3-{4-[1-(7-fluoro-4-methyl-quinolin-2-ylamino)-3-methyl-butyl]-benzoylamino}-propionic acid. Analytical LCMS: retention time 2.404 minutes (Xbridge $C_{18}$ 2.1×50 mm, 5 μm column; 10% acetonitrile (0.01875% trifluoroacetic acid modifier)/water (0.0375% trifluoroacetic acid modifier) hold for 0.5 minutes, linear gradient to 100% acetonitrile over 3.5 minutes, linear gradient to 10% acetonitrile/water over 0.3 minutes, hold at 10% acetonitrile/water for 0.4 minutes; flow rate 0.8 mL/minute); MS (M+1): 438.

Example 13

(+/−)-3-{4-[1-(8-chloro-quinolin-2-ylamino)-3-methyl-butyl]-benzoylamino}-propionic acid

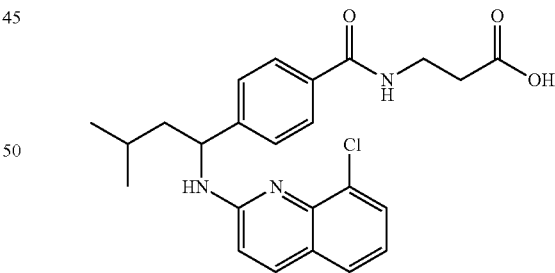

This example was synthesized by analogous procedure to Example 3 by using 2,8-dichloro-quinoline. Purification by reversed-phase HPLC on a Phenomenex Gemini $C_{18}$ 250×21.2 mm, 8 μm column eluting with a gradient of acetonitrile in $NH_4OH$ (pH 10) gave (+/−)-3-{4-[1-(8-chloro-quinolin-2-ylamino)-3-methyl-butyl]-benzoylamino}-propionic acid. Analytical LCMS: retention time 2.462 minutes (Xbridge $C_{18}$ 2.1×50 mm, 5 μm column; 10% acetonitrile (0.01875% trifluoroacetic acid modifier)/water (0.0375% trifluoroacetic acid modifier) hold for 0.5 minutes, linear gradient to 100% acetonitrile over 3.5 minutes, linear gradient to 10% acetonitrile/water over 0.3 minutes, hold at 10% acetonitrile/water for 0.4 minutes; flow rate 0.8 mL/minute); MS (M+1): 440.

Example 14

(+/−)-3-{4-[3-methyl-1-(quinazolin-2-ylamino)-butyl]-benzoylamino}-propionic acid

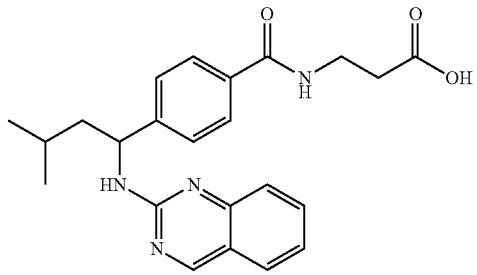

This example was synthesized by analogous procedure to Example 4 by using 2-chloro-quinazoline. Purification by reversed-phase HPLC on a Phenomenex Gemini $C_{18}$ 250× 21.2 mm, 10 μm column eluting with a gradient of acetonitrile in $NH_4OH$ (pH 10) gave (+/−)-3-{4-[3-methyl-1-(quinazolin-2-ylamino)-butyl]-benzoylamino}-propionic acid. Analytical LCMS: retention time 2.401 minutes (Xbridge $C_{18}$ 2.1×50 mm, 5 μm column; 10% acetonitrile (0.01875% trifluoroacetic acid modifier)/water (0.0375% trifluoroacetic acid modifier) hold for 0.5 minutes, linear gradient to 100% acetonitrile over 3.5 minutes, linear gradient to 10% acetonitrile/water over 0.3 minutes, hold at 10% acetonitrile/water for 0.4 minutes; flow rate 0.8 mL/minute); MS (M+1): 407.

Example 15

(+/−) 3-(4-(3-methyl-1-(7-(trifluoromethyl)quinolin-2-ylamino)butyl)benzamido)propanoic acid

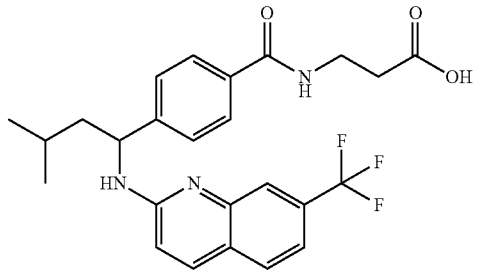 [SMILES: CC(C)CC(Nc1ccc2ccc(C(F)(F)F)cc2n1)c1ccc(C(=O)NCCC(=O)O)cc1]

A 10 mL vial equipped with magnetic stirrer was charged with Intermediate (150 mg, 0.65 mmol), Intermediate 12 (240 mg, 0.72 mmol), 2-(dicyclohexylphosphino)-3,6-dimethoxy-2'-4'-6'-tri-i-propyl-1,1'-biphenyl (17 mg, 0.032 mmol), $Pd(OAc)_2$ (26 mg, 0.032 mmol), sodium t-butoxide (153 mg, 1.37 mmol) and THF (7 mL). The vial was purged with $N_2$, sealed, and heated to 90° C. overnight. The mixture was diluted with water and extracted with ethyl acetate (10 ml*3). The combined organic layers were dried over $Na_2SO_4$, filtered, and evaporated to dryness. The crude product was purified by silica gel chromatography to give (+/−) 3-(4-(3-methyl-1-(7-(trifluoromethyl)quinolin-2-ylamino)butyl) benzamido)propanoic acid (26.5 mg, 8.6%) as a colorless oil. $^1$H NMR (400 MHz, MeOD) δ 7.79 (d, J=8.8 Hz, 1H), 7.64 (m, 4H), 7.44 (d, J=8.4 Hz, 2H), 7.24 (d, J=7.2 Hz, 1H), 6.83 (d, J=8.8 Hz, 1H), 5.29-5.28 (m, 1H), 3.52-3.49 (m, 2H), 2.51-2.48 (m, 2H), 1.8.-1.73 (m, 1H), 1.70-1.64 (m, 1H), 1.59-1.52 (m, 1H), 0.94-0.90 (m, 6H). MS (M+1)=474.2.

Example 16

(+/−) 3-(4-(3-methyl-1-(6-(trifluoromethyl)quinolin-2-ylamino)butyl)benzamido)propanoic acid

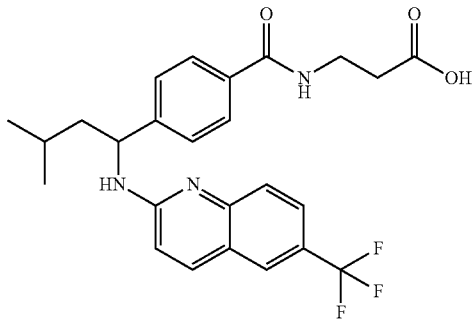 [SMILES: CC(C)CC(Nc1ccc2cc(C(F)(F)F)ccc2n1)c1ccc(C(=O)NCCC(=O)O)cc1]

A 50 mL vial equipped with a magnetic stirrer was charged with Intermediate 17 (150 mg, 0.65 mmol), Intermediate 12 (240 mg, 0.72 mmol), 2-(dicyclohexylphosphino)-3,6-dimethoxy-2'-4'-6'-tri-i-propyl-1,1'-biphenyl (17 mg, 0.032 mmol), $Pd(OAc)_2$ (26 mg, 0.032 mmol), sodium t-butoxide (153 mg, 1.37 mmol) and THF (7 mL). The vial was purged with $N_2$, sealed, and heated at 90° C. overnight. The mixture was diluted with water and extracted with ethyl acetate (10 ml*3). The combined organic layers were dried over $Na_2SO^4$, filtered, and concentrated to dryness. The crude product was purified by silica gel chromatography to give (+/−) 3-(4-(3-methyl-1-(6-(trifluoromethyl)quinolin-2-ylamino)butyl) benzamido)propanoic acid (20 mg, 6.5%) as a colorless solid. $^1$H NMR (400 MHz, $CD_3OD$) δ 7.91 (d, J=8.8 Hz, 2H), 7.75 (d, J=8.0 Hz, 2H), 7.62 (m, 2H), 7.53 (d, J=8.4 Hz, 2H), 6.90 (d, J=8.8 Hz, 2H), 5.40 (br s, 1H), 3.62-3.58 (m, 2H), 2.62-2.58 (s, 2H), 1.89-1.83 (m, 1H), 1.82-1.68 (m, 1H), 1.65-1.62 (m, 1H), 1.04-1.00 (m, 6H). MS (M+1)=474.0.

Example 17

(+\−)-3-(4-(3-methyl-1-(2-methylquinolin-3-ylamino)butyl)benzamido) propanoic acid

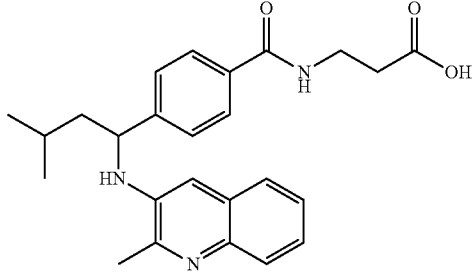 [SMILES: Cc1nc2ccccc2cc1NC(CC(C)C)c1ccc(C(=O)NCCC(=O)O)cc1]

A mixture of Intermediate 18 (200 mg, 1.26 mmol), Intermediate 19 (476 mg) and potassium carbonate (349 mg, 2.53 mmol) in acetonitrile (10 mL) was stirred overnight at 80° C. The reaction mixture was poured into saturated aqueous sodium chloride (20 mL) and extracted with ethyl acetate (2×30 mL). The combined organic layers were washed with brine (2×30 mL) and water (30 mL), then dried over anhydrous $Na_2SO_4$, filtered, and concentrated under reduced pressure. The crude residue was purified by silica gel cromatography to give ethyl 4-(3-methyl-1-(2-methylquinolin-3- ylamino)butyl)benzoate (50 mg, 12%) as a yellow solid. This material was dissolved in methanol (6 mL) and cooled to 0° C. Aqueous 2N sodium hydroxide (6 mL, 12 mmol) was added. The reaction was heated to reflux and stirred for 90 min. The mixture was acidified to pH 3 by addition of 1N aqueous HCl solution and extracted with ethyl acetate (2×30 mL). The combined organic layers were dried over anhydrous Na$_2$SO$_4$, filtered, and concentrated under reduced pressure to give crude 4-(3-methyl-1-(2-methylquinolin-3-ylamino)butyl) benzoic acid (42 mg, 94%) as a yellow solid. The crude acid was dissolved in DMF (6 mL). HATU (114 mg, 0.3 mmol), diisopropylamine (40 mg, 0.3 mmol), and methyl 3-aminopropionate hydrochloride (27 mg, 0.18 mmol) were added sequentially. The resulting mixture was stirred at 30° C. for 1 h. The mixture was poured into brine (20 mL) and extracted with ethyl acetate (2×30 mL). The combined organic layers were dried over anhydrous Na$_2$SO$_4$, filtered, and concentrated under reduced pressure to give crude methyl 3-(4-(3-methyl-1-(2-methylquinolin-3-ylamino)butyl)benzamido) propanoate (55 mg, 98%) as an oil. The crude ester was dissolved in THF (4 mL) and cooled to 0° C. 2 N aqueous lithium hydroxide (4 mL, 8 mmol) was added. The reaction mixture was stirred at 30° C. for 12 h. The mixture was acidified to pH 3 by addition of aqueous 1N HCl. The mixture was extracted with ethyl acetate (2×30 mL). The combined organic layers were dried over anhydrous Na$_2$SO$_4$, filtered, and concentrated. Purification by preparative HPLC on a Phenomenex Synergi C$_{18}$ 150×30 mm×4 μm column eluting with 22% to 42% acetonitrile in water (0.225% formic acid modifier) provided (+\-)-3-(4-(3-methyl-1-(2-methylquinolin-3-ylamino)butyl)benzamido)propanoic acid (17.2 mg) as a yellow solid. $^1$H NMR (400 MHz, CD$_3$OD): δ 7.76-7.78 (m, 3H), 7.57 (d, J=8.0 Hz, 2H), 7.50-7.52 (m, 1H), 7.40-7.35 (m, 2H), 7.03 (s, 1H), 4.69-4.65 (m, 1H), 3.62-3.58 (m, 2H), 2.75 (s, 3H), 2.59-2.62 (m, 2H), 2.03-1.97 (m, 1H), 1.86-1.83 (m, 1H), 1.72-1.66 (m, 1H), 1.07 (d, J=6.4 Hz, 3H), 1.00 (d, J=6.4 Hz, 3H). MS (M+1)=420.1.

Example 18

(+\-)-3-(4-(3-methyl-1-(4-methylquinolin-3-ylamino)butyl)benzamido) propanoic acid

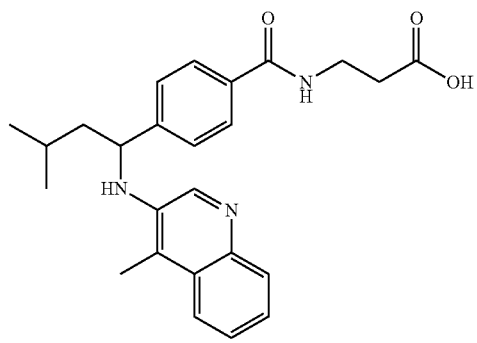 [SMILES: Cc1c(NC(CC(C)C)c2ccc(C(=O)NCCC(=O)O)cc2)cnc2ccccc12]

To a 0° C. solution of Intermediate 21 (40 mg, 0.11 mmol) in methanol (4 mL) was added 2N aqueous sodium hydroxide (4 mL, 8 mmol). The reaction mixture was heated to reflux and stirred for 1.5 h. The mixture was acidified to pH 3 by addition of 1N aqueous HCl and extracted twice with ethyl acetate (30 mL). The combined organic layers were dried over anhydrous Na$_2$SO$_4$, filtered, and concentrated to give a yellow solid, which was dissolved in DMF (5 mL). HATU (98 mg, 0.25 mmol), diisopropylethylamine (32 mg, 0.25 mmol), and methyl 3-aminopropionate hydrochloride (22 mg, 0.15 mmol) were added. The resulting mixture was stirred at 30° C. for 1 hour. The mixture was poured into brine (20 mL) and extracted twice with ethyl acetate (30 mL). The combined organic layers were dried over anhydrous Na$_2$SO$_4$, filtered, and concentrated to give 50 mg of an oil which was dissolved in THF (4 mL). 2N aqueous lithium hydroxide (4 mL, 8 mmol) was added. The reaction mixture was stirred at 30° C. for 12 h. The mixture was acidified to pH 3 by addition of 1N aqueous HCl and extracted with ethyl acetate (30 mL*2). The combined organic layers were dried over anhydrous Na$_2$SO$_4$, filtered, and concentrated. HPLC purification on a Phenomenex Synergi C$_{18}$ 150×30 mm×4 μm column eluting with 49% to 69% acetonitrile in water (0.225% formic acid modifier) provided 3-(4-(3-methyl-1-(4-methylquinolin-3-ylamino)butyl)benzamido)propanoic acid (12.2 mg) as a yellow solid. $^1$H NMR (400 MHz, CD$_3$OD) δ 8.26 (s, 1H), 8.02 (d, J=8.4 Hz, 1H), 7.74-7.77 (m, 3H), 7.54-7.45 (m, 4H), 4.82-4.78 (m, 1H), 3.57-3.61 (m, 2H), 2.58-2.62 (m, 5H), 2.03-1.97 (m, 1H), 1.86-1.83 (m, 1H), 1.73-1.68 (m, 1H), 1.07 (d, J=6.4 Hz, 3H), 1.00 (d, J=6.4 Hz, 3H). MS (M+1) =420.1.

Example 19

(+/-)-3-{4-[(3,3-dimethyl-cyclobutyl)-(3-methyl-quinolin-2-ylamino)-methyl]-benzoylamino}-propionic acid

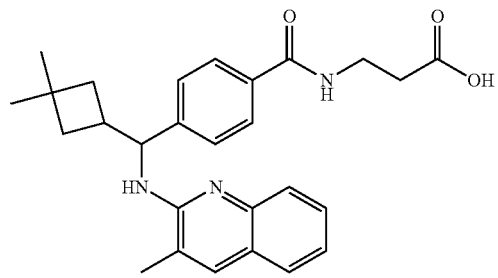 [SMILES: Cc1cc2ccccc2nc1NC(c1ccc(C(=O)NCCC(=O)O)cc1)C1CC(C)(C)C1]

(+/-)-3-{4-[(3,3-dimethyl-cyclobutyl)-(3-methyl-quinolin-2-ylamino)-methyl]-benzoylamino}-propionic acid ethyl ester (Intermediate 27) (36 mg, 0.076 mmol) was dissolved in tetrahydrofuran (3 mL) and methanol (1 mL), and 1.0 M sodium hydroxide (2 mL) was added. This was stirred as a solution at room temperature for 45 min before 1 N HCl was added to bring to pH 4.5. This was extracted twice with ethyl acetate and the combined organics dried over MgSO$_4$. The solution was concentrated in vacuo to give (+/-)-3-{4-[(3,3-dimethyl-cyclobutyl)-(3-methyl-quinolin-2-ylamino)-methyl]-benzoylamino}-propionic acid (40.8 mg) as a white solid impure with ethyl acetate. MS (M+1): 446.3. HPLC: XBridge C$_{18}$ 150 mm×4.6 mm, 5 μm column, flow rate 1.50

Example 20

(+/−)-3-{4-[(3,3-dimethyl-cyclobutyl)-(6-fluoro-3-methyl-quinolin-2-ylamino)-methyl]-benzoylamino}-propionic acid

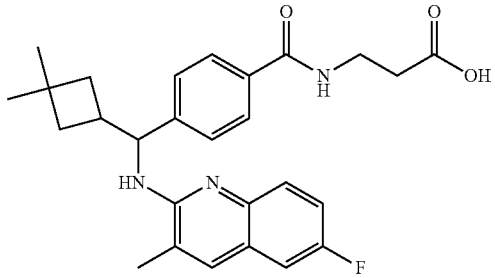 [SMILES: Cc1cc2cc(F)ccc2nc1NC(c1ccc(C(=O)NCCC(=O)O)cc1)C1CC(C)(C)C1]

(+/−)-3-{4-[(3,3-Dimethyl-cyclobutyl)-(6-fluoro-3-methyl-quinolin-2-ylamino)-methyl]-benzoylamino}-propionic acid ethyl ester (14.3 mg, 0.029 mmol), made in a similar manner as Intermediate 27 from Intermediate 29, was dissolved in tetrahydrofuran (1.5 mL) and methanol (0.5 mL), and 1.0 M sodium hydroxide (1 mL) was added. This was stirred as a solution at room temperature for 20 min before 1 N HCl was added to bring to pH 5. This was extracted twice with ethyl acetate and the combined organics dried over MgSO$_4$, and concentrated in vacuo. Purification by reversed-phase HPLC gave (+/−)-3-{4-[(3,3-dimethyl-cyclobutyl)-(6-fluoro-3-methyl-quinolin-2-ylamino)-methyl]-benzoylamino}-propionic acid (10 mg). Analytical LCMS: retention time 2.3998 minutes (Waters Atlantic dC$_{18}$ 4.6×50 mm, 5 μm column; 5% acetonitrile/water (0.05% trifluoroacetic acid modifier) linear gradient to 95% acetonitrile/water over 4.0 minutes, hold at 95% acetonitrile/water for 1.0 minute; flow rate 2.0 mL/minute); MS (M+1): 464.0.

Example 21

(+/−)-3-{4-[(3,3-dimethyl-cyclobutyl)-(7-fluoro-3-methyl-quinolin-2-ylamino)-methyl]-benzoylamino}-propionic acid

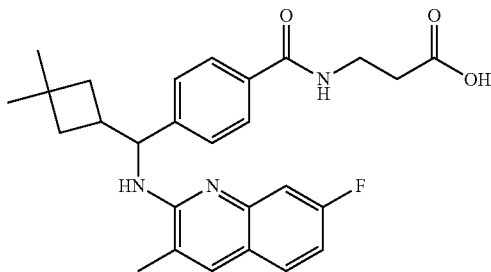 [SMILES: Cc1cc2ccc(F)cc2nc1NC(c1ccc(C(=O)NCCC(=O)O)cc1)C1CC(C)(C)C1]

Example 21 was made in analogous manner to Example 20 from Intermediate 31. Purification by reversed-phase HPLC gave (+/−)-3-{4-[(3,3-dimethyl-cyclobutyl)-(7-fluoro-3-methyl-quinolin-2-ylamino)-methyl]-benzoylamino}-propionic acid (9.6 mg). Analytical LCMS: retention time 2.4302 minutes (Waters Atlantic dC$_{18}$ 4.6×50 mm, 5 μm column; 5% acetonitrile/water (0.03% NH$_4$OH modifier) linear gradient to 95% acetonitrile/water over 4.0 minutes, hold at 95% acetonitrile/water for 1.0 minute; flow rate 2.0 mL/minute); MS (M+1): 464.0.

Example 22

(+/−) 3-(4-((3,3-dimethylcyclobutyl)(7-fluoroquinolin-3-ylamino)methyl)benzamido)propanoic acid

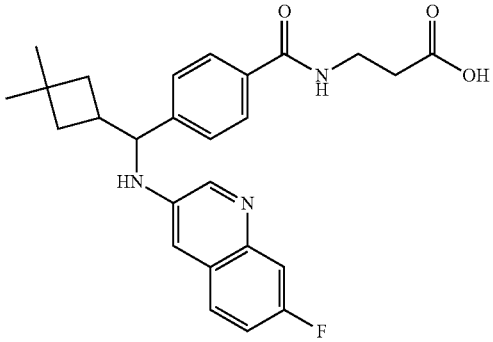 [SMILES: CC1(C)CC(C(Nc2cnc3cc(F)ccc3c2)c2ccc(C(=O)NCCC(=O)O)cc2)C1]

To a flask containing ethyl 3-(4-((3,3-dimethylcyclobutyl)(7-fluoroquinolin-3-ylamino)methyl)benzamido)propanoate (6.20 mg, 0.0130 mmol) was added tetrahydrofuran (0.0330 mL), methanol (0.0330 mL), and 1 N sodium hydroxide (0.0330 mL, 0.0330 mmol). The reaction was stirred for 18 h at room temperature. The reaction was then diluted with ethyl acetate and water. 1 N hydrochloric acid (0.0330 mL) was then added dropwise to bring the pH to 3. The aqueous layer was extracted three times with ethyl acetate. The combined organic layers were dried with sodium sulfate, filtered, and concentrated to provide 3-(4-((3,3-dimethylcyclobutyl)(7-fluoroquinolin-3-ylamino)methyl)benzamido)propanoic acid (3.5 mg, 60% yield) as a solid. $^1$H NMR (400 MHz, CD$_3$OD, δ): 8.53 (d, J=2.7 Hz, 1H), 8.45 (t, J=5.7 Hz, 1H), 7.80-7.72 (m, 2H), 7.59-7.51 (m, 3H), 7.43 (dd, J=10.0, 2.6 Hz, 1H), 7.23 (td, J=8.8, 2.5 Hz, 1H), 6.99 (d, J=2.5 Hz, 1H), 4.38 (d, J=9.6 Hz, 1H), 3.67-3.57 (m, 2H), 2.67-2.60 (m, 3H), 2.16-2.06 (m, 1H), 1.78 (d, J=2.5 Hz, 2H), 1.63-1.52 (m, 1H), 1.18 (s, 3H), 1.13 (s, 3H). (M+1): 450.3.

Example 23

(+/−) 3-(4-((3,3-dimethylcyclobutyl)(6-fluoroquinolin-3-ylamino)methyl)benzamido)propanoic acid

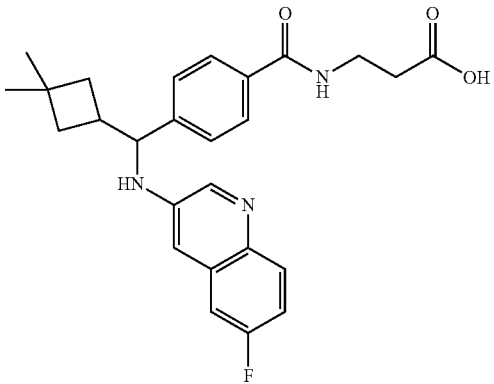 [SMILES: CC1(C)CC(C(Nc2cnc3ccc(F)cc3c2)c2ccc(C(=O)NCCC(=O)O)cc2)C1]

To a flask containing ethyl 3-(4-((3,3-dimethylcyclobutyl)(6-fluoroquinolin-3-ylamino)methyl)benzamido)propanoate (7.4 mg, 0.0420 mmol) was added tetrahydrofuran (0.105 mL), methanol (0.105 mL), and 1 N sodium hydroxide (0.105 mL, 0.105 mmol). The reaction was stirred for 4.5 h at room temperature. The reaction was then diluted with ethyl acetate and water. 1 N hydrochloric acid (0.105 mL) was then added dropwise to bring the pH to 3. The aqueous layer was extracted three times with ethyl acetate. The combined organic layers were dried with sodium sulfate, filtered, and concentrated to provide 3-(4-((3,3-dimethylcyclobutyl)(6-fluoroquinolin-3-ylamino)methyl)benzamido)propanoic acid (6.7 mg, 99% yield) as a solid. $^1$H NMR (400 MHz, CD$_3$OD, δ): 8.46 (d, J=2.7 Hz, 1H), 7.83-7.72 (m, 3H), 7.57-7.50 (m, 2H), 7.17-7.09 (m, 2H), 6.85 (d, J=2.7 Hz, 1H), 4.38 (d, J=9.8 Hz, 1H), 3.62 (t, J=6.9 Hz, 2H), 2.69-2.54 (m, 3H), 2.11 (ddd, J=11.4, 7.7, 4.2 Hz, 1H), 1.77 (ddd, J=11.2, 9.0, 2.6 Hz, 2H), 1.63-1.52 (m, 1H), 1.18 (s, 3H), 1.13 (s, 3H). (M+1): 450.3.

Example 24

3-(4-((3,3-dimethylcyclobutyl)(quinolin-3-ylamino)methyl)benzamido) propanoic acid

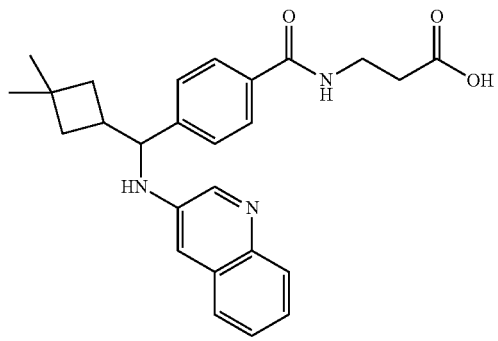 [SMILES: CC1(C)CC(C(Nc2cnc3ccccc3c2)c2ccc(C(=O)NCCC(=O)O)cc2)C1]

To a flask containing ethyl 3-(4-((3,3-dimethylcyclobutyl)(quinolin-3-ylamino)methyl)benzamido)propanoate (11.9 mg, 0.0650 mmol) was added tetrahydrofuran (0.0650 mL), methanol (0.0650 mL), and 1 N sodium hydroxide (0.0650 mL, 0.0650 mmol). The reaction was stirred for 18 h at room temperature. The reaction was then diluted with ethyl acetate and water. 1 N hydrochloric acid (0.0650 mL) was then added dropwise to bring the pH to 3. The aqueous layer was extracted three times with ethyl acetate. The combined organic layers were dried with sodium sulfate, filtered, and concentrated to provide 3-(4-((3,3-dimethylcyclobutyl)(quinolin-3-ylamino)methyl)benzamido)propanoic acid (9.3 mg, 83% yield) as a solid. $^1$H NMR (400 MHz, CD$_3$OD) δ: 8.50 (d, J=2.7 Hz, 1H), 8.45 (t, J=5.8 Hz, 1H), 7.81-7.70 (m, 3H), 7.61-7.52 (m, 2H), 7.52-7.41 (m, 1H), 7.41-7.21 (m, 2H), 6.93 (d, J=2.7 Hz, 1H), 4.39 (d, J=9.8 Hz, 1H), 3.69-3.55 (m, 2H), 2.71-2.51 (m, 3H), 2.11 (ddd, J=11.4, 7.8, 4.1 Hz, 1H), 1.85-1.70 (m, 2H), 1.57 (ddd, J=11.3, 7.8, 4.1 Hz, 1H), 1.18 (s, 3H), 1.13 (s, 3H). MS (M+1): 432.3.

Example 25

3-{4-[3-Methyl-1-(8-methyl-quinolin-3-ylamino)-butyl]-benzoylamino}propionic acid

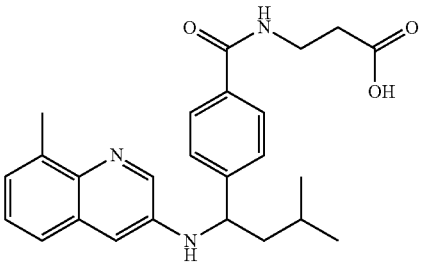 [SMILES: Cc1cccc2cc(NC(CC(C)C)c3ccc(C(=O)NCCC(=O)O)cc3)cnc12]

To a mixture of 3-{4-[3-Methyl-1-(8-methyl-quinolin-3-ylamino)-butyl]-benzoylamino}-propionic acid methyl ester (44 mg, 0.1 mM) in 1:1 mixture of THF/MeOH (1 mL) was added 1N NaOH solution (0.25 mL, 0.25 mM). The reaction mixture was stirred at RT for 1 h. The reaction mixture was concentrated to remove organic solvent. The aqueous solution was diluted with DCM (5 mL), acidified by 1N HCl solution to pH=3-4. The organic solution was separated and the aqueous solution was extracted with 10% i-PrOH-DCM (3×5 mL). The combined organic solution were dried (Na$_2$SO$_4$) and concentrated to give a yellow solid product (~100%). $^1$H NMR (500 MHz, DMSO-d$_6$) δ ppm 0.93 (d, J=6.59 Hz, 3 H) 0.98 (d, J=6.34 Hz, 3 H) 1.56 (dt, J=13.30, 6.77 Hz, 1 H) 1.71 (dt, J=13.36, 6.62 Hz, 1 H) 1.76-1.85 (m, 1 H) 2.46 (t, J=7.07 Hz, 2 H) 2.59 (s, 3 H) 3.36-3.46 (m, 2 H) 4.64 (t, J=7.07 Hz, 1 H) 7.10 (br. s., 1 H) 7.21 (br. s., 1 H) 7.26 (d, J=6.83 Hz, 1 H) 7.32 (t, J=7.56 Hz, 1 H) 7.45 (d, J=8.05 Hz, 1 H) 7.53 (d, J=8.05 Hz, 2 H) 7.76 (d, J=8.29 Hz, 2 H) 8.42 (t, J=5.49 Hz, 1 H) 8.60 (d, J=2.44 Hz, 1 H), one proton was exchanged. LC-MS: 420.2 (M+1).

Example 26

3-{4-[3-Methyl-1-(7-methyl-quinolin-3-ylamino)-butyl]-benzoylamino}-propionic acid

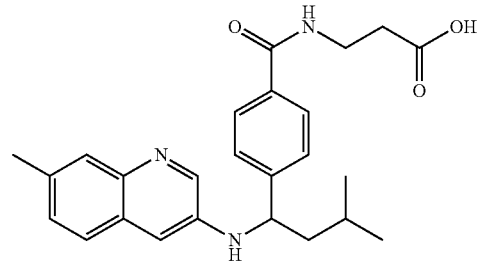 [SMILES: Cc1ccc2cc(NC(CC(C)C)c3ccc(C(=O)NCCC(=O)O)cc3)cnc2c1]

To a mixture of 3-{4-[3-Methyl-1-(8-methyl-quinolin-3-ylamino)-butyl]-benzoylamino}-propionic acid methyl ester (12) (49 mg, 0.11 mM) in 1:1 mixture of THF/MeOH (1 mL) was added 1N NaOH solution (0.283 mL, 0.283 mM). The reaction mixture was stirred at RT for 1 h. The reaction mixture was concentrated to remove organic solvent. The aqueous solution was diluted with DCM (5 mL), acidified by 1N HCl solution to pH=3-4. The organic solution was separated and the aqueous solution was extracted with 10% i-PrOH-DCM (3×5 mL). The combined organic solution were dried (Na$_2$SO$_4$) and concentrated to give a yellow solid product (~78%). ¹H NMR (500 MHz, DMSO-d₆) δ ppm 0.93 (d, J=6.59 Hz, 3H) 0.98 (d, J=6.59 Hz, 3 H) 1.53-1.60 (m, 1 H) 1.70 (dt, J=13.72, 6.68 Hz, 1 H) 1.76-1.83 (m, 1 H) 2.43 (s, 3 H) 2.47 (t, J=7.07 Hz, 2 H) 3.35-3.46 (m, 2 H) 4.65 (t, 1 H) 7.23 (br. s., 1 H) 7.37 (d, J=8.54 Hz, 1 H) 7.41 (br. s., 1 H) 7.54 (d, J=8.29 Hz, 2 H) 7.59-7.67 (m, 2 H) 7.76 (d, J=8.29 Hz, 2 H) 8.43 (t, J=5.49 Hz, 1 H) 8.61 (d, J=2.68 Hz, 1 H), one proton was exchanged. LC-MS: m/z 420.2 (M+1).

Example 27

N-(4-{3-methyl-1-[(6-methylquinolin-3-yl)amino]butyl}benzoyl)-beta-alanine

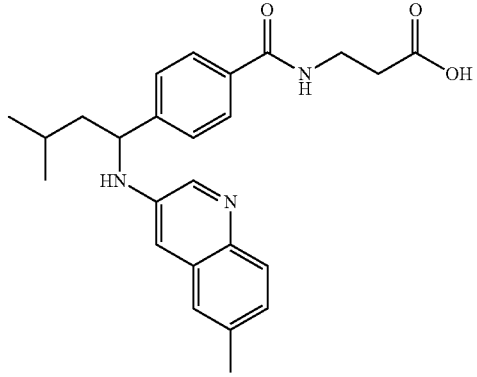 [SMILES: Cc1ccc2ncc(NC(CC(C)C)c3ccc(C(=O)NCCC(=O)O)cc3)cc2c1]

Prepared analogous to 3-{4-[3-Methyl-1-(8-methylquinolin-3-ylamino)-butyl]-benzoylamino}-propionic acid, Example 25, using 3-bromo-6-methylquinoline. m/z (M+1)=420.2.

Example 28

3-(4-((6,7-difluoroquinolin-3-ylamino)(3,3-dimethylcyclobutyl)methyl)benzamido)propanoic acid

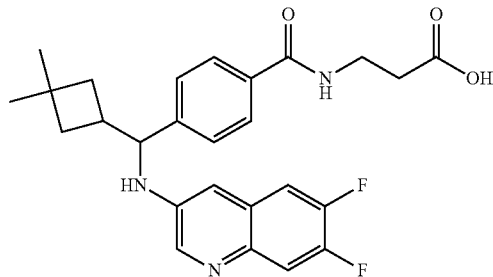 [SMILES: CC1(C)CC(C(Nc2cnc3cc(F)c(F)cc3c2)c2ccc(C(=O)NCCC(=O)O)cc2)C1]

The title compound can be prepared in a manner analogous to Example 27.

Example 29

(+/−)-3-(4-(4,4,4-trifluoro-1-(quinolin-3-ylamino)butyl)benzamido)propanoic acid

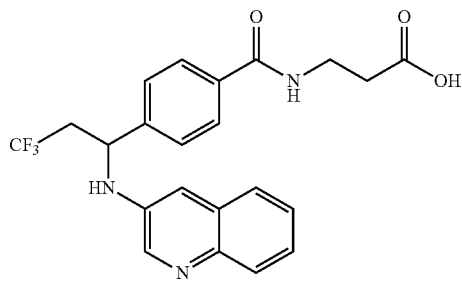 [SMILES: O=C(O)CCNC(=O)c1ccc(C(CC(F)(F)F)Nc2cnc3ccccc3c2)cc1]

To a solution of ethyl (+/−)-3-(4-(4,4,4-trifluoro-1-(quinolin-3-ylamino)butyl)benzamido)propanoate (74 mg, 0.16 mmol) in methanol (0.78 mL) and tetrahydrofuran (0.78 mL) was added 1 N aq sodium hydroxide (0.78 mL, 0.78 mmol). After 10 minutes, the solution was concentrated under reduced pressure to remove methanol and tetrahydrofuran. The mixture was then acidified to pH 4 with 1 N aq hydrochloric acid and diluted with sat. aq sodium chloride (10 mL). The aqueous layer was extracted with ethyl acetate (3×15 mL). The combined organic layers were dried over Na₂SO₄ and filtered, and the filtrate was concentrated under reduced pressure to give (+/−)-3-(4-(4,4,4-trifluoro-1-(quinolin-3-ylamino)butyl)benzamido)propanoic acid. ¹HNMR (400 MHz, DMSO-d₆) δ 12.18 (br. s., 1 H), 8.56 (d, J=2.7 Hz, 1 H), 8.44 (t, J=5.6 Hz, 1 H), 7.78 (d, J=8.4 Hz, 2 H), 7.76-7.72 (m, 1 H), 7.54 (d, J=8.2 Hz, 2 H), 7.52-7.48 (m, 1 H), 7.37-7.27 (m, 2 H), 7.03 (d, J=7.8 Hz, 1 H), 6.86 (d, J=2.5 Hz, 1 H), 4.73-4.61 (m, 1 H), 3.46-3.37 (m, 2 H), 2.47 (t, J=7.0 Hz, 2 H), 2.39-2.23 (m, 1 H), 2.14-1.92 (m, 2 H), 1.20-1.13 (m, 1 H); (M+1): 446.2.

Example 30

3-(4-(3-methyl-1-((3-methylquinolin-2-yl)amino)butyl)benzamido)propanoic acid, Isomer 1

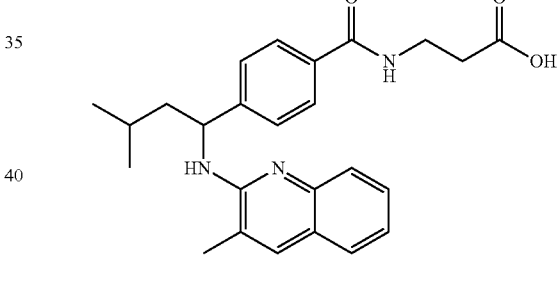

To a solution of ethyl 3-(4-(1-((3-methylquinolin-2-yl)amino)butyl)benzamido) propanoate, isomer 1 (96.2 mg, 0.215 mmol) in tetrahydrofuran (1.1 mL) and methanol (1.1 mL) was added 1 N aq sodium hydroxide (1.1 mL, 1.1 mmol). The solution was stirred at room temperature for 10 min. The solution was concentrated under reduced pressure to remove tetrahydrofuran and methanol. 1 N aq hydrochloric acid was added dropwise to pH 6. The aqueous layer was extracted with ethyl acetate (4×5 mL). The combined organic layers were concentrated under reduced pressure and dried in a vacuum oven to afford 3-(4-(3-methyl-1-((3-methylquinolin-2-yl)amino)butyl)benzamido)propanoic acid as a single isomer. ¹H NMR (400 MHz, DMSO-d₆) δ 8.67-8.57 (m, 1 H), 7.73-7.66 (m, 3 H), 7.59-7.51 (m, 3 H), 7.45-7.40 (m, 1 H), 7.39-7.32 (m, 1 H), 7.09 (ddd, J=7.9, 6.7, 1.4 Hz, 1 H), 6.61 (d, J=8.6 Hz, 1 H), 5.56-5.45 (m, 1 H), 3.40-3.33 (m, 2 H), 2.34-2.25 (m, 5 H), 2.01-1.90 (m, 1 H), 1.71-1.57 (m, 1 H), 0.96 (d, J=6.4 Hz, 3 H), 0.91 (d, J=6.2 Hz, 3 H); analytical chiral SFC (Chiralpak AD-H column, 4.6 mm×25 cm, 25% methanol/carbon dioxide eluent, 0.2% isopropylamine modifier, 3.75 min retention time); MS (M+1): 420.3.

Example 31

3-(4-(3-methyl-1-((3-methylquinolin-2-yl)amino)butyl)benzamido)propanoic acid, Isomer 2

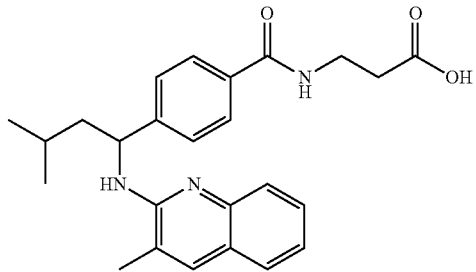 [SMILES: Cc1cc2ccccc2nc1NC(CC(C)C)c1ccc(C(=O)NCCC(=O)O)cc1]

3-(4-(3-methyl-1-((3-methylquinolin-2-yl)amino)butyl)benzamido)propanoic acid, isomer 2 was prepared by a method analogous to Example 30 from 3-(4-(1-((3-methylquinolin-2-yl)amino)butyl)benzamido)propanoate methyl and ethyl ester mixture, isomer 2. $^1$H NMR (400 MHz, DMSO-$d_6$) δ 8.86-8.76 (m, 1 H), 7.73-7.65 (m, 3 H), 7.59-7.49 (m, 3 H), 7.45-7.39 (m, 1 H), 7.39-7.33 (m, 1 H), 7.09 (ddd, J=8.0, 6.7, 1.2 Hz, 1 H), 6.61 (d, J=8.0 Hz, 1 H), 5.56-5.45 (m, 1 H), 3.36-3.29 (m, 2 H), 2.30 (d, J=1.0 Hz, 3 H), 2.17 (t, J=6.9 Hz, 2 H), 2.01-1.90 (m, 1 H), 1.71-1.57 (m, 2 H), 0.96 (d, J=6.5 Hz, 3 H), 0.91 (d, J=6.3 Hz, 3 H); analytical chiral SFC (Chiralpak AD-H column, 4.6 mm×25 cm, 25% methanol/carbon dioxide eluent, 0.2% isopropylamine modifier, 4.81 min retention time); MS (M+1): 420.3.

Example 32

3-{4-[(3,3-dimethyl-cyclobutyl)-(3-methyl-quinolin-2-ylamino)-methyl]-benzoylamino}-propionic acid, isomer 1

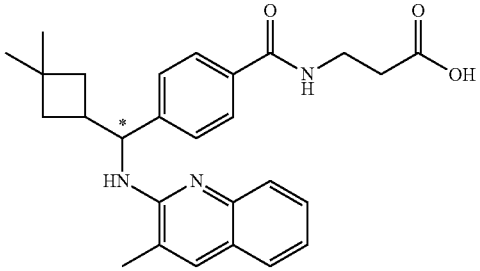 [SMILES: Cc1cc2ccccc2nc1NC(c1ccc(C(=O)NCCC(=O)O)cc1)C1CC(C)(C)C1]

The title compound was prepared by treating 3-{4-[(3,3-dimethyl-cyclobutyl)-(3-methyl-quinolin-2-ylamino)-methyl]-benzoylamino}-propionic acid methyl ester, isomer 1 (intermediate 70) with 1N NaOH (2.5 eq.) in methanol/THF in a similar manner as described in Example 19 to provide the title compound. Analytical chiral SFC: (Chiralpak AD-H column, 4.6 mm×25 cm, 30% methanol/carbon dioxide eluent, 2.5 mL/min flow rate, 2.78 retention time); $^1$H NMR (400 MHz, CDCl$_3$) δ 7.66 (d, J=8.4 Hz, 2H), 7.56-7.63 (m, 2H), 7.44-7.52 (m, 3H), 7.37-7.44 (m, 1H), 7.11-7.19 (m, 1H), 5.30 (d, J=9.8 Hz, 1H), 3.67 (q, J=5.9 Hz, 2H), 2.62-2.70 (m, 3H), 2.29 (s, 3H), 1.94 (ddd, J=11.2, 8.2, 3.0 Hz, 1H), 1.70-1.82 (m, 1H), 1.62-1.70 (m, 2H), 1.13 (s, 3H), 1.08 (s, 3H); MS (M+1): 446.4.

Example 33

3-{4-[(3,3-dimethyl-cyclobutyl)-(3-methyl-quinolin-2-ylamino)-methyl]-benzoylamino}-propionic acid, isomer 2

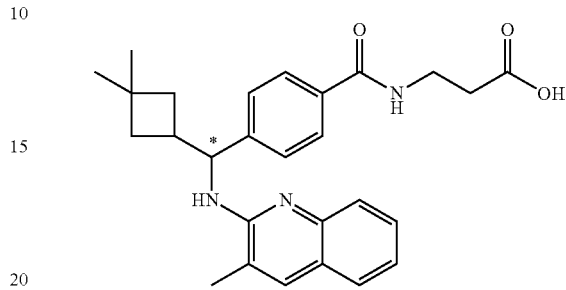

The title compound was prepared by treating 3-{4-[(3,3-dimethyl-cyclobutyl)-(3-methyl-quinolin-2-ylamino)-methyl]-benzoylamino}-propionic acid methyl ester, isomer 2 (intermediate 71) with 1N NaOH (2.5 eq.) in methanol/THF in a similar manner as described in Example 19 to provide the title compound. Analytical chiral SFC: (Chiralpak AD-H column, 4.6 mm×25 cm, 30% methanol/carbon dioxide eluent, 2.5 mL/min flow rate, 4.60 retention time); $^1$H NMR (400 MHz, CDCl$_3$) δ 7.66 (d, J=8.4 Hz, 2H), 7.58-7.63 (m, 2H), 7.44-7.51 (m, 3H), 7.37-7.44 (m, 1H), 7.10-7.18 (m, 1H), 6.81 (t, J=5.8 Hz, 1H), 5.30 (d, J=9.6 Hz, 1H), 3.67 (q, J=5.9 Hz, 2H), 2.52-2.70 (m, 3H), 2.29 (s, 3H), 1.94 (ddd, J=11.1, 8.0, 3.1 Hz, 1H), 1.72-1.82 (m, 1H), 1.63-1.72 (m, 2H), 1.13 (s, 3H), 1.08 (s, 3H); MS (M+1): 446.3.

Example 34

3-{4-[(3,3-dimethyl-cyclobutyl)-(6-fluoro-3-methyl-quinolin-2-ylamino)-methyl]-benzoylamino}-propionic acid, isomer 1

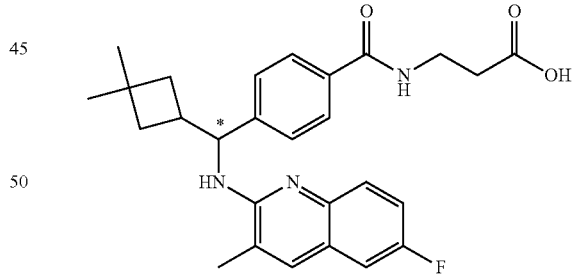

The title compound was prepared by treating 3-{4-[(3,3-Dimethyl-cyclobutyl)-(6-fluoro-3-methyl-quinolin-2-ylamino)-methyl]-benzoylamino}-propionic acid methyl ester, isomer 1, (intermediate 74) with 1N NaOH (2.5 eq.) in methanol/THF in a similar manner as described in Example 19 to provide the title compound. Analytical chiral SFC: (Chiralpak IC column, 4.6 mm×25 cm, 25% methanol/carbon dioxide eluent, 2.5 mL/min flow rate, 4.33 retention time); $^1$H NMR (400 MHz, DMSO-$d_6$) δ 12.14 (s, 1H), 8.38 (br. s., 1H), 7.63-7.76 (m, 3H), 7.55 (d, J=7.8 Hz, 2H), 7.39-7.50 (m, 1H), 7.30-7.39 (m, 1H), 7.21-7.30 (m, 1H), 6.45-6.60 (m, 1H), 5.11-5.28 (m, 1H), 3.41 (dd, J=12.7, 7.1 Hz, 2H), 2.75-2.91

(m, 1H), 2.46 (t, J=7.1 Hz, 2H), 2.29 (s, 3H), 1.92-2.00 (m, 1H), 1.56-1.67 (m, 2H), 1.42-1.55 (m, 1H), 1.12 (s, 3H), 1.07 (s, 3H); MS (M+1): 464.3.

Example 35

3-{4-[(3,3-dimethyl-cyclobutyl)-(6-fluoro-3-methyl-quinolin-2-ylamino)-methyl]benzoylamino}-propionic acid, isomer 2

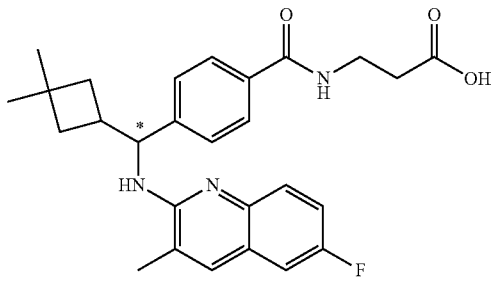 [SMILES: Cc1cc2cc(F)ccc2nc1NC(c1ccc(C(=O)NCCC(=O)O)cc1)C1CC(C)(C)C1]

The title compound was prepared by treating 3-{4-[(3,3-Dimethyl-cyclobutyl)-(6-fluoro-3-methyl-quinolin-2-ylamino)-methyl]-benzoylamino}-propionic acid methyl ester, isomer 2, (intermediate 75) with 1N NaOH (2.5 eq.) in methanol/THF in a similar manner as described in Example 19 to provide the title compound. Analytical chiral SFC: (Chiralpak IC column, 4.6 mm×25 cm, 25% methanol/carbon dioxide eluent, 2.5 mL/min flow rate, 4.81 retention time); $^1$H NMR (400 MHz, DMSO-$d_6$) δ 12.13 (s, 1H), 8.37 (t, J=5.5 Hz, 1H), 7.65-7.71 (m, 3H), 7.54 (d, J=8.3 Hz, 2H), 7.39-7.47 (m, 1H), 7.29-7.37 (m, 1H), 7.19-7.29 (m, 1H), 6.53 (d, J=8.1 Hz, 1H), 5.13-5.23 (m, 1H), 3.41 (dd, J=12.4, 6.8 Hz, 2H), 2.77-2.90 (m, 1H), 2.46 (t, J=7.1 Hz, 2H), 2.28 (s, 3H), 1.92-2.00 (m, 1H), 1.56-1.66 (m, 2H), 1.42-1.53 (m, 1H), 1.11 (s, 3H), 1.07 (s, 3H); MS (M+1): 464.2.

Biological Data

Glucagon cAMP Assay

The Cisbio cAMP detection assay is used to determine the ability of punitive glucagon antagonist to block glucagon induced cAMP production. Potential glucagon antagonists are re-suspended and diluted in 100% DMSO. Prior to use in the Glucagon cAMP assay 100×DMSO compound stocks are diluted 20× with DMEM-F12 media (Invitrogen) containing either 0.1% or 4% BSA. 2 uls of 5× compound stocks are spotted into the appropriate wells of low binding white solid bottom 384 well plates (Corning). 2 uls of 5% DMSO or known glucagon antagonist are added to each plate to define the assay window. CHOK1 cells stably transfected with the human glucagon receptor are removed from culture flasks with cell dissociation buffer. Cell pellets are re-suspended, at a concentration of 8.3e$^5$ cells/ml in DMEM-F12 with or without 4% BSA and 200 uM IBMX. 6 uls of cell suspensions are added to the assay plates. Plates are incubated for 20 min at room temperature prior to the addition of a 100 pM challenge dose of glucagon. On a separate plate glucagon dose response curves are run to determine the EC$_{50}$ of glucagon. After a 30 min room temperature incubation the reaction is terminated by the addition of lysis buffer containing the cAMP detection reagents. Plates are incubated for an additional 60 min at room temperature prior to being read on the Perkin Elmer fluorescent plate reader. Raw is converted to nM of cAMP produced based on a cAMP standard curve. Converted data is then analyzed using the Pfizer data analysis program. IC$_{50}$ values are determined from the generated sigmoidal dose response curves. Kb values are the calculated using a modified Cheng-Prusoff equation.

| Table of cAMP data | | |
|---|---|---|
| Example Number | N | cAMP Kb (nM) |
| Example 1 | 28 | 110 |
| Example 2 | 24 | 520 |
| Example 3 | 10 | 270 |
| Example 4 | 2 | 5,100 |
| Example 5 | 8 | 380 |
| Example 6 | 2 | 620 |
| Example 7 | 2 | 1,000 |
| Example 8 | 2 | 1,000 |
| Example 9 | 6 | 450 |
| Example 10 | 6 | 220 |
| Example 11 | 6 | 91 |
| Example 12 | 6 | 310 |
| Example 13 | 6 | 140 |
| Example 14 | 1 | 3,100 |
| Example 15 | 6 | 1,100 |
| Example 16 | 6 | 800 |
| Example 17 | 8 | 880 |
| Example 18 | 8 | 100 |
| Example 19 | 8 | 64 |
| Example 20 | 10 | 64 |
| Example 21 | 5 | 160 |
| Example 22 | 2 | 47 |
| Example 23 | 4 | 63 |
| Example 24 | 4 | 140 |
| Example 25 | — | — |
| Example 26 | — | — |
| Example 27 | 4 | 250 |
| Example 28 | — | — |
| Example 29 | 9 | 930 |
| Example 30 | 6 | 69 |
| Example 31 | 6 | 1300 |
| Example 32 | 6 | 23 |
| Example 33 | 6 | 1820 |
| Example 34 | 2 | 1180 |
| Example 35 | 2 | 33 |

Human Glucagon SPA Assay

The Glucagon SPA assay is used to determine the ability of test compounds to block the binding of glucagon-cex to the glucagon receptor. Test compounds are re-suspended and serially diluted in 100% DMSO. 1 ul of test compound at the desired concentrations is spotted into the appropriate wells of 96 well low binding white clear bottom plate (Corning). 1 ul of DMSO is spotted into total binding wells. 1 ul of a known glucagon antagonist at a concentration of 20 uM is added to non specific binding wells. 0.3-0.75 ug of membrane from chem-1 cells stably transfected with the human glucagon receptor (Millipore), 125 pM of [$^{125}$I]Glucagon-Cex (Perkin Elmer) and 175 ug of WGA PVT SPA beads (Perkin Elmer) are added to all wells of the assay plate. All assay ingredients with the exception of test compounds are re-suspended in the following buffer; 50 mM Hepes pH 7.4; 5 mM MgCl$_2$; 1 mM CaCl; 5% glycerol and 0.2% BSA. Following a 6-10 hr incubation at room temperature the amount of hot ligand bound to the cell membranes is determined by reading the plates on a Wallac Trilux radioactive emission detector. Data is analyzed using Pfizer's Data analysis program. IC$_{50}$ values are then determined from the generated sigmoidal dose response curves. Ki values are calculated using Cheng-Prusoff equation.

| Table for SPA Binding data | | |
|---|---|---|
| Example Number | N | Binding Ki (nM) |
| Example 1 | 11 | 173 |
| Example 2 | 5 | 280 |
| Example 3 | 5 | 240 |
| Example 4 | 1 | 7355 |
| Example 5 | 5 | 452 |
| Example 6 | 1 | 1855 |
| Example 7 | — | — |
| Example 8 | 1 | 979 |
| Example 9 | 4 | 531 |
| Example 10 | 4 | 198 |
| Example 11 | 4 | 101 |
| Example 12 | 4 | 242 |
| Example 13 | 4 | 199 |
| Example 14 | — | — |
| Example 15 | 4 | 479 |
| Example 16 | 4 | 91 |
| Example 17 | 3 | 360 |
| Example 18 | 3 | 109 |
| Example 19 | 4 | 74 |
| Example 20 | 3 | 39 |
| Example 21 | 2 | 133 |
| Example 22 | 2 | 25 |
| Example 23 | 2 | 50 |
| Example 24 | — | — |
| Example 25 | — | — |
| Example 26 | — | — |
| Example 27 | 2 | 160 |
| Example 28 | — | — |
| Example 29 | 4 | 930 |
| Example 30 | 2 | 76 |
| Example 31 | 1 | 1237 |
| Example 32 | 2 | 53 |
| Example 35 | 2 | 14 |

We claim:

1. A compound of Formula Ia'

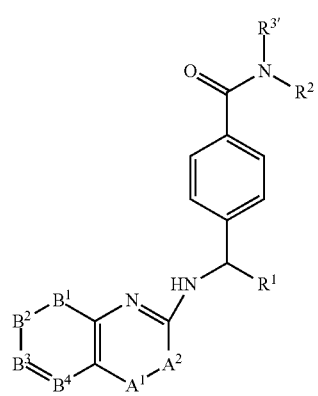

or a pharmaceutically acceptable salt thereof, wherein
$R^1$ is $(C_1-C_6)$alkyl which is optionally substituted with one to three fluoro, hydroxy or methoxy; $(C_3-C_7)$cycloalkyl which is optionally substituted with one to two fluoro or one to two $(C_1-C_3)$alkyl which are each optionally substituted with one to three fluoro and wherein one carbon of the $(C_3-C_7)$cycloalkyl can be replaced with an O; or $(C_3-C_7)$cycloalkyl-$(C_1-C_6)$alkyl wherein the $(C_3-C_7)$cycloalkyl group of said $(C_3-C_7)$cycloalkyl-$(C_1-C_6)$alkyl is optionally substituted with one to two $(C_1-C_3)$alkyl which are each optionally substituted with one to three fluoro;
$R^2$ is hydrogen or $(C_1-C_3)$alkyl;
$R^{3'}$ is —$(CH_2)_2CO_2R$, —$CH_2CHFCO_2R$, or —$CH_2CH(OH)CO_2R$;
R is $(C_1-C_4)$alkyl, benzyl, para-methoxybenzyl, or diphenylmethylene;
$A^1$ and $A^2$ are each independently $CR^4$;
$R^4$ at each occurrence is independently hydrogen, halo, cyano, $(C_1-C_3)$alkyl optionally substituted with one to three fluoro, $(C_1-C_3)$alkoxy optionally substituted with one to three fluoro, or $(C_3-C_5)$cycloalkyl;
$B^1$, $B^2$, $B^3$ and $B^4$ are each independently $CR^5$; and
$R^5$ at each occurrence is independently hydrogen, halo, cyano, $(C_1-C_3)$alkyl optionally substituted with one to three fluoro, or $(C_1-C_3)$alkoxy optionally substituted with one to three fluoro, or $(C_3-C_5)$cycloalkyl.

2. The compound according to claim 1, or a pharmaceutically acceptable salt thereof, wherein
$R^2$ is hydrogen;
$R^{3'}$ is —$(CH_2)_2CO_2R$; and
R is methyl, ethyl, or t-butyl.

3. The compound according to claim 2, or a pharmaceutically acceptable salt thereof, wherein $R^1$ is ethyl, propyl, isopropyl, isobutyl, t-butyl, pentyl, neopentyl, cyclopropyl, cyclobutyl, cyclopentyl, cyclohexyl or cyclopropylmethyl each optionally substituted with 1 to 3 fluoro and wherein said cyclopropyl, cyclobutyl, cyclopentyl, cyclohexyl are each optionally substituted with 1 to 2 methyl.

4. The compound according to claim 3, or a pharmaceutically acceptable salt thereof, wherein
$R^4$ at each occurrence is independently hydrogen, fluoro, chloro, methyl or ethyl; and
$R^5$ at each occurrence is independently hydrogen, fluoro, chloro, methyl, trifluoromethyl or methoxy.

5. A compound of structure

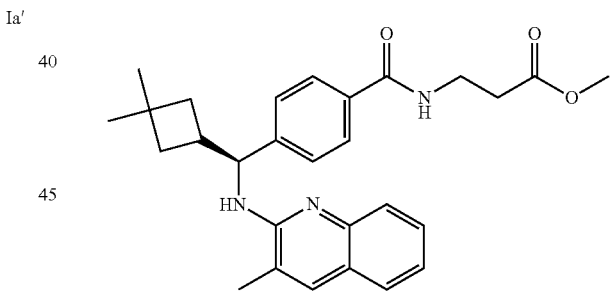

or a pharmaceutically acceptable salt thereof.

6. A compound of structure

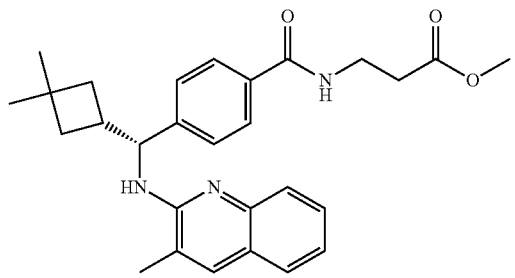

or a pharmaceutically acceptable salt thereof.

7. A compound of structure
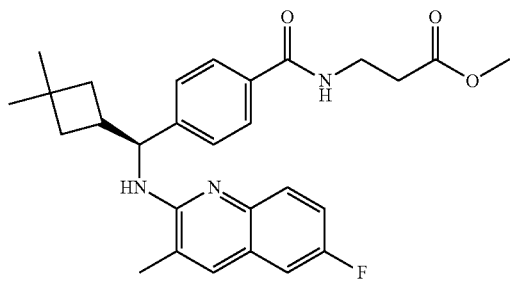
or a pharmaceutically acceptable salt thereof.
8. A compound of structure
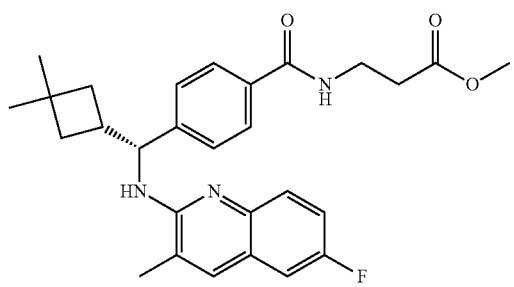
or a pharmaceutically acceptable salt thereof.
* * * * *